United States Patent
Cowley et al.

(10) Patent No.: US 10,501,458 B2
(45) Date of Patent: Dec. 10, 2019

(54) SUBSTITUTED BICYCLIC FUSED RING COMPOUNDS AS INDOLEAMINE-2,3-DIOXYGENASE INHIBITORS

(71) Applicants: Merck Sharp & Dohme Corp., Rahway, NJ (US); IOmet Pharma Ltd., Midlothian, Scotland (GB)

(72) Inventors: Phillip M. Cowley, Edinburgh (GB); Alan Wise, Edinburgh (GB); Thomas J. Brown, Edinburgh (GB); Meredeth A. McGowan, Boston, MA (US); Hua Zhou, Acton, MA (US); Yongxin Han, Needham, MA (US)

(73) Assignees: Iomet Pharma Ltd., Edinburgh, Scotland (GB); Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/738,365

(22) PCT Filed: Jul. 1, 2016

(86) PCT No.: PCT/US2016/040604
§ 371 (c)(1),
(2) Date: Dec. 20, 2017

(87) PCT Pub. No.: WO2017/007700
PCT Pub. Date: Jan. 12, 2017

(65) Prior Publication Data
US 2018/0186787 A1   Jul. 5, 2018

(30) Foreign Application Priority Data
Jul. 6, 2015   (GB) .................... 1511790.6

(51) Int. Cl.
| | | |
|---|---|---|
| *C07D 471/04* | (2006.01) | |
| *A61K 31/4545* | (2006.01) | |
| *A61K 45/06* | (2006.01) | |
| *A61K 31/437* | (2006.01) | |
| *A61K 31/4523* | (2006.01) | |
| *A61K 31/496* | (2006.01) | |

(52) U.S. Cl.
CPC .......... *C07D 471/04* (2013.01); *A61K 31/437* (2013.01); *A61K 31/4523* (2013.01); *A61K 31/4545* (2013.01); *A61K 31/496* (2013.01); *A61K 45/06* (2013.01)

(58) Field of Classification Search
CPC ............. C07D 471/04; A61K 31/4545; A61K 31/4523; A61K 31/437; A61K 31/496; A61K 45/06
See application file for complete search history.

(56) References Cited

U.S. PATENT DOCUMENTS

| | | |
|---|---|---|
| 4,617,307 A | 10/1986 | Browne |
| 4,889,861 A | 12/1989 | Browne |
| 2007/0078156 A1 | 4/2007 | Fletcher et al. |
| 2007/0197582 A1 | 8/2007 | Firooznia |
| 2011/0021521 A1 | 1/2011 | Corkey et al. |
| 2014/0066625 A1 | 3/2014 | Mautino et al. |
| 2014/0377292 A1 | 12/2014 | Combs et al. |

FOREIGN PATENT DOCUMENTS

| | | |
|---|---|---|
| GB | 2174094 A | 10/1986 |
| WO | WO2008057855 A2 | 5/2008 |
| WO | WO2008110523 A1 | 9/2008 |
| WO | WO2009085980 A1 | 7/2009 |
| WO | WO2011130342 A1 | 10/2011 |
| WO | WO2015082499 | 6/2015 |
| WO | WO2016161960 A1 | 10/2016 |

OTHER PUBLICATIONS

NPL-PubChem-CID-25012945-2008.
NPL-PubChem-CID-83887256-2014.
Blatcher, P et al, A direct method for the substitution of imidazo[1,5-a]pyridines at position 5, Tetrahedron Letters, 1980, 2195-2196, 21(22).
Davey, D et al, Cardiotonic Agents. 1. Novel 8-Aryl-Substituted Imidazo[1,2-a]- and -[1,5-a]pyridines and Imidazo [1,5-a]pyridinones as Potential Positive Inotropic Agents, Journal of Medicinal Chemistry, American Chemical Society, 1987, 1337-1342, 30.
Davey, DD, Snythesis of novel 8-arylimidazo[1,2-a]pyridines and 8-arylimidazo[1,5-s]pyridines, Journal of Organic Chemistry, 1987, 1863-1867, 52(9).
Ford, NF et al, Imidazo[1,5-a]pyridines: A New Class of Thromboxane A2 Synthetase Inhibitors, Journal of Medicinal Chemistry, 1983, 164-170, 28(2).
Huang, J et al, Rhodium(III)-Catalyzed Direct Selective C(5)-H Oxidative Annulations of 2-Substituted Imidazoles and Alkynes by Double C-H Activation, Organic Letters, American Chemical Society, 2013, 1878-1881, 15(8).
List of Compounds, Annex, 1-13, (1985-2008).

*Primary Examiner* — Emily A Bernhardt
*Assistant Examiner* — Laura M Daniel
(74) *Attorney, Agent, or Firm* — Yong Zhao; Anna L. Cocuzzo

(57) ABSTRACT

Provided is a tryptophan-2,3-dioxygenase (TDO) and/or indoleamine-2,3-dioxygenase (IDO) inhibitor compound for use in medicine, which compound comprises the general formula (I) detailed within.

(I)

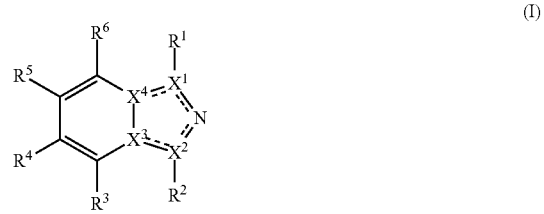

9 Claims, 2 Drawing Sheets

SUBSTITUTED BICYCLIC FUSED RING COMPOUNDS AS INDOLEAMINE-2,3-DIOXYGENASE INHIBITORS

CROSS-REFERENCE TO RELATED APPLICATIONS

The present application is a 371 national phase application of international application no. PCT/US2016/040604, filed Jul. 1, 2016, which claims the benefit of GB Application No. 1511790.6, filed Jul. 6, 2015; hereby incorporated by reference in its entirety.

BACKGROUND OF THE INVENTION

The present invention relates to tryptophan-2,3-dioxygenase (TDO) or indoleamine-2,3-dioxygenase (IDO [IDO1 or IDO2]) inhibitors, and in particular TDO and IDO inhibitors for use in medicine. The inhibitors of the invention may be used in pharmaceutical compositions, and in particular pharmaceutical compositions for treating a cancer, an inflammatory condition, an infectious disease, a central nervous system disease or disorder and other diseases, conditions and disorders. The invention also relates to methods of manufacture of such inhibitors, and methods of treatment using such inhibitors.

Tryptophan metabolism—The kynurenine pathway (KP) is responsible for >95% of the degradation of the essential amino acid tryptophan. The kynurenine pathway for tryptophan metabolism leads to the production of the essential pyridine nucleotide NAD+ and a number of neuroactive metabolites, including kynurenine (KYN), kynurenic acid (KYNA), the neurotoxic free-radical generator 3-hydroxykynurenine (3-HK), anthranilic acid, 3-HAA, picolinic acid (PIC), and the excitatory N-methyl-D-aspartate (NMDA) receptor agonist and neurotoxin, quinolinic acid (QUIN) (see FIG. 1). The remaining 5% of tryptophan is metabolised by tryptophan hydroxylase to 5-hydroxytryptophan and then further to 5-hydroxytryptamine (serotonin) and melatonin.

Both the depletion of tryptophan and accumulation of immunosuppressive tryptophan catabolites act to supress antigen-specific T-cell and natural killer cell responses and induce the formation of regulatory T cells. Because tryptophan catabolism is induced by inflammatory mediators, notably IFN-γ, it is thought to represent an endogenous mechanism that restricts excessive immune responses, thereby preventing immunopathology. However, there is evidence that in disease states this feedback loop may not be beneficial (reviewed in (Munn and Mellor, 2013).

IDO/TDO—The first step of tryptophan catabolism is catalysed by either TDO or IDO. Both enzymes catalyze the oxidative cleavage of the 2,3 double bond in the indole ring, converting tryptophan to N-formylkynurenine. This is the rate-limiting step in tryptophan catabolism by the kynurenine pathway (Grohmann et al., 2003; Stone and Darlington, 2002). TDO is a homotetramer with each monomer having a molecular mass of 48 kDa, whereas IDO has a molecular mass of 45 kDa and a monomeric structure (Sugimoto et al., 2006; Thackray et al., 2008; Zhang et al., 2007). Despite mediating the same reaction, TDO and IDO are structurally distinct, sharing only 10% homology mainly within the active site (Thackray et al., 2008).

TDO is expressed at high levels in the liver and is responsible for regulating systemic tryptophan levels. TDO is not induced or regulated by signals from the immune system, however TDO expression can be induced by tryptophan or corticosteroids (Miller et al., 2004; Salter and Pogson, 1985). More recently, TDO has been found to be expressed in the brain, where it regulates the production of neuroactive tryptophan metabolites such as kynurenic acid and quinolinic acid (Kanai et al., 2009).

IDO is the predominant tryptophan catabolising enzyme extra hepatically and is found in numerous cells, including macrophages, microglia, neurons and astrocytes (Guillemin et al., 2007; Guillemin et al., 2001; Guillemin et al., 2003; Guillemin et al., 2005). IDO transcription is stringently controlled, responding to specific inflammatory mediators. The mouse and human IDO gene promoters contain multiple sequence elements that confer responsiveness to type I (IFN-α/β) and, more potently, type II (IFN-γ) interferons (Chang et al., 2011; Dai and Gupta, 1990; Hassanain et al., 1993; Mellor et al., 2003). Various cell types, including certain myeloid-lineage cells (monocyte-derived macrophages and DCs), fibroblasts, endothelial cells and some tumour-cell lines, express IDO after exposure to IFN-γ (Burke et al., 1995; Hwu et al., 2000; Mellor et al., 2003; Munn et al., 1999; Varga et al., 1996). However, the control of IDO transcription is complex and cell-type specific. IDO activity is found constitutively at the maternalfetal interface, expressed by human extravillous trophoblast cells (Kudo and Boyd, 2000). Outside of the placenta, functional IDO expression was reported to be highest in the mouse epididymis, gut (distal ileum and colon), lymph nodes, spleen, thymus and lungs (Takikawa et al., 1986).

Another recent variant enzyme of IDO has been shown to catalyse the same enzymatic step: indoleamine-2,3-dioxygenase 2 (IDO2). However, its physiological relevance remains unclear due to its very low activity, the presence of common polymorphisms that inactivate its enzymatic activity in approximately half of all Caucasians and Asians, and the presence of multiple splice variants (Lob et al., 2008; Meininger et al., 2011; Metz et al., 2007). IDO-deficient mice are at a gross level phenotypical normal (Mellor et al., 2003), however, they are slightly more prone to induction of autoimmunity and stimulation of the innate immune system. IDO −/− knockout mice also display enhanced inflammatory-mediated colon carcinogenesis and exhibit resistance to inflammation-driven lung and skin cancers (Chang et al., 2011; Yan et al., 2010).

The TDO −/− knockout mouse appears phenotypically normal. However, the TDO knockout mice have a 9-fold increase in the plasma concentration of L-Trp, while IDO −/− knockout mice had WT levels of L-Trp, this suggests that TDO and not IDO regulates systemic Trp. TDO ablation increases Trp in the brain as well as serotonin (5-HT) and is therefore a modulator of anxiety related behaviour (Kanai et al., 2009). TDO also plays a role in the maintenance of brain morphology in adult mice as TDO −/− mice show increased neurogenesis in the hippocampus and subventricular zone during adulthood (Funakoshi et al., 2011).

Immuno-modulation: Tryptophan Depletion and Kynurenine Accumulation

Immunoregulation by tryptophan metabolism modulates the immune system by depletion of the TDO/IDO substrate (tryptophan) in the microenvironment and the accumulation of products such as kynurenine.

Effector T cells are particularly susceptible to low tryptophan concentrations, therefore, depletion of the essential amino acid tryptophan from the local microenvironment resulting in effector T-cell energy and apoptosis. The depletion of tryptophan is detected by the general control non-derepressible-2 kinase (GCN2) (Munn et al., 2005). The activation of GCN2 triggers a stress-response program that results in cell-cycle arrest, differentiation, adaptation or apoptosis. T cells lacking GCN2 in mice are not susceptible to IDO-mediated energy by myeloid cells, including dendritic cells in tumor-draining lymph nodes (Munn et al., 2005).

Tryptophan metabolites such as kynurenine, kynurenic acid, 3-hydroxy-kynurenine, and 3-hydroxy-anthranilic acid suppress T-cell function and are capable of inducing T-cell apoptosis. Recent studies have shown that the aryl hydrocarbon receptor (AHR) is a direct target of kynurenine (Mezrich et al., 2010; Nguyen et al., 2010; Opitz et al., 2011). The AHR is a basic helix-loop-helix Per-Arnt-Sim (PAS) family transcription factor. As kynurenine accumulates in a tumour, KYN binds the AHR, translocates to the nucleus and activates transcription of target genes regulated by dioxin-responsive elements (DREs). In T-helper-cells kynurenine results in the generation of regulatory T cells (Treg).

SUMMARY OF THE INVENTION

Disclosed herein are tryptophan-2,3-dioxygenase (TDO) and/or indoleamine-2,3-dioxygenase (IDO) inhibitor compounds having the following formula:

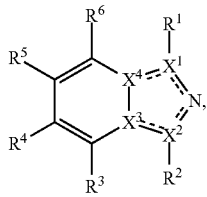

or a pharmaceutically acceptable salt thereof, wherein each variable is as defined below.

DETAILED DESCRIPTION OF THE INVENTION

Figure 1:
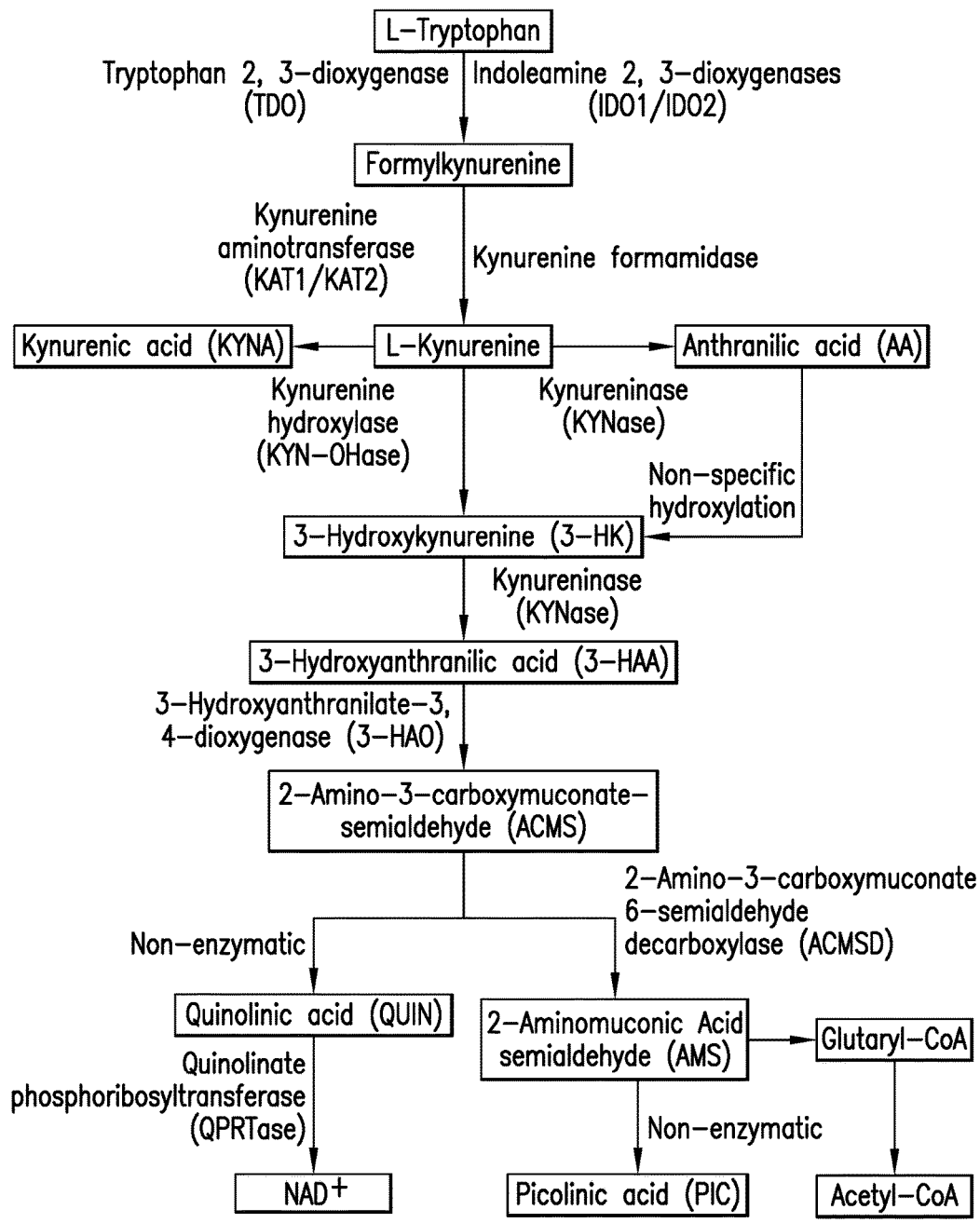
FIG. 1 shows a schematic diagram of tryptophan catabolism along the Kynurenine Pathway in Brain Tumour Pathogenesis (also see Adam et al., 2012, Cancer Res 72:5649-57).

Described herein are TDO and/or IDO inhibitor compounds having the following formula, or a pharmaceutically acceptable salt thereof, for use in medicine:

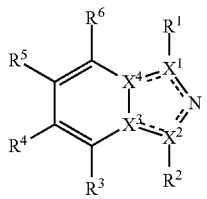

wherein $X^1$, and $X^2$ may be the same or different and each is independently selected from C, and N; $X^3$ and $X^4$ are each independently selected from C and N, wherein one of $X^3$ and $X^4$ is C and one of $X^3$ and $X^4$ is N; each bond represented by a dotted line may be present or absent, provided that one of $X^3$ and $X^4$ has a double bond and the N between $X^1$ and $X^2$ has a double bond and the valencies of $X^1$, $X^2$, $X^3$, $X^4$ and N are maintained; $R^1$ and $R^2$ may be present or absent and may be the same or different and each is independently selected from H and a substituted or unsubstituted organic group, provided that the number of $R^1$ and $R^2$ groups present is such that the respective valencies of $X^1$ and $X^2$ are maintained; $R^3$, $R^4$, $R^5$ and $R^6$ may be the same or different and each is independently selected from H and a substituted or unsubstituted organic group; and wherein at least one of $R^5$ and $R^6$ comprises a group Y, wherein Y is a group having a formula selected from the following:

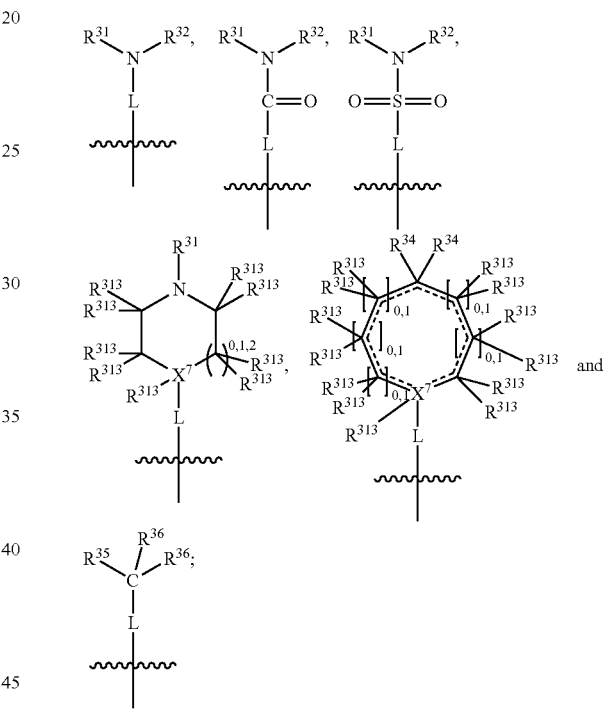

wherein L may be present or absent, and may be a substituted or unsubstituted organic linking group; $R^{31}$ and $R^{32}$ may be the same or different and are selected from H and a substituted or unsubstituted organic group; each $R^{34}$ may be the same or different and is selected from H and a substituted or unsubstituted organic group; $R^{35}$ is selected from a substituted or unsubstituted alcohol group or ether group; each $R^{36}$ may be the same or different and is selected from H and a substituted or unsubstituted organic group; $X^7$ is selected from C and N; in the group represented by the eight-membered ring each bond represented by a dotted line may be present or absent provided that the valencies of the C atoms and $X^7$ are maintained; and each $R^{313}$ may be the same or different and is selected from H and a substituted or unsubstituted organic group. Typically the fused bicyclic ring system in this structure is aromatic.

Any of the compounds disclosed herein is typically suitable for use in medicine in a treatment comprising TDO and/or IDO inhibition(s).

As used herein, maintaining the valency means ensuring that an atom has its normal (typically most common) valency in organic compounds (i.e. 2 for oxygen and sulphur, 3 for nitrogen and 4 for carbon). Nitrogen atoms may, in some instances, have 4 bonds, but in such cases they are typically positively charged such that the compound may have a counter-ion. Such compounds are also considered to be part of the invention, and in these cases, due to the positive charge, it will be clear that the nitrogen atom still maintains its normal valency of 3. For the avoidance of doubt, where the number of R groups may vary according to the choice of X group, it may vary as follows.

$R^1$ is absent when $X^1$ is N and has a double bond, and one $R^1$ is present when $X^1$ is C with a double bond. $R^2$ is absent when $X^2$ is N and has a double bond, and one $R^2$ is present when $X^2$ is C with a double bond. The $R^{313}$ on $X^7$ is absent when $X^7$ is N, or when $X^7$ is C and has a double bond, and one $R^{313}$ is present on $X^7$ when $X^7$ is C and does not have a double bond.

Disclosed herein are compounds in which a single $R^{313}$ group on an atom, or two $R^{313}$ groups on the same atom, may form a group which is double bonded to that atom. Accordingly, an $R^{313}$ group, or two $R^{313}$ groups attached to the same atom, may together form a =O group, or a =C(R')$_2$ group (wherein each R' group is the same or different and is H or an organic group, preferably H or a straight or branched substituted or unsubstituted $C_1$-$C_6$ alkyl group). Typically, all $R^{313}$ groups are H, or one or more of the $R^{313}$ groups adjacent to the N—$R^{31}$, (or adjacent to the (C—$R^{34}$)) and/or adjacent to the $X^7$, are not H. In some instances two $R^{313}$ groups on the same atom adjacent to the N—$R^{31}$, (or adjacent to the (C—$R^{34}$)) and/or adjacent to the $X^7$, are not H, and in other instances one $R^{313}$ group on each of the two different atoms adjacent to the N—$R^{31}$, (or adjacent to the (C—$R^{34}$)) and/or adjacent to the $X^7$, is not H. Typically, one or more of the $R^{313}$ groups adjacent to the N—$R^{31}$, (or adjacent to the (C—$R^{34}$)) and/or adjacent to the $X^7$, are selected from a $C_1$-$C_6$ alkyl group. In some instances two $R^{313}$ groups on the same atom adjacent to the N—$R^{31}$, (or adjacent to the (C—$R^{34}$)) and/or adjacent to the $X^7$, may form a ring, preferably a substituted or unsubstituted $C_3$-$C_6$ saturated carbocyclic ring together with the atom to which they are attached (such as a substituted or unsubstituted cyclopropyl ring or a substituted or unsubstituted cyclobutyl ring).

In one embodiment, an R group in the ring system may form a ring with another R group on an adjacent and/or proximal atom, although this is not typical. Thus, the following substituents may together form a ring: $R^1$ and $R^6$, $R^2$ and $R^3$, $R^3$ and $R^4$, $R^4$ and $R^5$, and $R^5$ and $R^6$. In the context of the present invention, an adjacent and/or proximal atom may mean another atom directly bonded to an atom (adjacent), or may be two atoms with only a single atom in between (proximal), or may mean two atoms close enough sterically to be capable of forming a ring (proximal). Preferably R groups attached to the same atom do not together form a ring, although this is not excluded (for example, in the case of $R^{313}$ above). In some cases, any R group or L in the Y group may form a ring with any other group on an adjacent and/or proximal atom, although this is not typical; the other group may be a group either in the ring system or in the Y group. Thus, in certain embodiments the following substituents may each together form a ring: $R^{31}$ and $R^{32}$, L and $R^{31}$ and/or L and $R^{32}$, $R^{31}$ with $R^{313}$, $R^{32}$ with $R^{313}$, $R^{313}$ with another $R^{313}$ (either another $R^{313}$ on the same atom or an $R^{313}$ on a different atom), $R^{34}$ with another $R^{34}$, $R^{35}$ with an $R^{36}$, $R^{35}$ with L, $R^{36}$ with another $R^{36}$, one or both of $R^{36}$ with one or more $R^{313}$ and one or both of $R^{36}$ with L. In addition, the following substituents may each together form a ring: $R^1$ and L, $R^1$ and $R^{31}$, $R^1$ and $R^{32}$, $R^1$ and $R^{35}$, $R^1$ and $R^{36}$, $R^2$ and L, $R^2$ and $R^{31}$, $R^2$ and $R^{32}$, $R^2$ and $R^{35}$, $R^2$ and $R^{36}$, $R^3$ and L, $R^3$ and $R^{31}$, $R^3$ and $R^{32}$, $R^3$ and $R^{35}$, $R^3$ and $R^{36}$, $R^4$ and L, $R^4$ and $R^{31}$, $R^4$ and $R^{32}$, $R^4$ and $R^{35}$, $R^4$ and $R^{36}$, $R^5$ and L, $R^5$ and $R^{31}$, $R^5$ and $R^{32}$, $R^5$ and $R^{35}$, $R^5$ and $R^{36}$, and $R^6$ and L, $R^6$ and $R^{31}$, $R^6$ and $R^{32}$, $R^6$ and $R^{35}$, $R^6$ and $R^{36}$.

As used herein, the dotted line between two atoms indicates the possible presence of a further bond. In a case where two atoms are already joined by a solid line, but also have a dotted line, then those atoms have at least a single bond, but possibly a double bond in some cases. Thus, in such cases, each atom having a dotted line may independently have a double bond or a single bond, provided that valencies at each atom are maintained.

As used herein, the structure present in brackets may be repeated the number of times given by the numbers next to the brackets (whether regular brackets or square brackets). For example, in the case of $(C(R))_{0,1,2}$ or $[C(R)]_{0,1,2}$ the C—R group may be absent, present once i.e. —C(R)—; or present twice i.e. —C(R)—C(R)—.

A compound is considered to be a TDO inhibitor if its presence is capable of preventing, reducing or slowing the conversion of tryptophan into N-formylkynurenine by TDO as compared to the same conversion in its absence. Similarly, in the context of the present invention, a compound is considered to be an IDO inhibitor if its presence is capable of preventing, reducing or slowing the conversion of tryptophan into N-formylkynurenine by IDO as compared to the same conversion in its absence. The compounds of the invention may be selective TDO inhibitors, or selective IDO inhibitors, or may be inhibitors of both IDO and TDO.

In one embodiment, a compound is of a formula selected from the following:

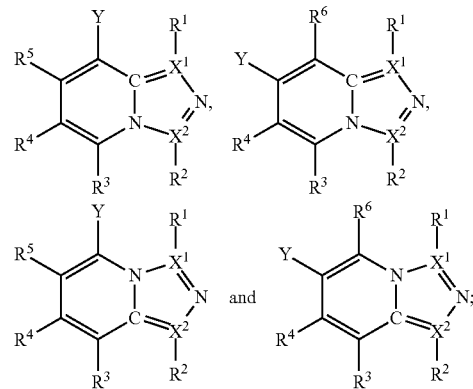

wherein each of the variables Y, R and X has the same meaning as above and below herein. Thus, in typical embodiments the compound takes the form of a substituted fused heterocyclic compound wherein the ring system comprises an aromatic 6-membered heterocyclic ring fused to an aromatic heterocyclic 5-membered ring.

In one embodiment, the Y group is not especially limited, provided that it does not prevent the TDO or IDO inhibitory function from occurring. In certain typical embodiments, both above and in the following, the Y group comprises an aminocarbonyl group, a carbonylamino group, an aminosulphonyl group, a sulphonylamino group, a substituted or unsubstituted piperidinyl group, a substituted or unsubstituted piperazinyl group, a substituted or unsubstituted alcohol group, a substituted or unsubstituted ether group, and/or a saturated or unsaturated, substituted or unsubstituted, carbocyclic group such as a substituted or unsubstituted cyclohexyl group or a substituted or unsubstituted phenyl group.

In one embodiment, the substituents (each of the R groups) are not especially limited, provided that they do not prevent the TDO or IDO inhibitory function from occurring. In all of the embodiments mentioned in connection with this invention, both above and in the following, the substituents are selected from H and an organic group. Thus, both above and in the following, the terms 'substituent' and 'organic group' are not especially limited and may be any functional group or any atom, especially any functional group or atom common in organic chemistry. Thus, 'substituent' and 'organic group' may have any of the following meanings.

The organic group may comprise any one or more atoms from any of groups IIIA, IVA, VA, VIA or VIIA of the Periodic Table, such as a B, Si, N, P, O, or S atom (e.g. OH, OR, $NH_2$, NHR, $NR_2$, SH, SR, $SO_2R$, $SO_3H$, $PO_4H_2$) or a halogen atom (e.g. F, Cl, Br or I) where R is a linear or branched lower hydrocarbon (1-6 C atoms) or a linear or branched higher hydrocarbon (7 C atoms or more, e.g. 7-40 C atoms).

The organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, pyrrolidine, piperidine, morpholine, thiophene, benzothiophene, furan, benzofuran, pyrrole, indole, imidazole, thiazole, diazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The lower hydrocarbon group may be a methyl, ethyl, propyl, butyl, pentyl or hexyl group or regioisomers of these, such as isopropyl, isobutyl, tert-butyl, etc. The number of atoms in the ring of the cyclic group is not especially limited, but preferably the ring of the cyclic group comprises from 3-10 atoms, such as 3, 4, 5, 6, 7, 8, 9 or 10 atoms.

The groups comprising heteroatoms described herein comprise one or more heteroatoms from any of groups IIIA, IVA, VA, VIA or VIIA of the Periodic Table, such as a B, Si, N, P, O, or S atom or a halogen atom. Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, sulphonyl groups, and phosphate groups etc. The substituent may also comprise derivatives of these groups, such as carboxylic acid anhydrides and carboxylic acid halides.

In addition, any substituent may comprise a combination of two or more of the substituents and/or functional groups defined above.

As used herein, "alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Cycloalkyl" refers to a monocyclic saturated carbocyclic ring having the specified number of carbon atoms. For example, $C_{3-7}$ cycloalkyl refers to a cycloalkyl group as defined herein having 3 to 7 carbon atoms. Examples of cycloalkyl include, but are not limited to, cyclopropyl, cyclobutyl, cyclopentyl, cyclohexyl and cycloheptanyl. Cycloalkyl groups may be optionally substituted with one or more substituents as defined herein.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, furanyl, imidazolyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl.

In one embodiment, saturated 4-7 membered monocyclic heterocyclyl moieties include, but are not limited to, azetidinyl, 1,4-dioxanyl, hexahydroazepinyl, imidazolidinyl, morpholinyl, 1,4-oxazepanyl, oxazolidinyl, oxetanyl, piperazinyl, piperidinyl, pyridin-2-onyl, pyrrolidinyl, tetrahydrofuranyl, tetrahydropyranyl, thiomorpholinyl, tetrahydrothienyl, and tetrahydrothiophenyl. In one embodiment, a saturated 4-7 membered monocyclic heterocyclyl is azetidinyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

In one embodiment, a number of typical general structures of the compounds disclosed herein are described below.

As has been described, the invention relates to a tryptophan-2,3-dioxygenase (TDO) and/or indoleamine-2,3-dioxygenase (IDO) inhibitor compound for use in medicine, which compound comprises the following formula:

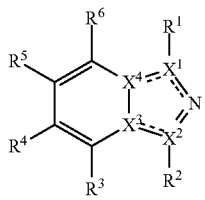

wherein $X^1$, and $X^2$ may be the same or different and each is independently selected from C, and N; $X^3$ and $X^4$ are each independently selected from C and N, wherein one of $X^3$ and $X^4$ is C and one of $X^3$ and $X^4$ is N; each bond represented by a dotted line may be present or absent, provided that one of $X^3$ and $X^4$ has a double bond and the N between $X^1$ and $X^2$ has a double bond and the valencies of $X^1$, $X^2$, $X^3$, $X^4$ and N are maintained; $R^1$ and $R^2$ may be present or absent and may be the same or different and each is independently selected from H and a substituted or unsubstituted organic group, provided that the number of $R^1$ and $R^2$ groups present is such that the respective valencies of $X^1$ and $X^2$ are maintained; $R^3$, $R^4$, $R^5$ and $R^6$ may be the same or different and each is independently selected from H and a substituted or unsubstituted organic group; and wherein at least one of $R^5$ and $R^6$ comprises a group Y, wherein Y is a group having a formula selected from the following:

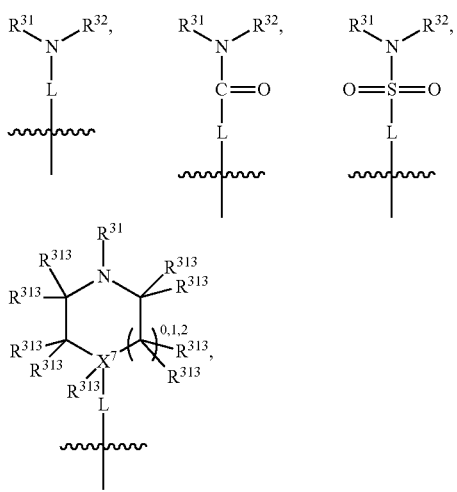

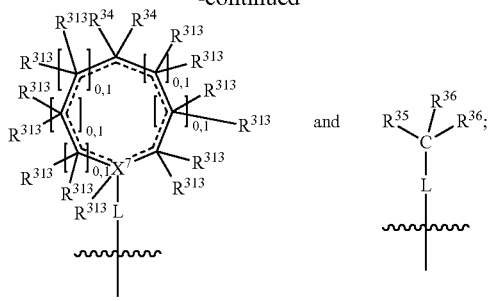

wherein L may be present or absent, and may be a substituted or unsubstituted organic linking group; $R^{31}$ and $R^{32}$ may be the same or different and are selected from H and a substituted or unsubstituted organic group; each $R^{34}$ may be the same or different and is selected from H and a substituted or unsubstituted organic group; $R^{35}$ is selected from a substituted or unsubstituted alcohol group or ether group; each $R^{36}$ may be the same or different and is selected from H and a substituted or unsubstituted organic group; $X^7$ is selected from C and N; in the group represented by the eight-membered ring each bond represented by a dotted line may be present or absent provided that the valencies of the C atoms and $X^7$ are maintained; and each $R^{313}$ may be the same or different and is selected from H and a substituted or unsubstituted organic group.

The fused bicyclic ring system is aromatic. All tautomeric forms of the ring system (including the tautomeric forms of the 6-membered ring and the tautomeric forms of the 5-membered ring) are included.

The group L is a linking group and is not especially limited provided that it does not impair the IDO or TDO inhibitory activity of the compounds. It may be present or absent. When absent, the N atom (or the $X^7$, or the $C(R^{35})$, or the C=O, or the O=S=O) of group Y is directly attached to the ring system. When present, L may be divalent, such that it may simply link the N atom of group Y (or the $X^7$, or the $C(R^{35})$, or the C=O, or the O=S=O of group Y) to the bicyclic fused ring system. Alternatively L may be trivalent if in addition it forms a ring with $R^{31}$ or $R^{32}$ (or with $R^{35}$ or $R^{36}$), and further alternatively L may be quadravalent if it forms a ring with both $R^{31}$ and $R^{32}$ (or with $R^{35}$ and $R^{36}$).

In one embodiment, both above and below herein, $X^1$ and $X^2$ are both C atoms. In other typical embodiments, both above and below herein, one of $X^1$ and $X^2$ is N. Thus in some embodiments $X^1$ is a C atom and $X^2$ is an N atom, and in alternative embodiments $X^2$ is a C atom and $X^1$ is an N atom. In yet further alternative embodiments, both of $X^1$ and $X^2$ are N.

In one embodiment, both above and below herein, Y comprises an aminocarbonyl group, a carbonylamino group, an aminosulphonyl group, a sulphonylamino group, a substituted or unsubstituted piperidinyl group, a substituted or unsubstituted piperazinyl group, a substituted or unsubstituted alcohol group, a substituted or unsubstituted ether group, and/or a saturated or unsaturated, substituted or unsubstituted, carbocyclic group such as a substituted or unsubstituted cyclohexyl group or a substituted or unsubstituted phenyl group.

In one embodiment, both above and below herein, L is absent. In another embodiment, L may comprise a substituted or unsubstituted $C_1$-$C_7$ alkylene group (such as —CH$_2$—, —CH$_2$CH$_2$—, —CH$_2$CH$_2$CH$_2$—, —CH(CH$_3$)

CH$_2$—, —C(CH$_3$)$_2$—, —CH$_2$CH$_2$CH$_2$CH$_2$—, —CH(CH$_3$)CH$_2$CH$_2$—, —CH(CH$_3$)CH(CH$_3$)—, —CH(CH$_2$CH$_3$)CH$_2$—, —C(CH$_3$)$_2$CH$_2$—, —CH$_2$CH$_2$CH$_2$CH$_2$CH$_2$—, and —CH$_2$CH$_2$CH$_2$CH$_2$CH$_2$CH$_2$—), or a C$_1$-C$_7$ divalent alkoxy group (such as —OCH, —OCH$_2$CH$_2$—, —OCH$_2$CH$_2$CH$_2$, —O—CH(CH$_3$)CH$_2$—, —OC(CH$_3$)$_2$—, —OCH$_2$CH$_2$CH$_2$CH$_2$—, —OCH(CH$_3$)CH$_2$CH$_2$—, —OCH(CH$_3$)CH(CH$_3$)—, —OCH(CH$_2$CH$_3$)CH$_2$—, —OC(CH$_3$)$_2$CH$_2$—, —OCH$_2$CH$_2$CH$_2$CH$_2$CH$_2$—, —OCH$_2$CH$_2$CH$_2$CH$_2$CH$_2$CH$_2$—, —OCHF—, —OCF$_2$—, —O-phenylene-, —O—CH$_2$-phenylene-, —O—CH$_2$-(2,3 or 4)-F-phenylene-, —O—CH$_2$-(2,3 or 4)-Cl-phenylene-, —CH$_2$OCH$_2$—, —CH$_2$OCH$_2$CH$_2$—, —CH$_2$OCH$_2$CH$_2$CH$_2$—, —CH$_2$OCH$_2$CH$_2$CH$_2$CH$_2$—, —CH$_2$CH$_2$OCH$_2$—, —CH$_2$CH$_2$CH$_2$OCH$_2$—, —CH$_2$CH$_2$CH$_2$CH$_2$OCH$_2$—, —CH$_2$CH$_2$CH$_2$CH$_2$CH$_2$OCH$_2$—, —CH$_2$CH$_2$CH$_2$CH$_2$CH$_2$CH$_2$OCH$_2$—, —CH$_2$CH$_2$OCH$_2$CH$_2$—, —CH$_2$CH$_2$OCH$_2$CH$_2$CH$_2$—, —CH$_2$CH$_2$OCH$_2$CH$_2$CH$_2$CH$_2$—, —CH$_2$CH$_2$OCH$_2$CH$_2$CH$_2$CH$_2$CH$_2$—, —CH$_2$CH$_2$CH$_2$OCH$_2$CH$_2$—, —CH$_2$CH$_2$CH$_2$OCH$_2$CH$_2$CH$_2$—, and —CH$_2$CH$_2$CH$_2$OCH$_2$CH$_2$CH$_2$CH$_2$—. Alternatively, L may be an —O— atom, or an —N(R$^{32}$)— group (such as an —NH— group).

Thus, in view of the typical compounds already described, in more typical embodiments the invention relates to a compound comprising one of the following formulae:

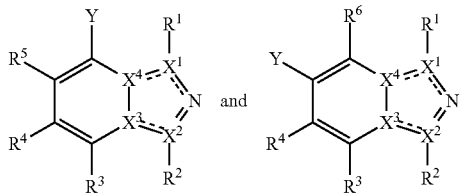

wherein, in each case, the substituents Y, R and X are as defined in any of the above and below embodiments described herein.

In one embodiment, both above and below herein, the 6-membered ring of the bicyclic fused ring system is aromatic and the 5-membered ring of the bicyclic fused ring system is aromatic, and the bicyclic fused ring system as a whole is aromatic.

Furthermore, in view of the typical compounds already described, in more typical embodiments the invention relates to a compound comprising one of the following formulae:

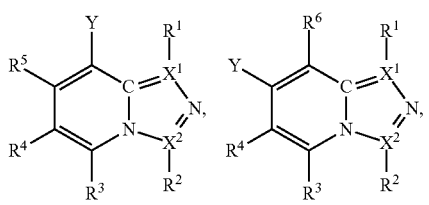

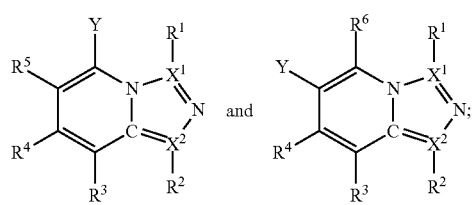

wherein, in each case, the substituents Y, X and R are as defined in any of the above or below embodiments described herein.

Furthermore, in view of the typical compounds already described, in more typical embodiments the invention relates to a compound comprising one of the following formulae:

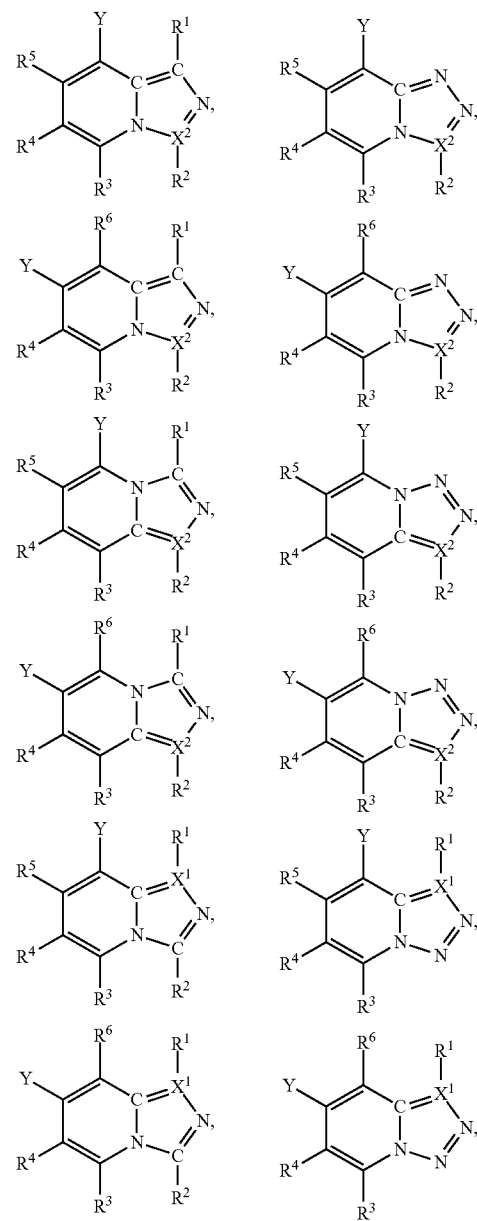

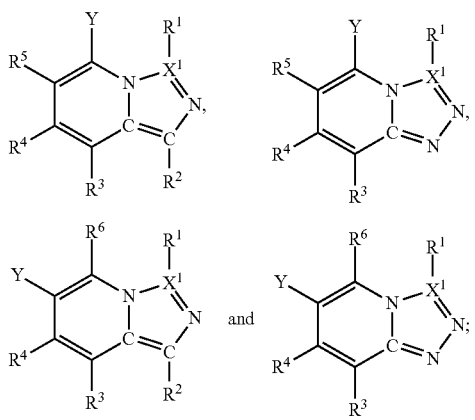

preferably wherein the compound comprises one of the following formulae:

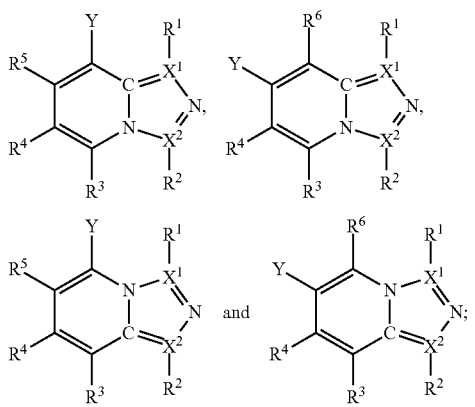

wherein, in each case, the substituents Y, X and R are as defined in any of the above or below embodiments described herein.

Furthermore, in view of the typical compounds already described, in more typical embodiments the invention relates to a compound comprising one of the following formulae:

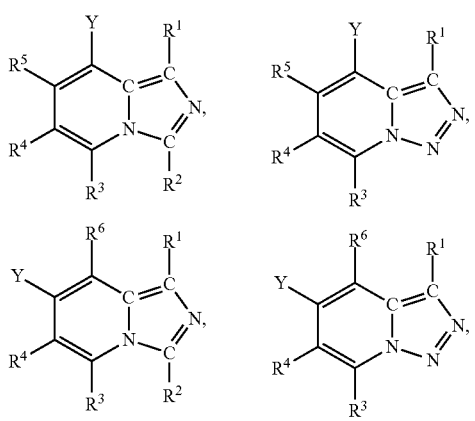

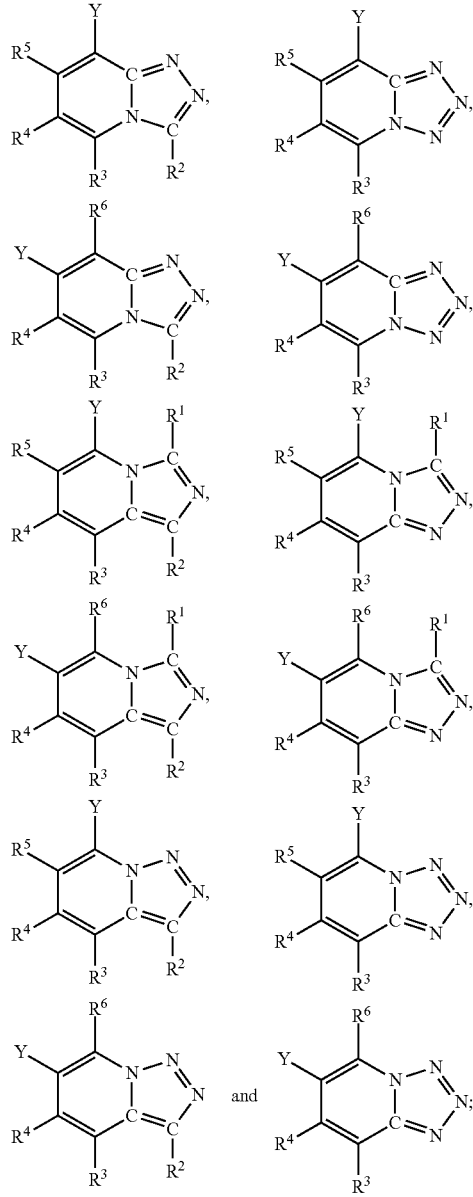

preferably wherein the compound comprises one of the following formulae:

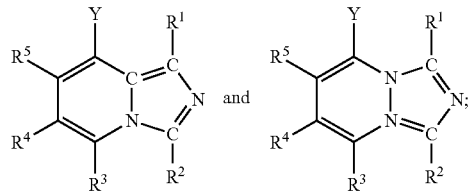

wherein, in each case, the substituents Y and R are as defined in any of the above or below embodiments described herein.

Furthermore, in view of the typical compounds already described, in more typical embodiments the invention relates to a compound comprising one of the following formulae:

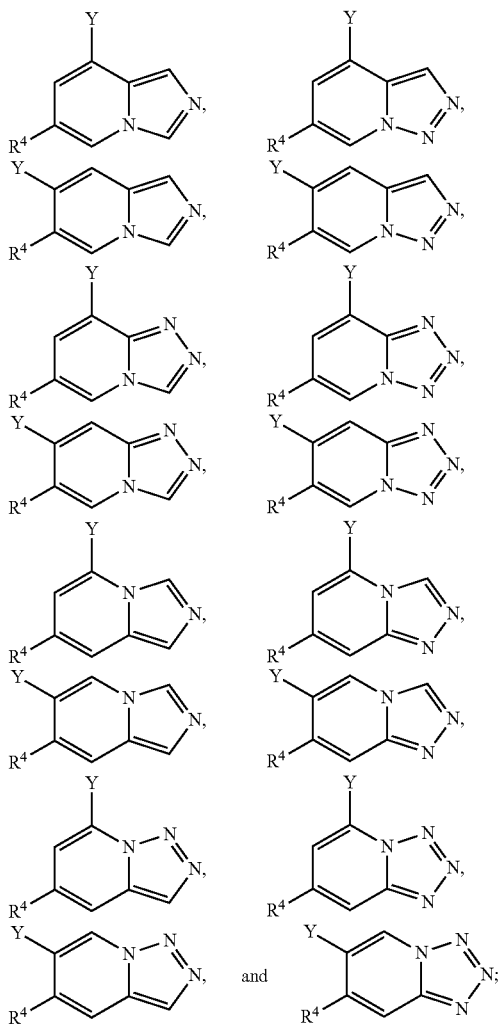

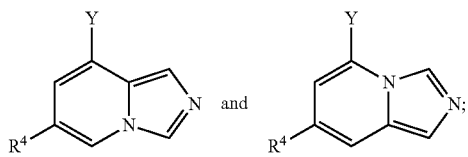 and wherein, in each case, the substituents Y and R⁴ are as defined in any of the above or below embodiments described herein, preferably wherein R⁴ is selected from H, a halogen (such as —F, —Cl and Br), a substituted or unsubstituted $C_1$-$C_6$ alkyl group (such as a —$CF_3$ group), a substituted or unsubstituted $C_3$-$C_6$ cycloalkyl group (such as a cyclopropyl group), a substituted or unsubstituted $C_1$-$C_6$ alkoxy group, and a nitrile group, and more typically wherein R⁴ is not H; preferably wherein the compound has one of the following formulae:

wherein, in each case, the substituents Y and R⁴ are as defined in any of the above or below embodiments described herein, preferably wherein R⁴ is selected from H, a halogen (such as —F, —Cl and Br), a substituted or unsubstituted $C_1$-$C_6$ alkyl group (such as a —$CF_3$ group), a substituted or unsubstituted $C_3$-$C_6$ cycloalkyl group (such as a cyclopropyl group), a substituted or unsubstituted $C_1$-$C_6$ alkoxy group, and a nitrile group, and more typically wherein R⁴ is not H.

Furthermore, in view of the typical compounds already described, in more typical embodiments the invention relates to a compound comprising one of the following formulae:

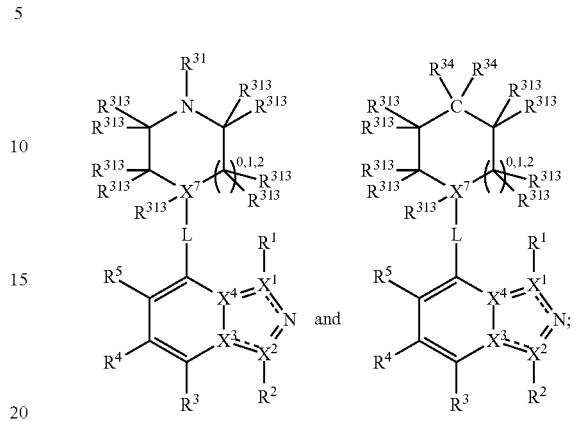

wherein, in each case, the substituents X, L and R are as defined in any of the above or below embodiments described herein, and L may be present or absent.

Furthermore, in view of the typical compounds already described, in more typical embodiments the invention relates to a compound comprising one of the following formulae:

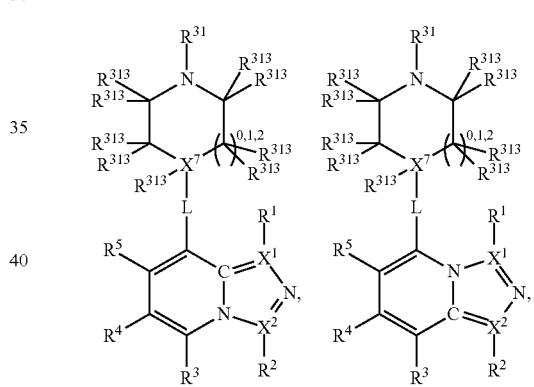

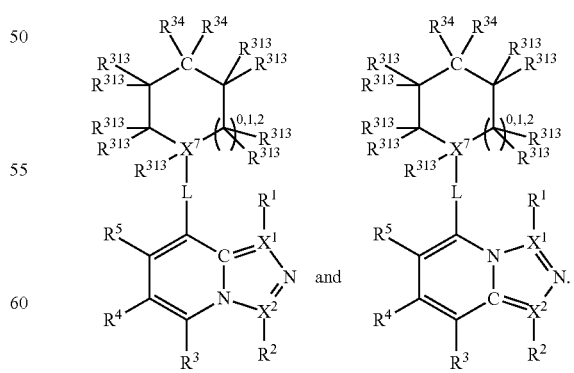

wherein, in each case, the substituents X, L and R are as defined in any of the above or below embodiments described herein, and L may be present or absent.

Furthermore, in view of the typical compounds already described, in more typical embodiments the invention relates to a compound comprising one of the following formulae:

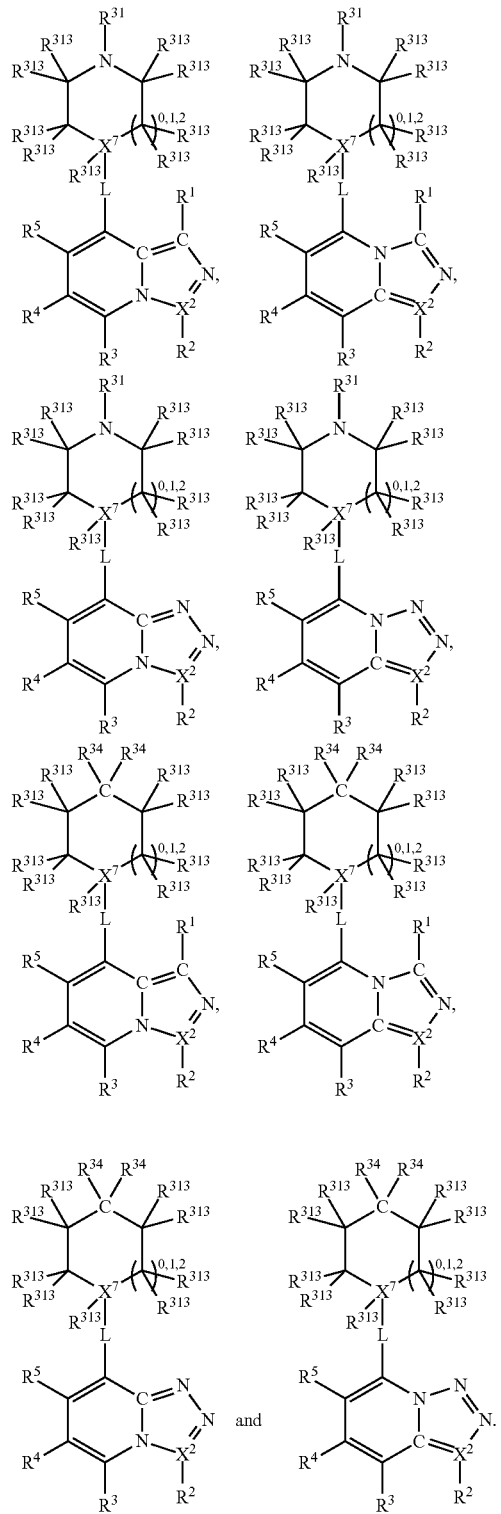

preferably wherein the compound has one of the following formulae:

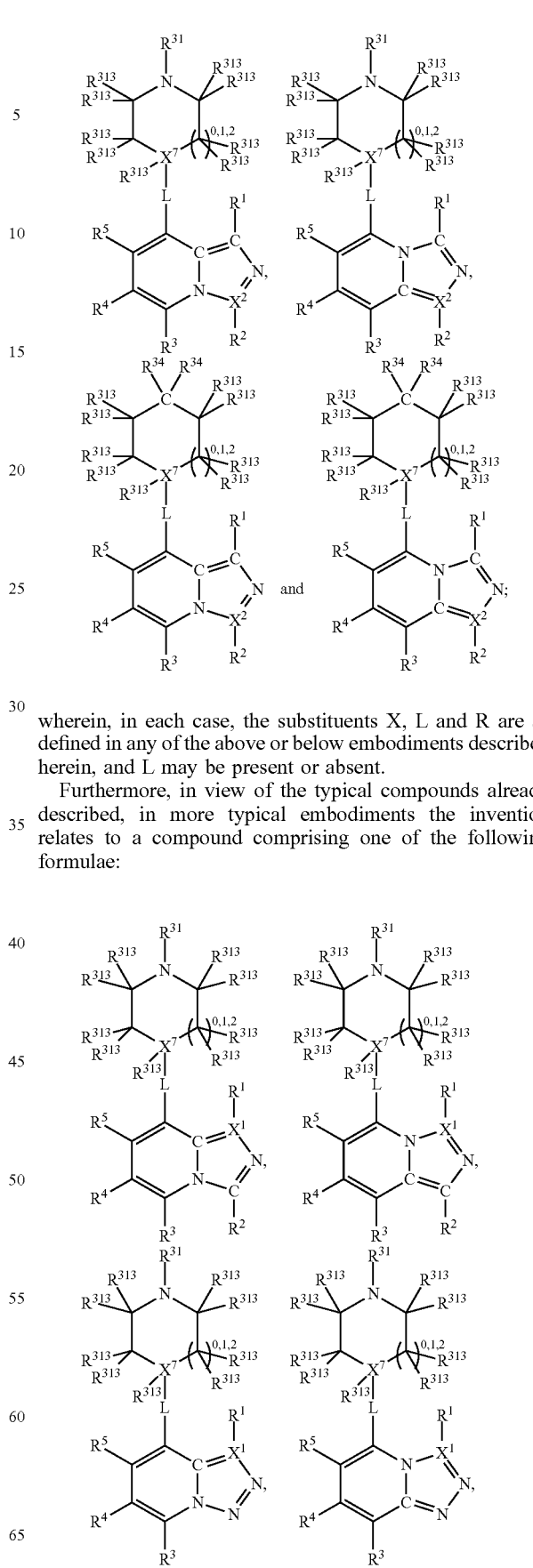

wherein, in each case, the substituents X, L and R are as defined in any of the above or below embodiments described herein, and L may be present or absent.

Furthermore, in view of the typical compounds already described, in more typical embodiments the invention relates to a compound comprising one of the following formulae:

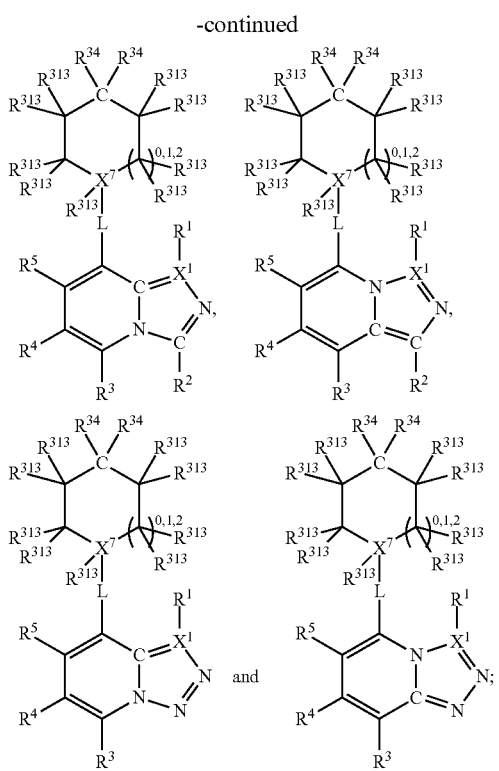

preferably wherein the compound has one of the following formulae:

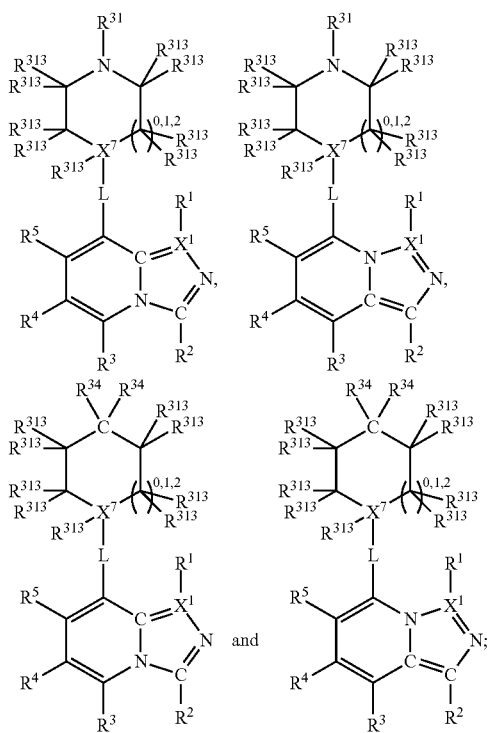

and wherein, in each case, the substituents X, L and R are as defined in any of the above or below embodiments described herein, and L may be present or absent.

Furthermore, in view of the typical compounds already described, in more typical embodiments the invention relates to a compound comprising one of the following formulae:

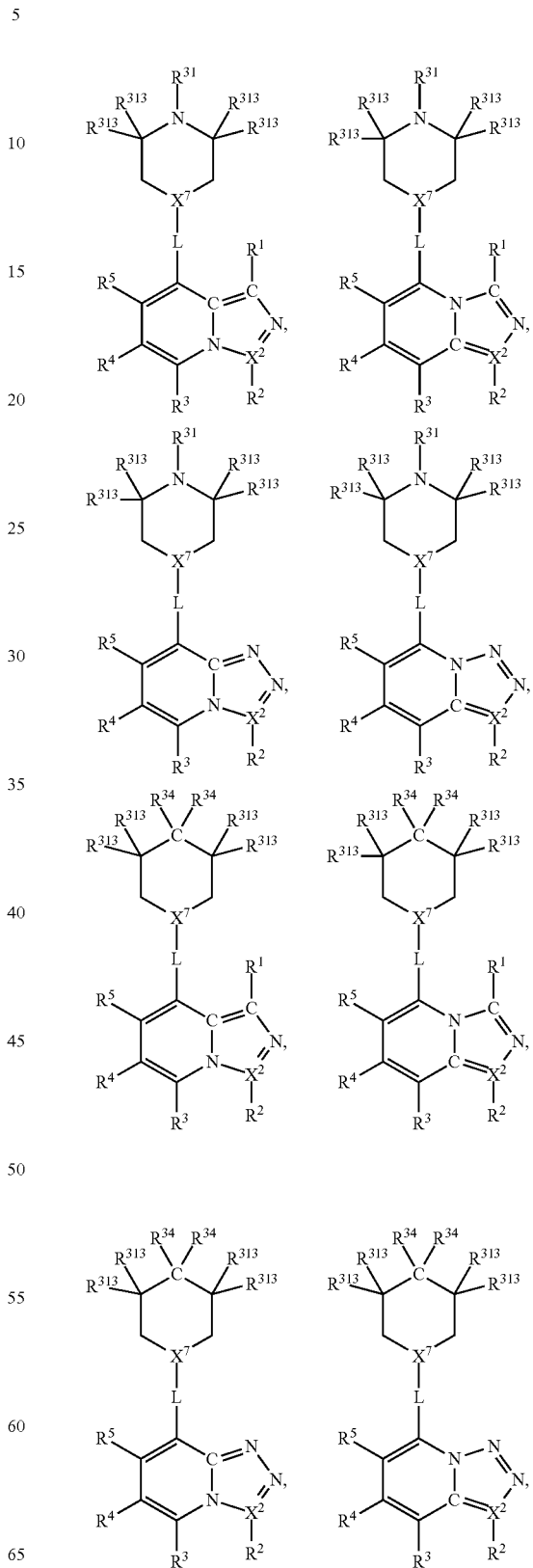

-continued

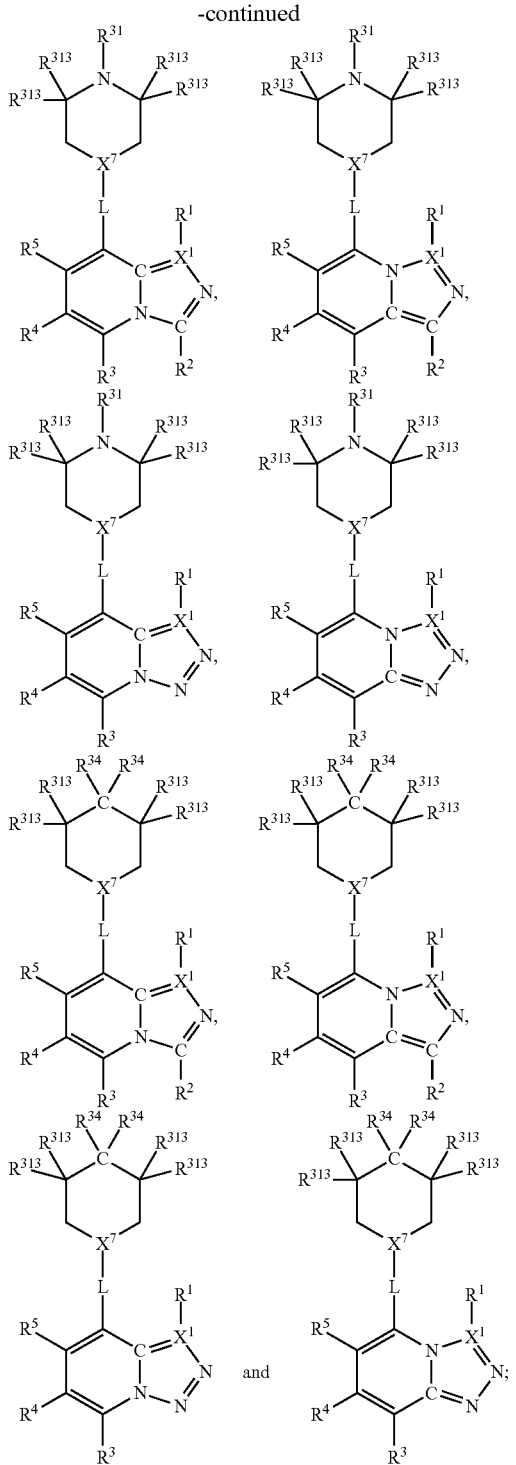

wherein, in each case, the substituents X, L and R are as defined in any of the above or below embodiments described herein, and L may be present or absent.

The Y, R and X groups in all of the compounds and structures both above and below herein will now be described in more detail.

As has been mentioned, the number of R substituents on an X or a ring atom will depend on its valency. Thus, it will be apparent in all of the embodiments of the invention, both above and below, that an X will have no substituents if it is N with a double bond, and 1 substituent (H or an organic group as defined herein) if it is N with a single bond or C with a double bond.

As has been mentioned, in all of the embodiments of this invention (both above and below herein), the substituent is not especially limited, provided that it does not prevent the TDO or IDO inhibitory function from occurring. However, in typical embodiments, the substituents may be selected independently as follows.

$R^1$ and $R^2$ are typically each independently selected from H and a group selected from the following groups:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched $C_1$-$C_6$ halogenated alkyl group (such as —CH$_2$F, —CF$_3$, and —CH$_2$CF$_3$);

an —NH$_2$ group, or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, —NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph, a substituted or unsubstituted cyclic $C_3$-$C_8$ alkyl group (such as cyclopropyl, cyclobutyl, cyclopentyl, cyclohexyl, cycloheptyl and cyclooctyl);

an —OH or a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$O H, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched $C_1$-$C_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxy-propan-2-yl; —(CO)NH$_2$, —(CO)NHMe, —(CO)NMe$_2$, —(CO)NHE, —(CO)NEt$_2$, —(CO)-pyrollidine-N-yl, —(CO)-morpholine-N-yl, —(CO)- piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched C$_1$-C$_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched C$_1$-C$_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted linear or branched C$_1$-C$_7$ amino carbonyl group (such as —NH—CO-Me, —NH—CO-Et, —NH—CO—Pr, —NH—CO—Bu, —NH—CO-pentyl, —NH—CO-hexyl, —NH—CO-Ph, —NMe-CO-Me, —NMe-CO-Et, —NMe-CO—Pr, —NMe-CO—Bu, —NMe-CO-pentyl, —NMe-CO-hexyl, —NMe-CO-Ph;

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 of 4)-Cl-Ph, —CH$_3$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched amino-alkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$— cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO2-pyrrolidine-N-yl, —SO$_2$-morpholine-N-yl, —SO$_2$NHCH$_2$OMe, and —SO$_2$NHCH$_2$CH$_2$OMe;

an substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)- Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

$R^3$, $R^4$, $R^5$, $R^6$ and $R^{313}$ are typically each independently selected from H and a group selected from the following groups:

a halogen (such as —F, —Cl, —Br and —I);

a nitrile group;

a substituted or unsubstituted linear or branched C$_1$-C$_6$ alkyl group (such as Me, Et, Pr, i-Pr, n-Bu, i-Bu, t-Bu, pentyl and hexyl);

a substituted or unsubstituted linear or branched C$_1$-C$_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched C$_1$-C$_6$ halogenated alkyl group (such as —CH$_2$F, —CH$_2$Cl, —CF$_3$, —CCl$_3$—CBr$_3$, —CI$_3$, —CH$_2$CF$_3$, —CH$_2$CCl$_3$, —CH$_2$CBr$_3$, and —CH$_2$CI$_3$);

an —NH$_2$ group, or a substituted or unsubstituted linear or branched primary secondary or tertiary C$_1$-C$_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic C$_3$-C$_8$ alkyl group (such as cyclopropyl, cyclobutyl, cyclopentyl, cyclohexyl, cycloheptyl and cyclooctyl);

an —OH or a substituted or unsubstituted linear or branched C$_1$-C$_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_1$-C$_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched C$_1$-C$_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched C$_1$-C$_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted linear or branched C$_1$-C$_7$ amino carbonyl group (such as —NH—CO-Me, —NH—CO-Et, —NH—CO—Pr, —NH—CO—Bu, —NH—CO-pentyl, —NH—CO-hexyl, —NH—CO-Ph, —NMe-CO-Me, —NMe-CO-Et, —NMe-CO—Pr, —NMe-CO—Bu, —NMe-CO-pentyl, —NMe-CO-hexyl, —NMe-CO-Ph;

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO2-pyrolidine-N-yl, —SO$_2$-morpholine-N-yl, —SO$_2$NHCH$_2$OMe, and —SO$_2$NHCH$_2$CH$_2$OMe;

an substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)- Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);

a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl); and where there are two R$^{313}$ groups attached to the same atom, they may together form a group which is double bonded to that atom, (such as a carbonyl group (=O) or an alkene group (=C(R')$_2$) wherein each R' group is the same or different and is H or an organic group, preferably H or a straight or branched C$_1$-C$_6$ alkyl group), or the two R$^{313}$ groups on the same atom may form a ring, preferably a substituted or unsubstituted C$_3$-C$_6$ saturated carbocyclic ring together with the atom to which they are attached (such as a substituted or unsubstituted cyclopropyl ring or a substituted or unsubstituted cyclobutyl ring), this being more preferable when the two R$^{313}$ groups are on an atom adjacent to the N—R$^{31}$, (or adjacent to the (C—R$^{34}$) and/or adjacent to the X$^7$.

More typically, where present, R$^1$ and R$^2$ are independently selected from H, a substituted or unsubstituted C$_1$-C$_6$ alkyl group, an —NH$_2$ group and a substituted or unsubstituted C$_1$-C$_6$ amino group, and a substituted or unsubstituted C$_1$-C$_6$ alkoxy group. Most typically, R$^1$ and R$^2$ are both H. More typically, where present R$^3$, R$^5$ and R$^6$ are independently selected from H, a halogen (such as —F, —Cl and —Br) a substituted or unsubstituted C$_1$-C$_6$ alkyl group (such as a —CF$_3$ group), an —NH$_2$ group and a substituted or unsubstituted C$_1$-C$_6$ amino group, a substituted or unsubstituted C$_1$-C$_6$ alkoxy group, and a nitrile group. More typically, R$^4$ is selected from H, a halogen (such as —F, —Cl and Br), a substituted or unsubstituted C$_1$-C$_6$ alkyl group (such as a —CF$_3$ group), a substituted or unsubstituted C$_3$-C$_6$ cycloalkyl group (such as a cyclopropyl group), a substituted or unsubstituted $C_1$-$C_6$ alkoxy group, and a nitrile group, and further typically $R^4$ is not H. More typically each $R^{313}$ is selected from H, a halogen (such as —F and —Cl) a substituted or unsubstituted $C_1$-$C_6$ alkyl group, an —$NH_2$ group and a substituted or unsubstituted $C_1$-$C_6$ amino group, a substituted or unsubstituted $C_1$-$C_6$ alkoxy group, a nitrile group, a substituted or unsubstituted aromatic or aliphatic cyclic group (such as a carbocyclic group or a heterocyclic group, such as a substituted or unsubstituted phenyl group). Typically when two $R^{313}$ groups on the same atom form a ring, it is a $C_3$-$C_6$ saturated carbocyclic ring such as a cyclopropyl ring or a cyclobutyl ring. In certain embodiments, where present (and not a group Y) all of $R^1$, $R^2$, $R^3$, $R^4$, $R^5$, $R^6$ and $R^{313}$ are H, or one of $R^1$, $R^2$, $R^3$, $R^4$, $R^5$ and $R^6$ that is not Y (preferably $R^4$) is not H and all of $R^{313}$ are H.

As has been mentioned the group Y has one of the following formulae:

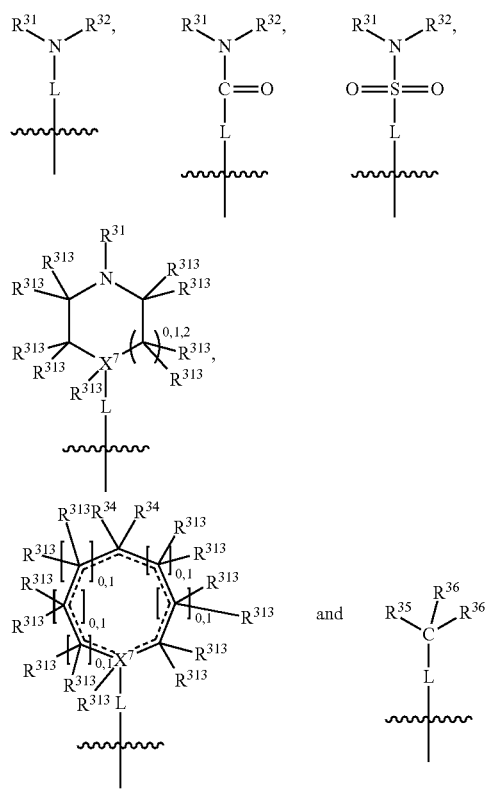

wherein L may be present or absent, and may be any substituted or unsubstituted organic linking group; $R^{31}$ and $R^{32}$ may be the same or different and are selected from H and a substituted or unsubstituted organic group; each $R^{34}$ may be the same or different and is selected from H and a substituted or unsubstituted organic group; $R^{35}$ is selected from a substituted or unsubstituted alcohol group or ether group; each $R^{36}$ may be the same or different and is selected from H and a substituted or unsubstituted organic group; $X^7$ is selected from C and N; each bond represented by a dotted line in the group shown as an eight-membered ring may be present or absent; and each $R^{313}$ may be the same or different and is selected from H and a substituted or unsubstituted organic group.

The following Y group:

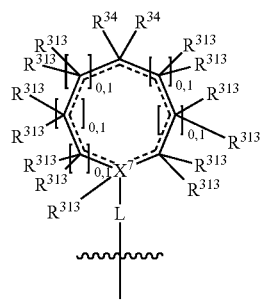

is more typically a group having one of the following formulae:

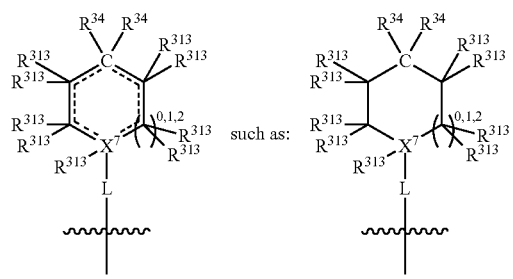

and more typically a group having one of the following formulae:

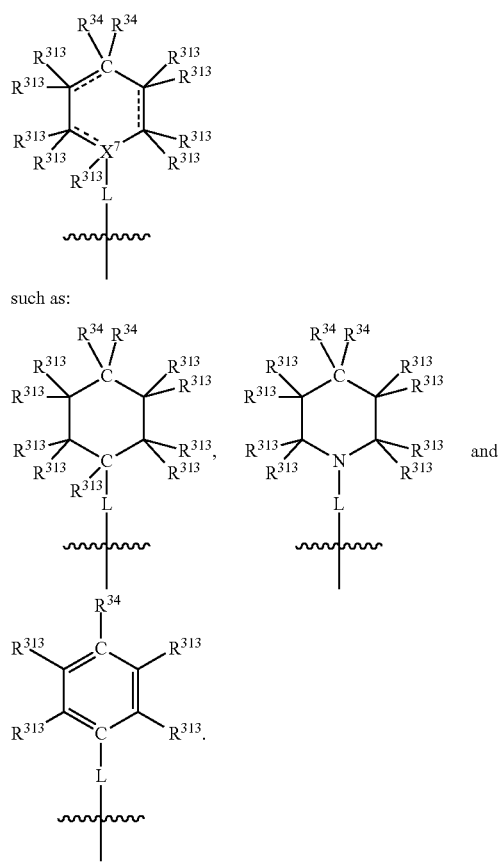

In the present context, any group may be a linking group provided that it is capable of joining the ring system to the rest of the Y group. Typically the linking group is divalent, but may be trivalent or tetravalent in some embodiments.

In some typical embodiments, $R^{32}$ is H:

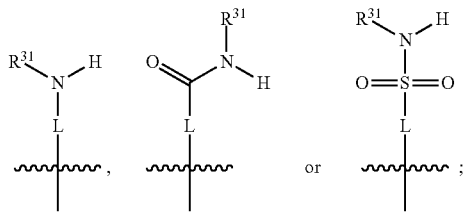

or $R^{31}$ is H:

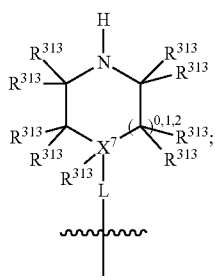

or at least one $R^{34}$ is H:

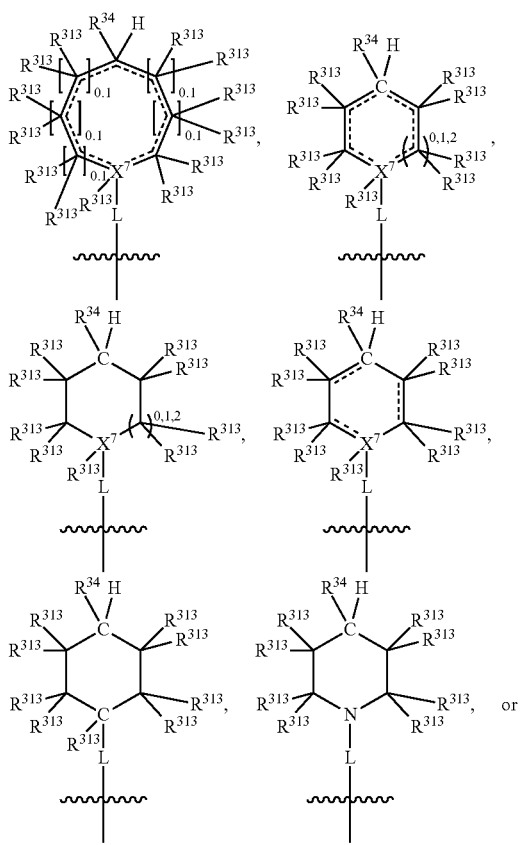

-continued

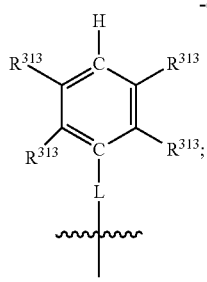

or one or both of $R^{36}$ is H:

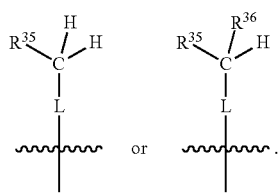

In typical embodiments there is one Y group present, but it is not excluded that a plurality of Y groups may be present in some cases, such as 2 or more Y groups, or 3 or more Y groups, or 4 or more Y groups. Provided that at lease one of $R^5$ and $R^6$ is Y, any one or more of $R^3$, $R^4$, $R^5$ and $R^6$ may comprise the further group Y. Thus, $R^3$ may comprise a Y group. $R^4$ may comprise a Y group. $R^5$ may comprise a Y group. $R^6$ may comprise a Y group. In all embodiments above and below herein, it is preferred that $R^6$ comprises the Y group.

As has been mentioned, in typical embodiments, the group L may be present or absent. When present L is a linker group attaching Y to the ring system. L is not especially limited, provided that the function of the molecule is not impaired. Accordingly, any known linking groups in organic chemistry may be employed. Typically L is a divalent group, suitable for linking the ring system to the group Y. In such embodiments L may, for example, comprise a substituted or unsubstituted $C_1$-$C_7$ alkylene group (such as —$CH_2$—, —$CH_2CH_2$—, —$CH_2CH_2CH_2$—, —$CH(CH_3)CH_2$—, —$C(CH_3)_2$—, —$CH_2CH_2CH_2CH_2$—, —$CH(CH_3)$ $CH_2CH_2$—, —$CH(CH_3)CH(CH_3)$—, —$CH(CH_2CH_3)$ $CH_2$—, —$C(CH_3)_2CH_2$—, —$CH_2CH_2CH_2CH_2CH_2$—, and —$CH_2CH_2CH_2CH_2CH_2CH_2$—), or a $C_1$-$C_7$ divalent alkoxy group (such as —$OCH_2$—, —$OCH_2CH_2$—, —$OCH_2CH_2CH_2$—, —O—$CH(CH_3)CH_2$—, —$OC(CH_3)_2$—, —$OCH_2CH_2CH_2CH_2$—, —$OCH(CH_3)$ $CH_2CH_2$—, —$OCH(CH_3)CH(CH_3)$—, —$OCH(CH_2CH_3)$ $CH_2$—, —$OC(CH_3)_2CH_2$—, —$OCH_2CH_2CH_2CH_2CH_2$—, —$OCH_2CH_2CH_2CH_2CH_2CH_2$—, —$OCHF$—, —$OCF_2$—, —O-phenylene-, —O—$CH_2$-phenylene-, —O—$CH_2$-(2,3 or 4)-F-phenylene-, —O—$CH_2$-(2,3 or 4)-Cl-phenylene-, —$CH_2OCH_2$—, —$CH_2OCH_2CH_2$—, —$CH_2OCH_2CH_2CH_2$—, —$CH_2OCH_2CH_2CH_2$—, —$CH_2CH_2OCH_2$—, —$CH_2CH_2CH_2OCH_2$—, —$CH_2CH_2CH_2CH_2OCH_2$—, —$CH_2CH_2CH_2CH_2CH_2OCH_2$—, —$CH_2CH_2CH_2CH_2CH_2CH_2OCH_2$—, —$CH_2CH_2OCH_2CH_2$—, —$CH_2CH_2OCH_2CH_2CH_2$—, —$CH_2CH_2OCH_2CH_2CH_2CH_2$—, —$CH_2CH_2OCH_2CH_2CH_2CH_2CH_2$—, —$CH_2CH_2CH_2OCH_2CH_2$—, —$CH_2CH_2CH_2OCH_2CH_2CH_2$—, and —CH$_2$CH$_2$CH$_2$OCH$_2$CH$_2$CH$_2$CH$_2$—. Alternatively, L may be an —O— atom, or an —N(R$^{32}$)— group (such as an —NH— group).

The group Y typically comprises an aminocarbonyl group, a carbonylamino group, an aminosulphonyl group, a sulphonylamino group, a substituted or unsubstituted piperidinyl group a substituted or unsubstituted piperazinyl group, a substituted or unsubstituted alcohol group, a substituted or unsubstituted ether group, and/or a saturated or unsaturated, substituted or unsubstituted, carbocyclic group such as a substituted or unsubstituted cyclohexyl group or a substituted or unsubstituted phenyl group. Typically the N atom in the above formula for Y forms the amino part of these groups, although it is not excluded that the N atom is not the amino part of these groups.

In one embodiment, L is absent, and Y is selected from the following groups:

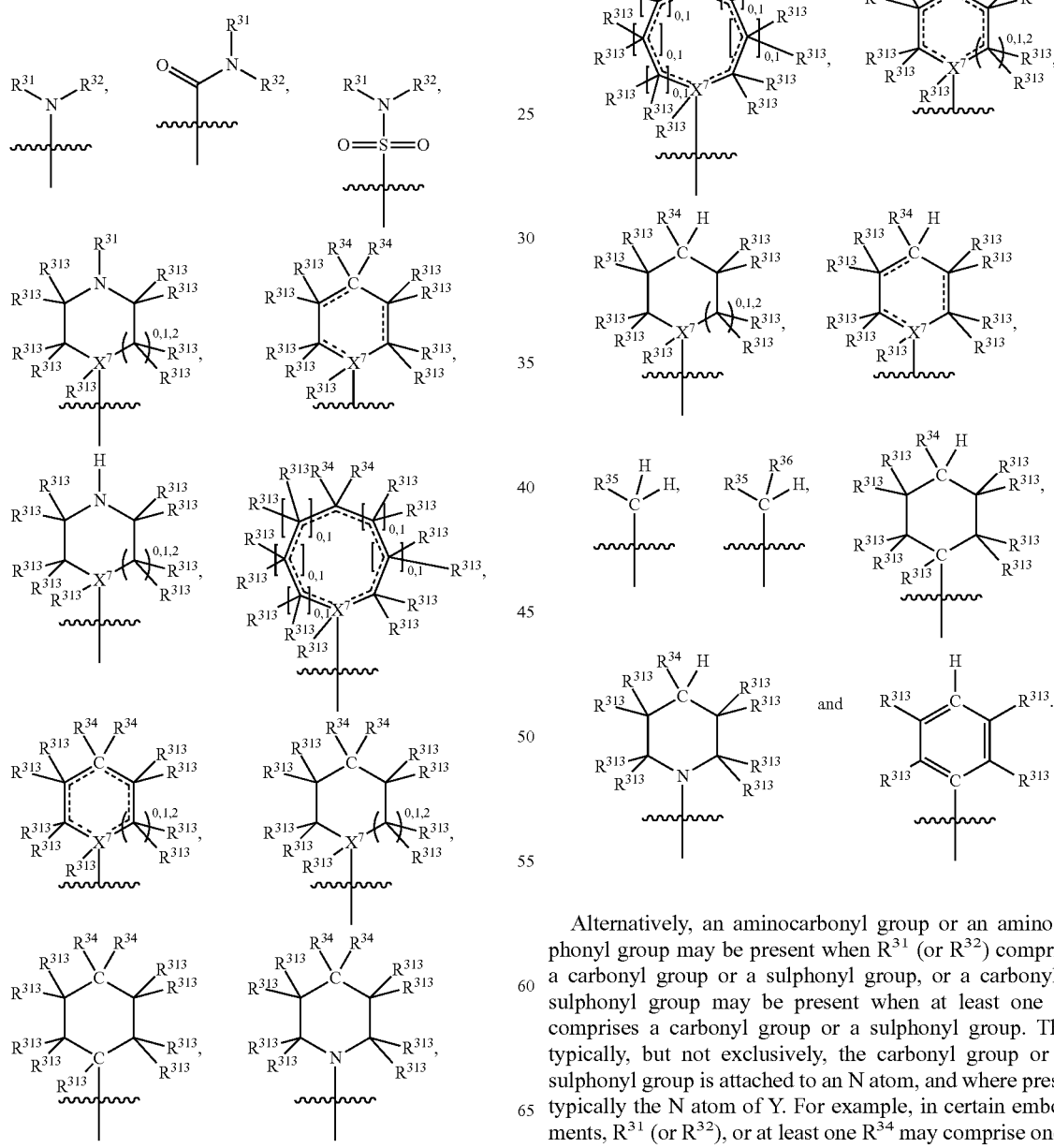

Alternatively, an aminocarbonyl group or an aminosulphonyl group may be present when R$^{31}$ (or R$^{32}$) comprises a carbonyl group or a sulphonyl group, or a carbonyl or sulphonyl group may be present when at least one R$^{34}$ comprises a carbonyl group or a sulphonyl group. Thus, typically, but not exclusively, the carbonyl group or the sulphonyl group is attached to an N atom, and where present typically the N atom of Y. For example, in certain embodiments, R$^{31}$ (or R$^{32}$), or at least one R$^{34}$ may comprise one of the following groups:

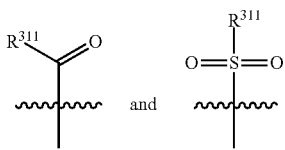

In the case of $R^{34}$, it will be appreciated from the foregoing that in some instances an N atom is not present. However, in other instances an N may be present so as to form an aminocarbonyl or an aminosulphonyl group. Furthermore, in the case of $R^{34}$ a further carbon atom (which may be substituted or unsubstituted) may be present between the aminocarbonyl (or aminosulphonyl) group and the ring. Thus, $R^{34}$ may in some cases comprise a group having one of the following formulae:

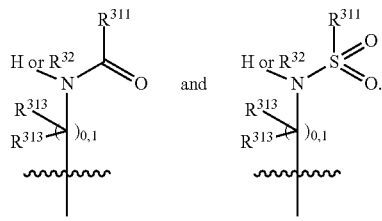

In the above formulae, $R^{311}$ is selected from H and a substituted or unsubstituted organic group. In some instances, the N(H or $R^{32}$) group in these groups may be absent such that $R^{34}$ may in some cases comprise a group having one of the following formulae:

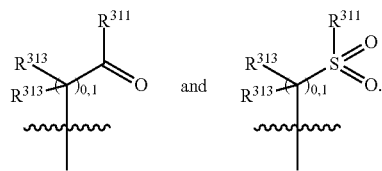

Accordingly, the Y group is typically selected from the following:

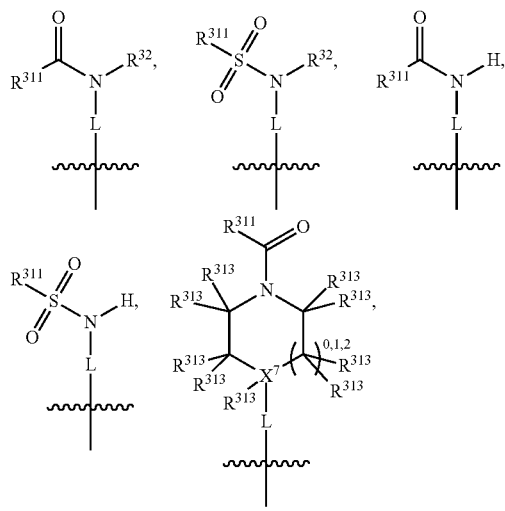

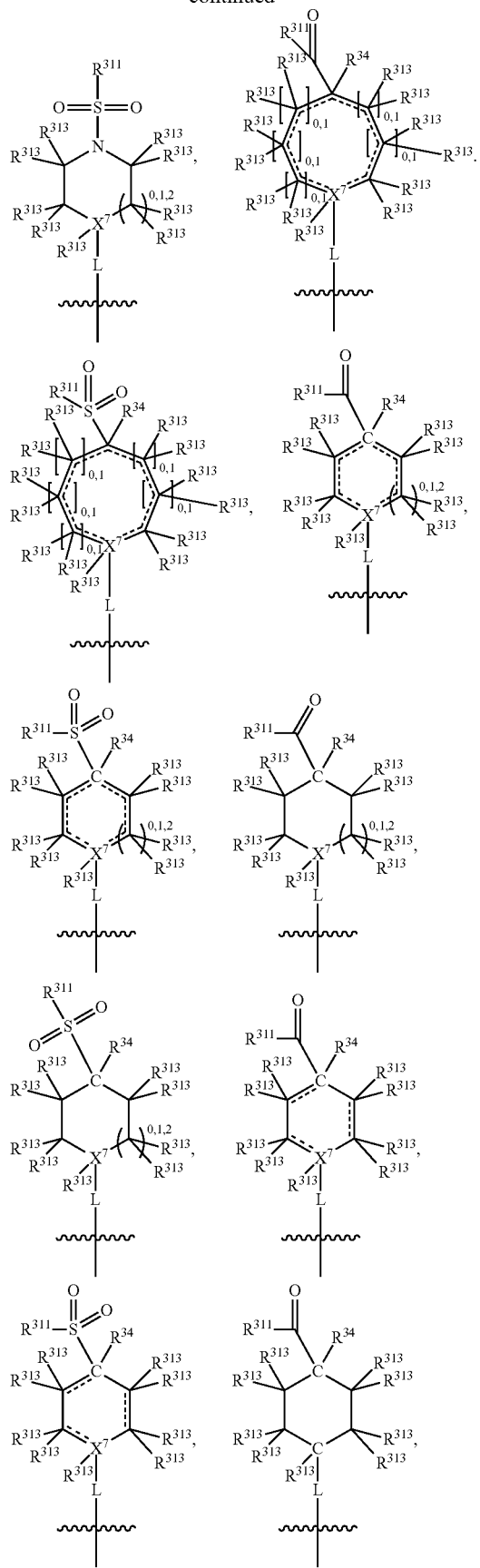

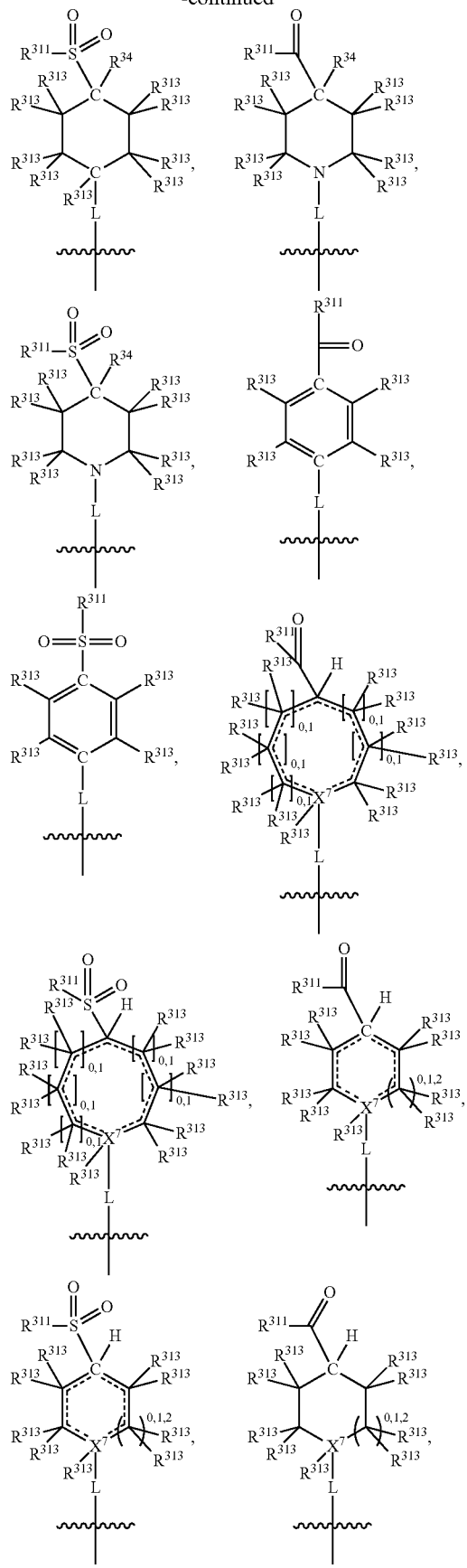
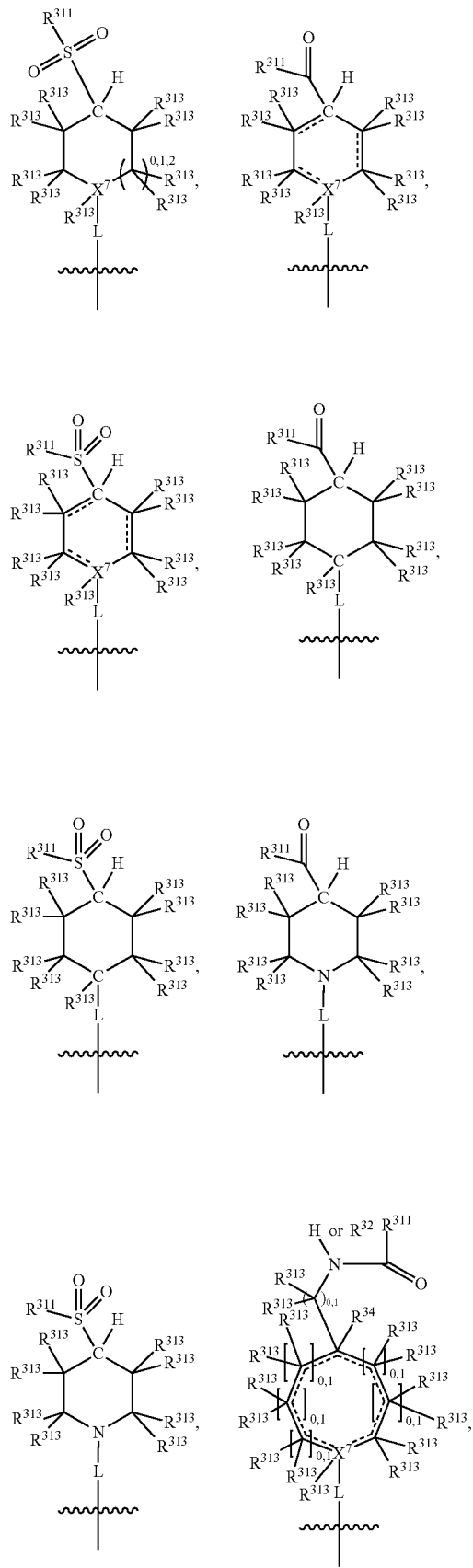

-continued
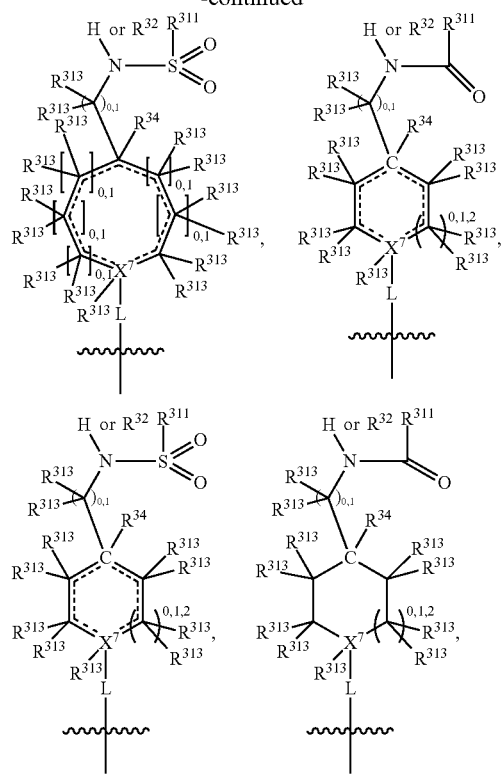
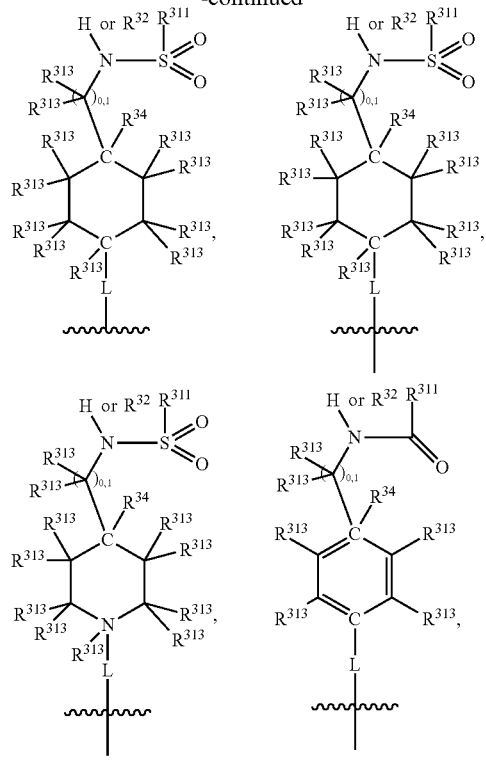
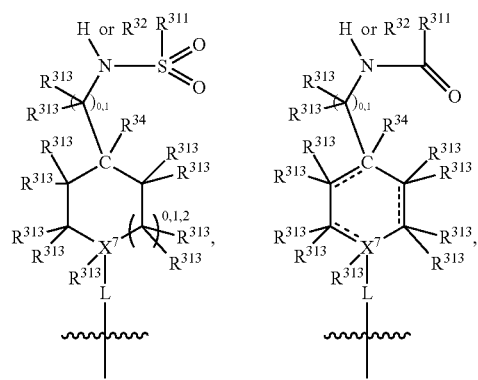
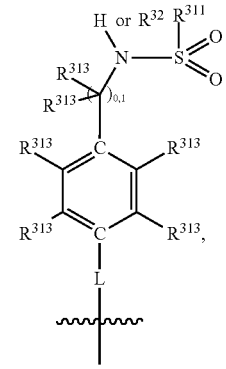
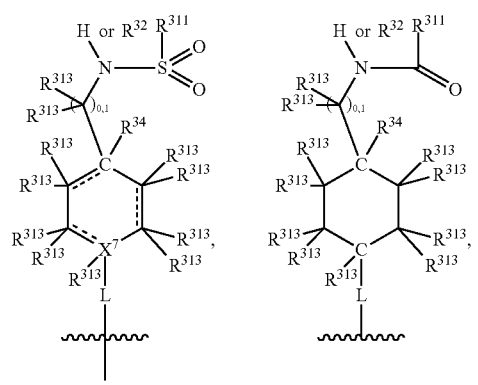
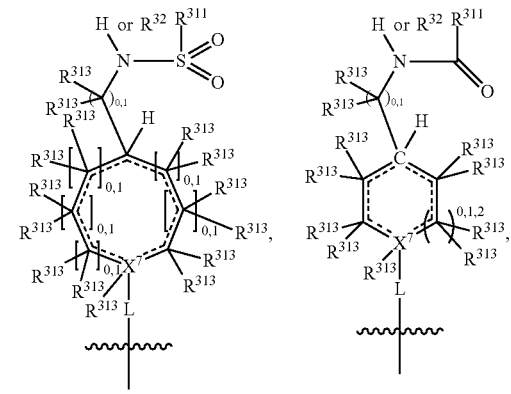

-continued

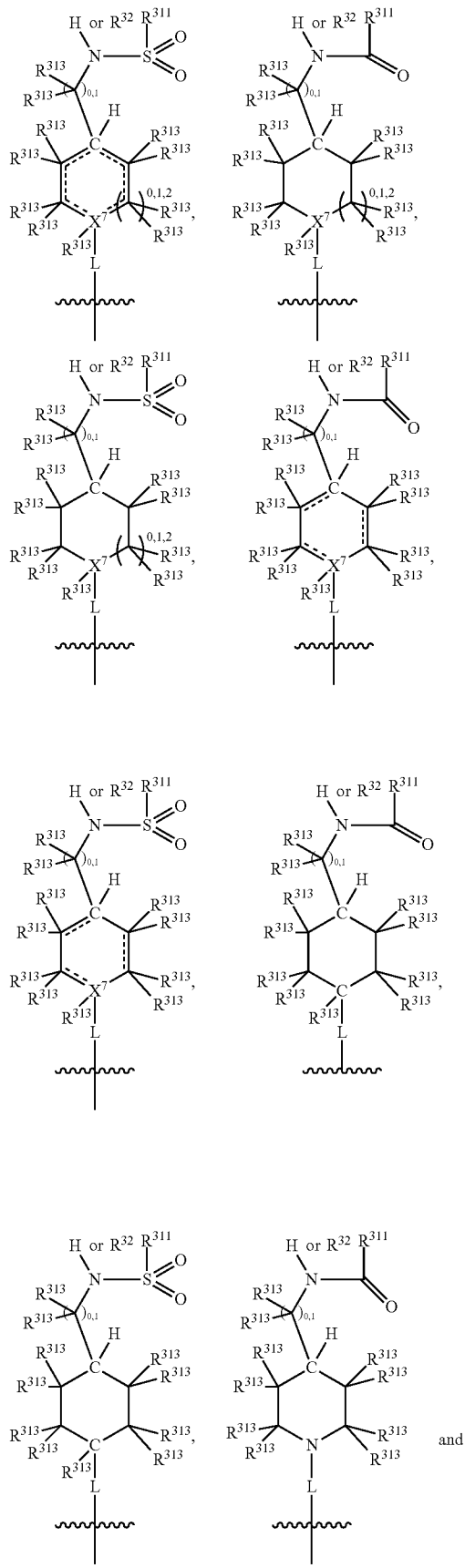

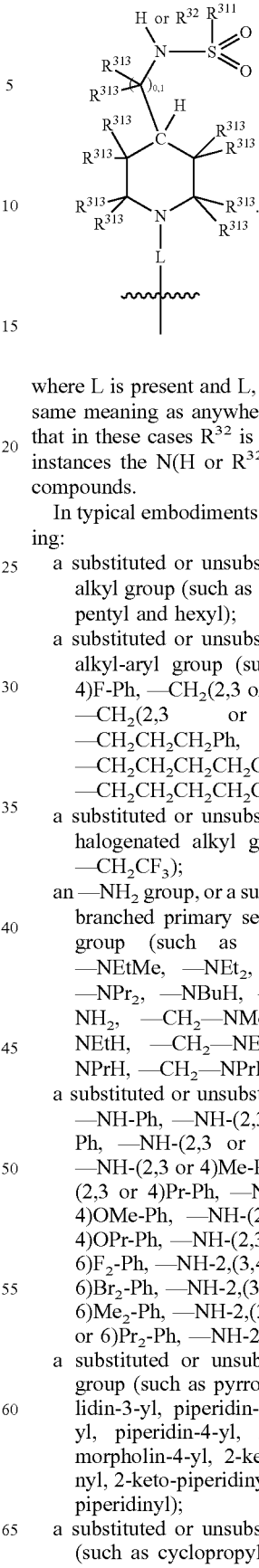

where L is present and L, $R^{32}$, $R^{34}$, $R^{311}$ and $R^{313}$ have the same meaning as anywhere above or below herein, except that in these cases $R^{32}$ is not H and $R^{34}$ is not H. In some instances the N(H or $R^{32}$) group may be absent in these compounds.

In typical embodiments, $R^{311}$ is selected from the following:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched $C_1$-$C_6$ halogenated alkyl group (such as —CH$_2$F, —CF$_3$, —CH$_2$CF$_3$);

an —NH$_2$ group, or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5 or 6)Pr$_2$-Ph, —NH-2,(3,4,5 or 6)Bu$_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted linear or branched $C_1$-$C_6$ alcohol group (such as —$CH_2OH$, —$CH_2CH_2OH$, —$CH_2CH_2CH_2OH$, —$CH(CH_3)CH_2OH$, —$C(CH_3)_2OH$, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)_2CH_2OH$, —$CH_2CH_2CH_2CH_2CH_2OH$, and —$CH_2CH_2CH_2CH_2CH_2CH_2OH$);

a substituted or unsubstituted linear or branched $C_1$-$C_7$ amino carbonyl group (such as —NH—CO-Me, —NH—CO-Et, —NH—CO—Pr, —NH—CO—Bu, —NH—CO-pentyl, —NH—CO-hexyl, —NH—CO-Ph, —NMe-CO-Me, —NMe-CO-Et, —NMe-CO—Pr, —NMe-CO—Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —$OCH_2F$, —$OCHF_2$, —$OCF_3$, —O-Ph, —O—$CH_2$-Ph, —O—$CH_2$-(2,3 or 4)-F-Ph, —O—$CH_2$-(2,3 or 4)-Cl-Ph, —$CH_2OMe$, —$CH_2OEt$, —$CH_2OPr$, —$CH_2OBu$, —$CH_2CH_2OMe$, —$CH_2CH_2CH_2OMe$, —$CH_2CH_2CH_2CH_2OMe$, and —$CH_2CH_2CH_2CH_2CH_2OMe$);

a substituted or unsubstituted linear or branched aminoalkoxy group (such as —$OCH_2CH_2NH_2$, —$OCH_2CH_2NHMe$, —$OCH_2CH_2NMe_2$, —$OCH_2CH_2NHEt$, and —$OCH_2CH_2NEt_2$;

a substituted or unsubstituted aminosulphonyl group (such as —$NHSO_2Me$, —$NHSO_2Et$, —$NHSO_2Pr$, —$NHSO_2iPr$, —$NHSO_2Ph$, —$NHSO_2$-(2,3 or 4)-F-Ph, —$NHSO_2$-cyclopropyl, —$NHSO_2CH_2CH_2OCH_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-$I_2$-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)- $Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-, 4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-);

a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

In more preferred embodiments, $R^{311}$ is selected from the following:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph);

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-$I_2$-Ph-, 2,(3, 4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)- $Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-, 4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-);

a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

In these cases, typically L does not comprise a carbonyl or a sulphonyl, although this is not excluded.

In typical embodiments, the linker L is absent. In such cases, Y may be selected from any of the following:

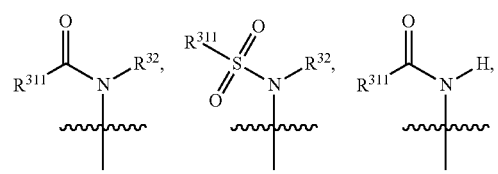

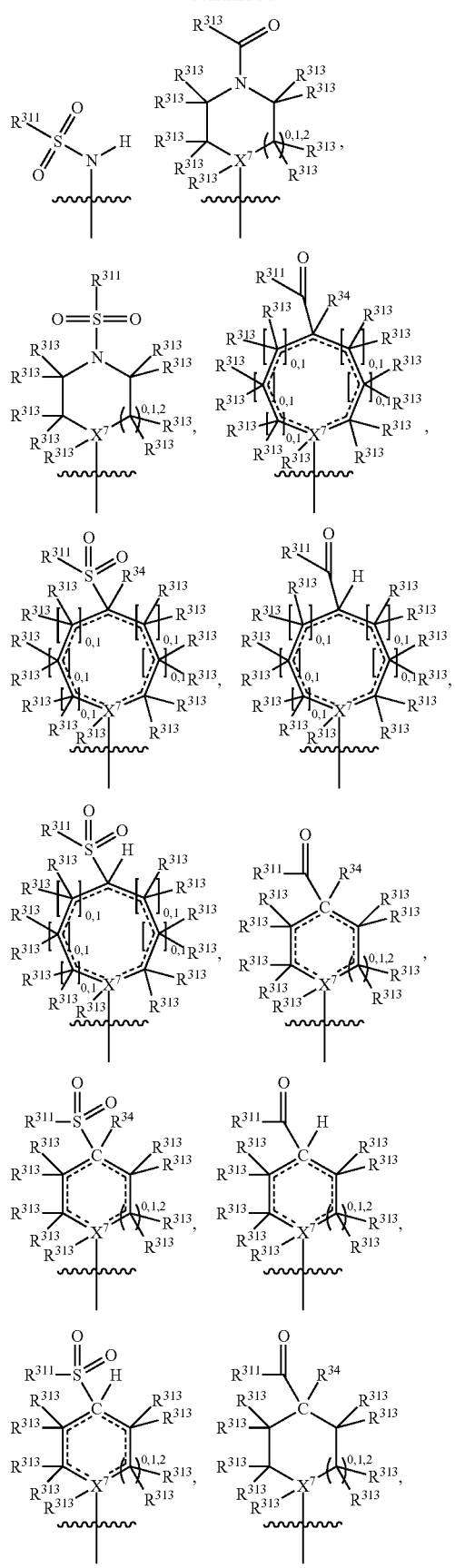
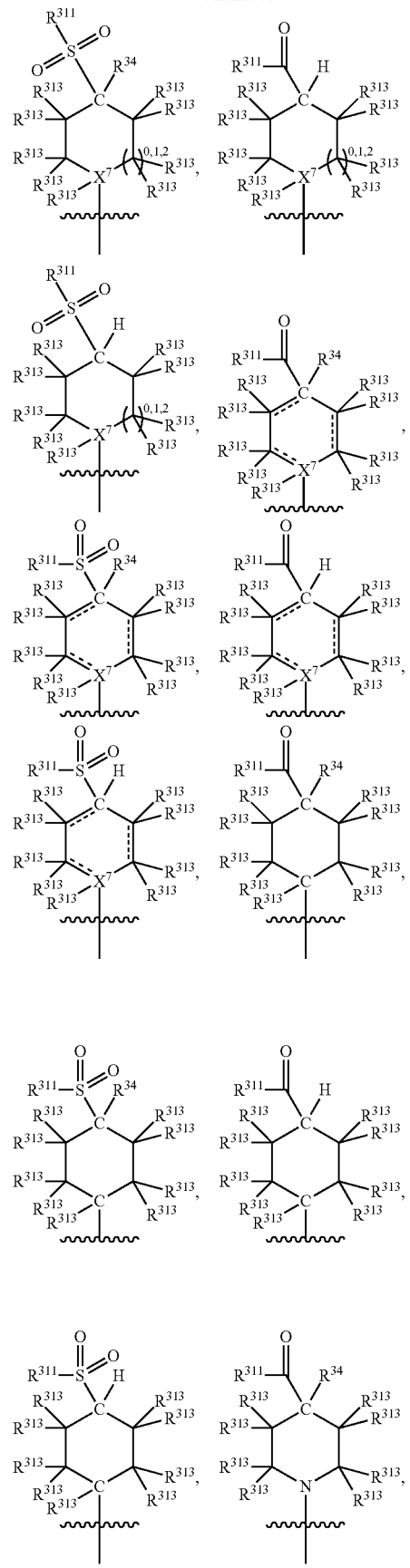

-continued
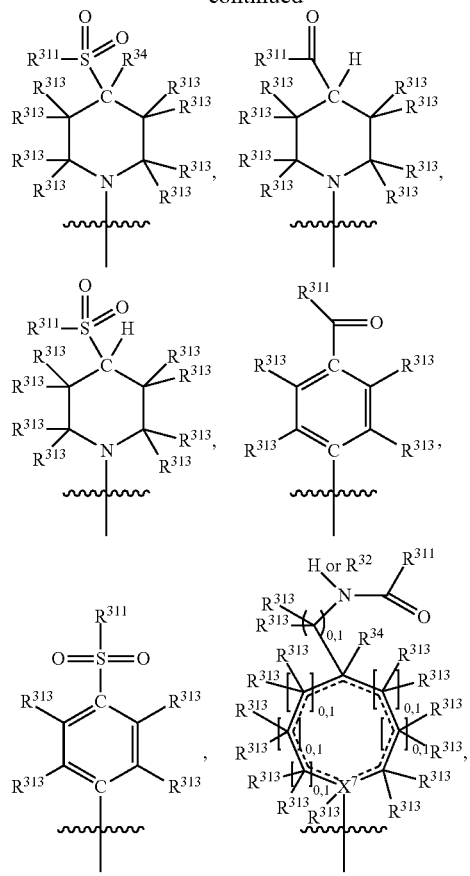
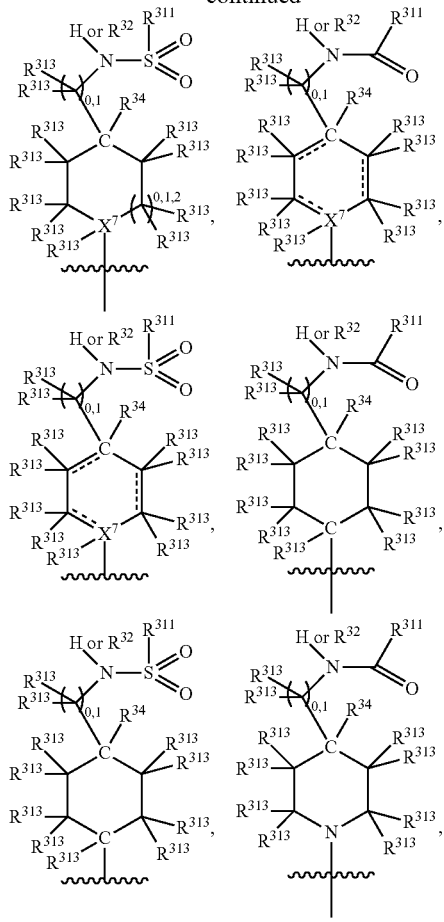
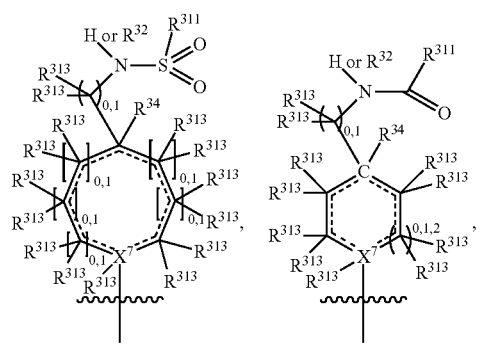
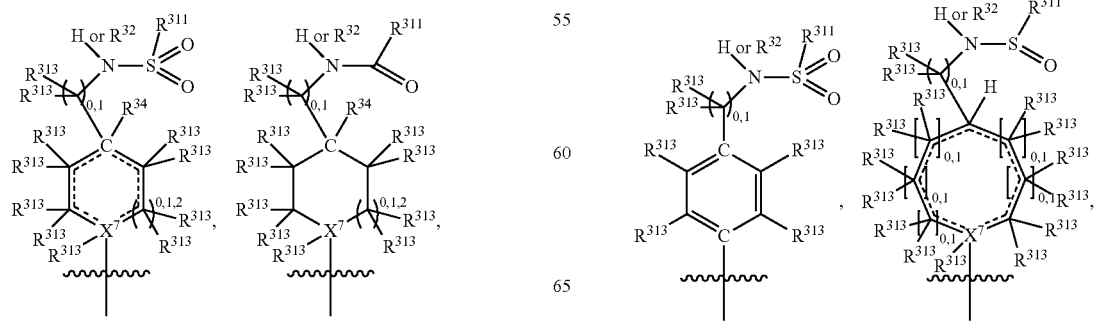

-continued

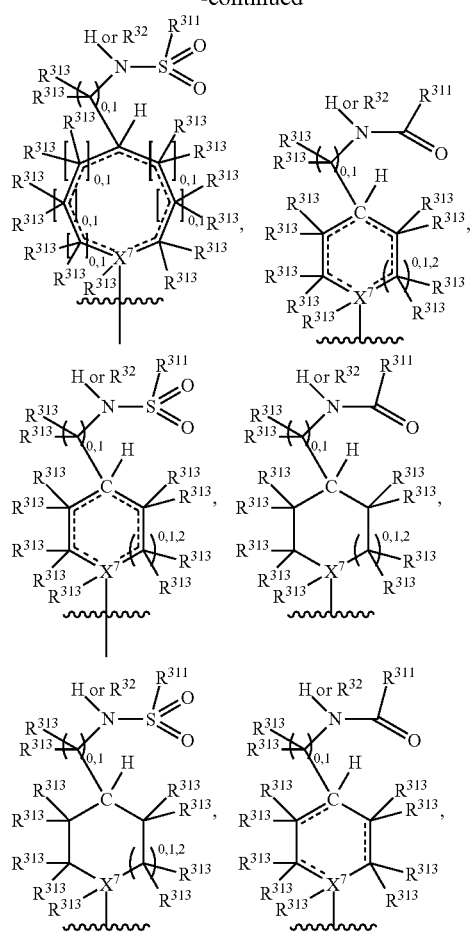

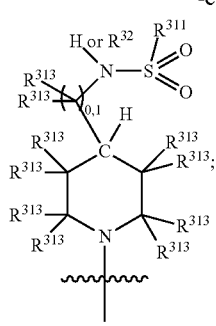

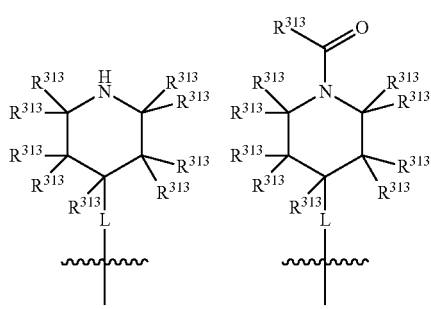

wherein $R^{32}$, $R^{34}$, $R^{311}$ and $R^{313}$ have the same meaning as anywhere above or below herein, except that in these cases $R^{32}$ is not H and $R^{34}$ is not H. In some instances the N(H or $R^{32}$) group may be absent in these compounds.

In other typical embodiments, the piperidine piperazine and cyclohexyl substituents that comprise Y may be selected from any of the following:

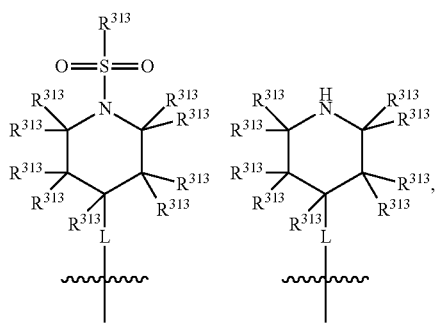

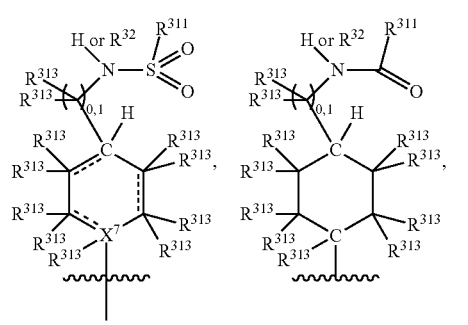

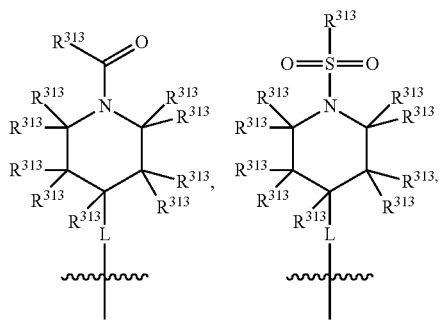

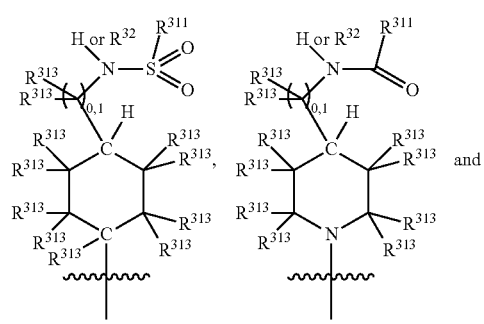

-continued
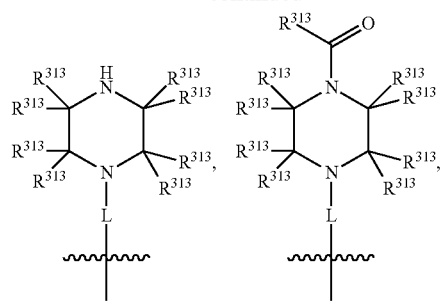
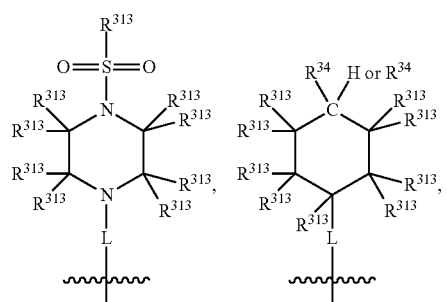
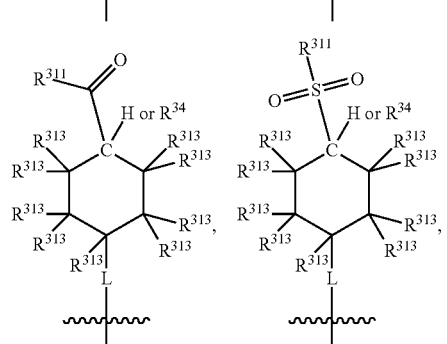
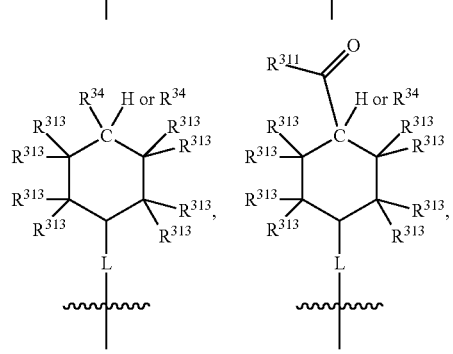
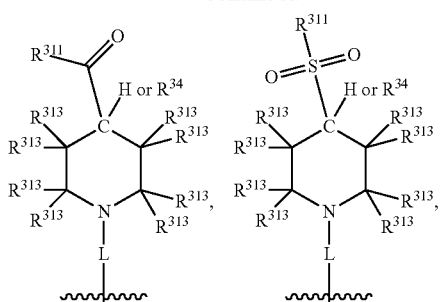
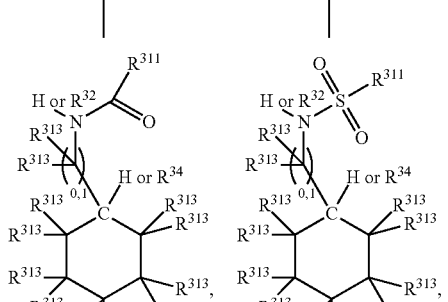
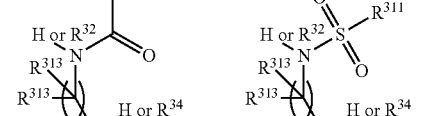
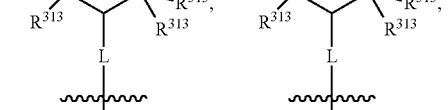
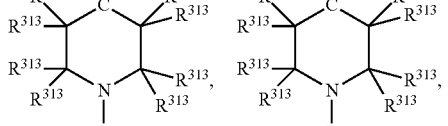

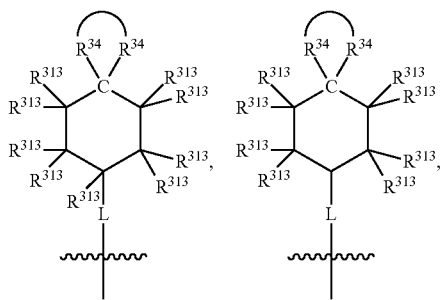
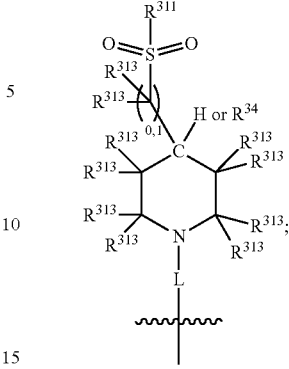
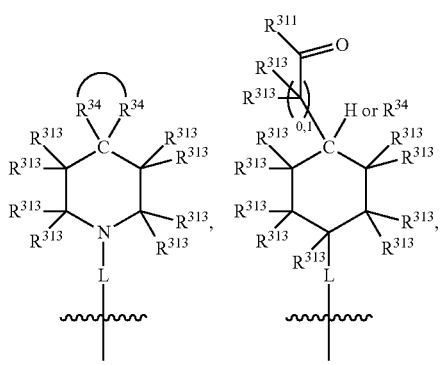
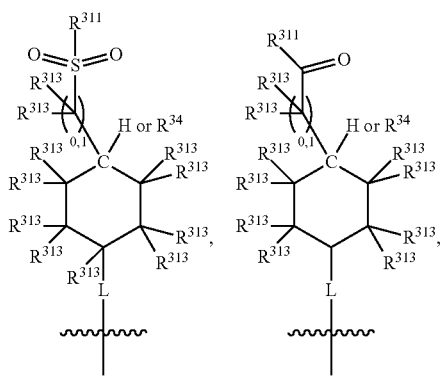
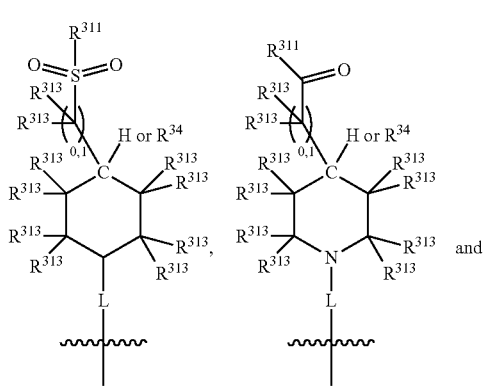

wherein in each case L may be present or absent. Typically, but not exclusively the curved line forming the ring between the $R^{34}$ groups may, together with the $R^{34}$ groups and the carbon atom to which they are bound, be a substituted or unsubstituted, saturated or unsaturated, carbocyclic group, having from 3 to 8 C ring atoms. In such cases, the curved line together with the $R^{34}$ groups may be a substituted or unsubstituted alkylene group, such as —$CH_2CH_2$—, —$CH_2CH_2CH_2$—, —$CH(CH_3)CH_2$—, —$CH_2CH_2CH_2CH_2$—, —$CH(CH_3)CH_2CH_2$—, —$CH(CH_3)CH(CH_3)$—, —$CH(CH_2CH_3)CH_2$—, —$C(CH_3)_2CH_2$—, —$CH_2CH_2CH_2CH_2CH_2$—, and —$CH_2CH_2CH_2CH_2CH_2CH_2$—. Alternatively, the curved line forming the ring between the $R^{34}$ groups may together with the $R^{34}$ groups and the carbon atom to which they are bound, form a substituted or unsubstituted, saturated or unsaturated, heterocyclic group, preferably a substituted or unsubstituted heterocyclic group with 4-8 ring atoms. Preferably the heterocyclic group comprises at least one nitrogen atom, and/or preferably comprises at least one C═O group. 5- and 6-membered substituted or unsubstituted heterocyclic groups are preferred, such as lactam groups (γ-lactams and δ-lactams), cyclic carbamates, cyclic urea compounds (such as 2-imidazolidinone, 1-methyl-2-imidazolidinone and 1,3-dimethyl-2-imidazolidinone) and hydantoins.

As has been mentioned, in some cases L may form a ring with $R^{31}$ or $R^{32}$, and/or $R^{31}$ and $R^{32}$ may form a ring with each other. The ring may be substituted or unsubstituted and may be carbocyclic or heterocyclic and may be saturated or unsaturated. In some such embodiments, the Y group may be selected from the following structures:

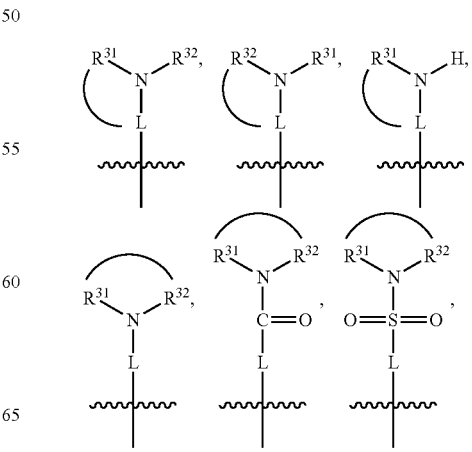

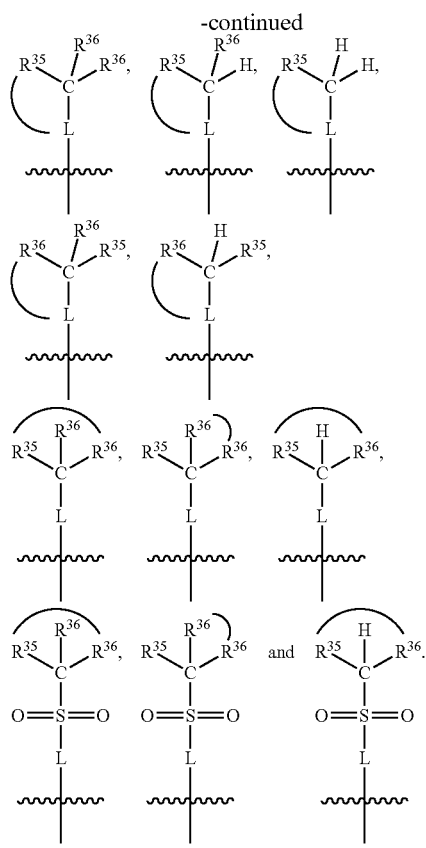

In these groups, L, $R^{31}$, $R^{32}$, $R^{35}$ and $R^{36}$ may have the meaning as defined anywhere herein. In each case L may be present or absent. The curved line represents any organic group joining $R^{31}$ and L, or $R^{31}$ and $R^{32}$, or $R^{35}$ and L, or $R^{36}$ and L, or $R^{35}$ and $R^{36}$ to form a ring. Typically, but not exclusively the curved line may be a substituted or unsubstituted alkylene group having from 1 to 6 C atoms, such as —CH$_2$—, —CH$_2$CH$_2$—, —CH$_2$CH$_2$CH$_2$—, —CH(CH$_3$)CH$_2$—, —C(CH$_3$)$_2$—, —CH$_2$CH$_2$CH$_2$CH$_2$—, —CH(CH$_3$)CH$_2$CH$_2$—, —CH(CH$_3$)CH(CH$_3$)—, —CH(CH$_2$CH$_3$)CH$_2$—, —C(CH$_3$)$_2$CH$_2$—, —CH$_2$CH$_2$CH$_2$CH$_2$CH$_2$—, and —CH$_2$CH$_2$CH$_2$CH$_2$CH$_2$CH$_2$—. In cases where the R groups form a ring with each other or with L, the R groups are typically methylene (—CH$_2$—) groups.

In typical embodiments, the atom of L which forms the ring with $R^{31}$ or $R^{32}$ or $R^{35}$ or $R^{36}$ is an atom directly bonded to the N or C of Y.

Further typically, the atom of L which forms the ring with $R^{31}$ or $R^{32}$ or $R^{35}$ or $R^{36}$ is a C atom, which may be doubly bonded to the rest of L, or singly bonded to the rest of L. Thus, in such cases, Y may be selected from the following groups:

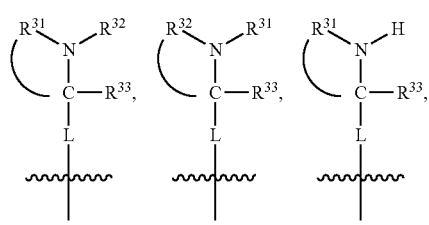

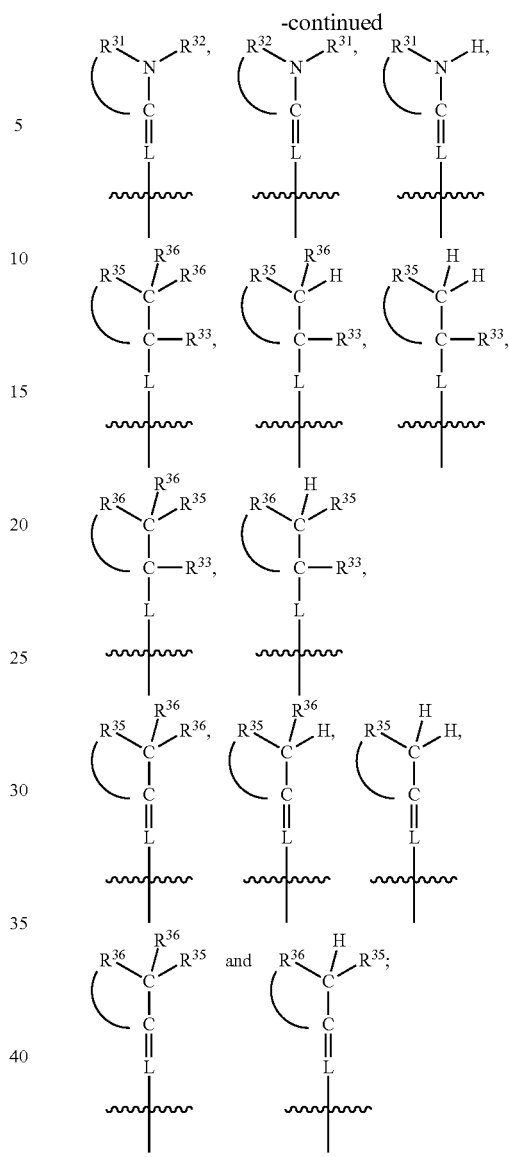

where $R^{33}$ may be selected from H and a substituted or unsubstituted organic group. In the case where L is double bonded at one end, such as to C in the above, then the valency of L is maintained. In such cases, L is trivalent rather than divalent, and may comprise a substituted or unsubstituted C$_1$-C$_6$ alkenyl group (such as =CH—, =CHCH$_2$—, =CHCH$_2$CH$_2$—, =CHCH$_2$CH$_2$CH$_2$—, =CHCH$_2$CH$_2$CH$_2$CH$_2$—, and =CHCH$_2$CH$_2$CH$_2$CH$_2$CH$_2$—).

In some cases, the rest of the linker, L, is absent (in these cases the linker comprises only the C atom which forms the ring with $R^{31}$, or comprises only —CR$^{33}$— when $R^{33}$ is present):

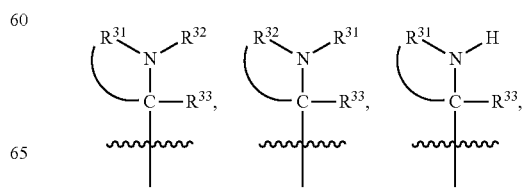

-continued

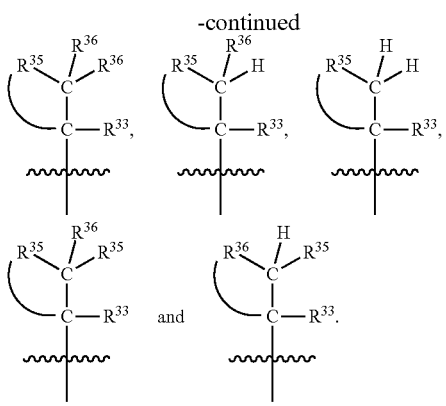

In typical embodiments of the invention, $R^{31}$ and $R^{32}$ are each independently selected from H and the following groups:
- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph);
- a substituted or unsubstituted linear or branched $C_1$-$C_6$ halogenated alkyl group (such as —$CH_2$F, —$CF_3$, and —$CH_2CF_3$);
- a substituted or unsubstituted cyclic amine or amido group (such as pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- a substituted or unsubstituted linear or branched $C_2$-$C_6$ alcohol group (such as —$CH_2CH_2$OH, —$CH_2CH_2CH_2$OH, —$CH(CH_3)CH_2$OH, —$C(CH_3)_2$OH, —$CH_2CH_2CH_2CH_2$OH, —$CH(CH_3)CH_2CH_2$OH, —$CH(CH_3)CH(CH_3)$OH, —$CH(CH_2CH_3)CH_2$OH, —$C(CH_3)_2CH_2$OH, —$CH_2CH_2CH_2CH_2CH_2$OH, and —$CH_2CH_2CH_2CH_2CH_2CH_2$OH);
- a substituted or unsubstituted linear or branched $C_2$-$C_6$ carboxylic acid group (such as —$CH_2$COOH, —$CH_2CH_2$COOH, —$CH_2CH_2CH_2$COOH, —$CH_2CH_2CH_2CH_2$COOH, and —$CH_2CH_2CH_2CH_2CH_2$COOH);
- a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)$CH_2$Ph, —(CO)$CH_2$OH, —(CO)$CH_2OCH_3$, —(CO)$CH_2NH_2$, —(CO)$CH_2$NHMe, —(CO)$CH_2NMe_2$, —(CO)-cyclopropyl, —(CO)-1,3-epoxypropan-2-yl; —(CO)$NH_2$, —(CO)NHMe, —(CO)$NMe_2$, —(CO)NHEt, —(CO)$NEt_2$, —(CO)-pyrollidine-N-yl, —(CO)-morpholine-N-yl, —(CO)-piperazine-N-yl, —(CO)—N-methyl-piperazine-N-yl, —(CO)$NHCH_2CH_2$OH, —(CO)$NHCH_2CH_2$OMe, —(CO)$NHCH_2CH_2NH_2$, —(CO)$NHCH_2CH_2$NHMe, and —(CO)$NHCH_2CH_2NMe_2$;
- a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —$CH_2$COOMe, —$CH_2CH_2$COOMe, —$CH_2CH_2CH_2$COOMe, and —$CH_2CH_2CH_2CH_2$COOMe);
- a substituted or unsubstituted linear or branched $C_1$-$C_6$ amide group (such as —CO—$NH_2$, —CO—NMeH, —CO—$NMe_2$, —CO—NEtH, —CO—NEtMe, —CO—$NEt_2$, —CO—NPrH, —CO—NPrMe, and —CO—NPrEt);
- a substituted or unsubstituted linear or branched $C_1$-$C_7$ amino carbonyl group (such as —NH—CO-Me, —NH—CO-Et, —NH—CO—Pr, —NH—CO—Bu, —NH—CO-pentyl, —NH—CO-hexyl, —NH—CO-Ph, —NMe-CO-Me, —NMe-CO-Et, —NMe-CO—Pr, —NMe-CO—Bu, —NMe-CO-pentyl, —NMe-CO-hexyl, —NMe-CO-Ph;
- a substituted or unsubstituted sulphonyl group (such as —$SO_2$Me, —$SO_2$Et, —$SO_2$Pr, —$SO_2$iPr, —$SO_2$Ph, —$SO_2$-(2,3 or 4)-F-Ph, —$SO_2$-cyclopropyl, —$SO_2CH_2CH_2OCH_3$), —$SO_2NH_2$, —$SO_2$NHMe, —$SO_2NMe_2$, —$SO_2$NHEt, —$SO_2NEt_2$, —SO2-pyrrolidine-N-yl, —$SO_2$-morpholine-N-yl, —$SO_2NHCH_2$OMe, and —$SO_2NHCH_2CH_2$OMe;
- a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-$I_2$-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)-$Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-, 4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-); and
- a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-3-yl, piperidin-4-yl, tetrahydrofuran-3-yl, tetrahydropyran-3-yl, tetrahydropyran-4-yl).

Independently, in typical embodiments of the invention, $R^{33}$ is selected from H and the following groups:
- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —$CH_2$Ph, —$CH_2$(2,3 or 4)F-Ph, —CH₂(2,3 or 4)Cl-Ph, —CH₂(2,3 or 4)Br-Ph, —CH₂(2,3 or 4)I-Ph, —CH₂CH₂Ph, —CH₂CH₂CH₂Ph, —CH₂CH₂CH₂CH₂Ph, —CH₂CH₂CH₂CH₂CH₂Ph, and —CH₂CH₂CH₂CH₂CH₂CH₂Ph);

a substituted or unsubstituted linear or branched $C_1$-$C_6$ halogenated alkyl group (such as —CH₂F, —CH₂Cl, —CF₃, —CCl₃—CBr₃, —CI₃, —CH₂CF₃, —CH₂CCl₃, —CH₂CBr₃, and —CH₂CI₃);

an —NH₂ group, or a substituted or unsubstituted linear or branched primary secondary or tertiary $C_1$-$C_6$ amine group (such as —NMeH, —NMe₂, —NEtH, —NEtMe, —NEt₂, —NPrH, —NPrMe, —NPrEt, —NPr₂, —NBuH, —NBuMe, —NBuEt, —CH₂—NH₂, —CH₂—NMeH, —CH₂—NMe₂, —CH₂—NEtH, —CH₂—NEtMe, —CH₂—NEt₂, —CH₂—NPrH, —CH₂—NPrMe, and —CH₂—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F₂-Ph, —NH-2,(3,4,5 or 6)Cl₂-Ph, —NH-2,(3,4,5 or 6)Br₂-Ph, —NH-2,(3,4,5 or 6)I₂-Ph, —NH-2,(3,4,5 or 6)Me₂-Ph, —NH-2,(3,4,5 or 6)Et₂-Ph, —NH-2,(3,4,5, or 6)Pr₂-Ph, —NH-2,(3,4,5 or 6)Bu₂-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH, or a substituted or unsubstituted linear or branched $C_1$-$C_6$ alcohol group (such as —CH₂OH, —CH₂CH₂OH, —CH₂CH₂CH₂OH, —CH(CH₃)CH₂OH, —C(CH₃)₂OH, —CH₂CH₂CH₂CH₂OH, —CH(CH₃)CH₂CH₂OH, —CH(CH₃)CH(CH₃)OH, —CH(CH₂CH₃)CH₂OH, —C(CH₃)₂CH₂OH, —CH₂CH₂CH₂CH₂CH₂OH, and —CH₂CH₂CH₂CH₂CH₂CH₂OH);

a substituted or unsubstituted linear or branched $C_1$-$C_6$ carboxylic acid group (such as —COOH, —CH₂COOH, —CH₂CH₂COOH, —CH₂CH₂CH₂COOH, —CH₂CH₂CH₂CH₂COOH, and —CH₂CH₂CH₂CH₂CH₂COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH₂Ph, —(CO)CH₂OH, —(CO)CH₂OCH₃, —(CO)CH₂NH₂, —(CO)CH₂NHMe, —(CO)CH₂NMe₂, —(CO)-cyclopropyl, —(CO)-1,3-epoxypropan-2-yl; —(CO)NH₂, —(CO)NHMe, —(CO)NMe₂, —(CO)NHEt, —(CO)NEt₂, —(CO)-pyrollidine-N-yl, —(CO)-morpholine-N-yl, —(CO)-piperazine-N-yl, —(CO)—N-methyl-piperazine-N-yl, —(CO)NHCH₂CH₂OH, —(CO)NHCH₂CH₂OMe, —(CO)NHCH₂CH₂NH₂, —(CO)NHCH₂CH₂NHMe, and —(CO)NHCH₂CH₂NMe₂;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH₂COOMe, —CH₂CH₂COOMe, —CH₂CH₂CH₂COOMe, and —CH₂CH₂CH₂CH₂COOMe);

a substituted or unsubstituted linear or branched $C_1$-$C_6$ amide group (such as —CO—NH₂, —CO—NMeH, —CO—NMe₂, —CO—NEtH, —CO—NEtMe, —CO—NEt₂, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO—Pr, —NH—CO—Bu, —NH—CO-pentyl, —NH—CO-hexyl, —NH—CO-Ph, —NMe-CO-Me, —NMe-CO-Et, —NMe-CO—Pr, —NMe-CO—Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH₂F, —OCHF₂, —OCF₃, —O-Ph, —O—CH₂-Ph, —O—CH₂-(2,3 or 4)-F-Ph, —O—CH₂-(2,3 or 4)-Cl-Ph, —CH₂OMe, —CH₂OEt, —CH₂OPr, —CH₂OBu, —CH₂CH₂OMe, —CH₂CH₂CH₂OMe, —CH₂CH₂CH₂CH₂OMe, and —CH₂CH₂CH₂CH₂CH₂OMe);

a substituted or unsubstituted linear or branched amino-alkoxy group (such as, —OCH₂CH₂NH₂, —OCH₂CH₂NHMe, —OCH₂CH₂NMe₂, —OCH₂CH₂NHEt, and —OCH₂CH₂NEt₂;

a substituted or unsubstituted sulphonyl group (such as —SO₂Me, —SO₂Et, —SO₂Pr, —SO₂iPr, —SO₂Ph, —SO₂-(2,3 or 4)-F-Ph, —SO₂-cyclopropyl, —SO₂CH₂CH₂OCH₃), —SO₂NH₂, —SO₂NHMe, —SO₂NMe₂, —SO₂NHEt, —SO₂NEt₂, —SO2-pyrrolidine-N-yl, —SO₂-morpholine-N-yl, —SO₂NHCH₂OMe, and —SO₂NHCH₂CH₂OMe;

a substituted or unsubstituted aminosulphonyl group (such as —NHSO₂Me, —NHSO₂Et, —NHSO₂Pr, —NHSO₂iPr, —NHSO₂Ph, —NHSO₂-(2,3 or 4)-F-Ph, —NHSO₂-cyclopropyl, —NHSO₂CH₂CH₂OCH₃);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F₂-Ph-, 2,(3,4,5 or 6)-Cl₂-Ph-, 2,(3,4,5 or 6)-Br₂-Ph-, 2,(3,4,5 or 6)-I₂-Ph-, 2,(3, 4,5 or 6)-Me₂-Ph-, 2,(3,4,5 or 6)-Et₂-Ph-, 2,(3,4,5 or 6)-Pr₂-Ph-, 2,(3,4,5 or 6)-Bu₂-Ph-, 2,(3,4,5 or 6)-(CN)₂-Ph-, 2,(3,4,5 or 6)-(NO₂)₂-Ph-, 2,(3,4,5 or 6)-(NH₂)₂-Ph-, 2,(3,4,5 or 6)-(MeO)₂-Ph-, 2,(3,4,5 or 6)-(CF₃)₂-Ph-, 3,(4 or 5)-F₂-Ph-, 3,(4 or 5)-Cl₂-Ph-, 3,(4 or 5)-Br₂-Ph-, 3,(4 or 5)-I₂-Ph-, 3,(4 or 5)- Me₂-Ph-, 3,(4 or 5)-Et₂-Ph-, 3,(4 or 5)-Pr₂-Ph-, 3,(4 or 5)-Bu₂-Ph-, 3,(4 or 5)-(CN)₂-Ph-, 3,(4 or 5)-(NO₂)₂-Ph-, 3,(4 or 5)-(NH₂)₂-Ph-, 3,(4 or 5)-(MeO)₂-Ph-, 3,(4 or 5)-(CF₃)₂-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO₂)-Ph-, 3-(NO₂)-Ph-, 4-(NO₂)-Ph-, 2-(NH₂)-Ph-, 3-(NH₂)-Ph-, 4-(NH₂)-Ph-, 2-MeO-Ph-, 3-MeO-Ph-, 4-MeO-Ph-, 2-(NH₂—CO)-Ph-, 3-(NH₂—CO)-Ph-, 4-(NH₂—CO)-Ph-, 2-CF₃-Ph-, 3-CF₃-Ph-, 4-CF₃-Ph-, 2-CF₃O-Ph-, 3-CF₃O-Ph-, and 4-CF₃O-Ph-); and a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

In more typical embodiments, $R^{3'}$ is selected from a carbocyclic or heterocyclic group, which may be saturated or unsaturated, or aromatic or aliphatic, such as a substituted or unsubstituted phenyl group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph-, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-).

In more typical embodiments, $R^{32}$ is selected from H or a $C_1$-$C_6$ alkyl group (such as Me, Et, Pr, i-Pr, n-Bu, i-Bu, t-Bu, pentyl and hexyl).

In more typical embodiments, $R^{33}$ is selected from H, a substituted or unsubstituted $C_1$-$C_6$ alkyl group, an NH$_2$ group or a substituted or unsubstituted $C_1$-$C_6$ amino group, a substituted or unsubstituted $C_1$-$C_6$ alkoxy group, and a nitrile group.

Each $R^{34}$ is typically independently selected from H and a group selected from the following groups:

a halogen (such as —F, —Cl, —Br and —I);
a nitrile group;
a substituted or unsubstituted linear or branched $C_1$-$C_6$ alkyl group (such as Me, Et, Pr, i-Pr, n-Bu, i-Bu, t-Bu, pentyl and hexyl);
a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
a substituted or unsubstituted linear or branched $C_1$-$C_6$ halogenated alkyl group (such as —CH$_2$F, —CH$_2$Cl, —CF$_3$, —CCl$_3$—CBr$_3$, —CI$_3$, —CH$_2$CF$_3$, —CH$_2$CCl$_3$, —CH$_2$CBr$_3$, and —CH$_2$CI$_3$);
an —NH$_2$ group, or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph,
a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);
a substituted or unsubstituted cyclic $C_3$-$C_8$ alkyl group (such as cyclopropyl, cyclobutyl, cyclopentyl, cyclohexyl, cycloheptyl and cyclooctyl);
an —OH or a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$OH, and —CH$_2$CH$_2$CH$_2$CH$_2$CH$_2$OH);
a substituted or unsubstituted linear or branched $C_1$-$C_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);
a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);
a substituted or unsubstituted linear or branched $C_1$-$C_7$ amino carbonyl group (such as —NH—CO-Me, —NH—CO-Et, —NH—CO—Pr, —NH—CO—Bu, —NH—CO-pentyl, —NH—CO-hexyl, —NH—CO-Ph, —NMe-CO-Me, —NMe-CO-Et, —NMe-CO—Pr, —NMe-CO—Bu, —NMe-CO-pentyl, —NMe-CO-hexyl, —NMe-CO-Ph;
a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, SO$_2$-morpholine-N-yl, —SO$_2$NHCH$_2$OMe, and —SO$_2$NHCH$_2$CH$_2$OMe;

an substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)- Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

In some embodiments the $R^{34}$ groups form a ring with each other. In such cases the ring is typically a 3, 4, 5, 6 or 7 membered substituted or unsubstituted carbocyclic ring or heterocyclic ring, which may be saturated or unsaturated.

In some embodiments, one $R^{34}$ group is —H and one is not —H. In other embodiments, both $R^{34}$ groups are —H. In yet further embodiments neither $R^{34}$ group is —H.

As has been mentioned, $R^{35}$ is selected from an alcohol group or an ether group. Typically $R^{35}$ is selected from a group of formula —(C$_0$-C$_7$)—O—(C$_0$-C$_7$) where the C$_0$-C$_7$ groups may be linear or branched alkyl groups, or may be phenyl groups, or may be absent (C$_0$). More typically, $R^{35}$ may be a —(C$_1$-C$_7$)—OH alcohol group, a —O—(C$_1$-C$_7$) ether group, or a —(C$_1$-C$_4$)—O—(C$_1$-C$_4$) ether group, or a —(C$_1$-C$_3$)—O—(C$_1$-C$_3$) ether group.

$R^{35}$ is typically selected from the following oxygen-containing groups:

an —OH or a substituted or unsubstituted linear or branched C$_1$-C$_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, —CH$_2$CH$_2$CH$_2$CH$_2$CH$_2$OMe, —CH$_2$CH$_2$OEt, —CH$_2$CH$_2$OPr, —CH$_2$CH$_2$OBu, —CH$_2$CH$_2$Opentyl, —CH$_2$CH$_2$CH$_2$OEt, —CH$_2$CH$_2$CH$_2$OPr, and —CH$_2$CH$_2$CH$_2$OBu).

In preferred embodiments $R^{35}$ is selected from an —OH group and an —OR" group where R" is a C$_1$-C$_6$ alkyl group (such as Me, Et, Pr, i-Pr, n-Bu, i-Bu, t-Bu, pentyl and hexyl).

Each $R^{36}$ is typically each independently selected from H and a group selected from the following groups:

a halogen (such as —F, —Cl, —Br and —I, preferably —F);

a substituted or unsubstituted linear or branched C$_1$-C$_6$ alkyl group (such as Me, Et, Pr, i-Pr, n-Bu, i-Bu, t-Bu, pentyl and hexyl);

a substituted or unsubstituted linear or branched C$_1$-C$_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched C$_1$-C$_6$ halogenated alkyl group (such as —CH$_2$F, —CH$_2$Cl, —CF$_3$, —CCl$_3$—CBr$_3$, —CI$_3$, —CH$_2$CF$_3$, —CH$_2$CCl$_3$, —CH$_2$CBr$_3$, and —CH$_2$CI$_3$);

an —NH$_2$ group, or a substituted or unsubstituted linear or branched primary secondary or tertiary C$_1$-C$_6$ amine group (such as —NMeH, —NMe$_2$, —NEtH, —NEtMe, —NEt$_2$, —NPrH, —NPrMe, —NPrEt, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph,
a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);
a substituted or unsubstituted cyclic C$_3$-C$_8$ alkyl group (such as cyclopropyl, cyclobutyl, cyclopentyl, cyclohexyl, cycloheptyl and cyclooctyl);
an —OH or a substituted or unsubstituted linear or branched C$_1$-C$_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);
a substituted or unsubstituted linear or branched C$_1$-C$_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
a substituted or unsubstituted linear or branched C$_1$-C$_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);
a substituted or unsubstituted linear or branched C$_1$-C$_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);
a substituted or unsubstituted linear or branched C$_1$-C$_7$ amino carbonyl group (such as —NH—CO-Me, —NH—CO-Et, —NH—CO—Pr, —NH—CO—Bu, —NH—CO-pentyl, —NH—CO-hexyl, —NH—CO—Ph, —NMe-CO-Me, —NMe-CO-Et, —NMe-CO—Pr, —NMe-CO—Bu, —NMe-CO-pentyl, —NMe-CO-hexyl, —NMe-CO-Ph;
a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$OMe);
a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;
a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO2-pyrolidine-N-yl, SO$_2$-morpholine-N-yl, —SO$_2$NHCH$_2$OMe, and —SO$_2$NHCH$_2$CH$_2$OMe;
an substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);
a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3, 4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)- Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and
a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

In some embodiments the R$^{36}$ groups form a ring with each other. In such cases the ring is typically a 3, 4, 5, 6 or 7 membered substituted or unsubstituted carbocyclic ring or heterocyclic ring, which may be saturated or unsaturated.

In some embodiments, one R$^{36}$ group is —H and one is not —H. In other embodiments, both R$^{36}$ groups are —H. In yet further embodiments neither R$^{36}$ group is —H.

In preferred embodiments, at least one R$^{36}$ group comprises an alkyl group (such as a lower alkyl group or a C$_1$-C$_6$ alkyl group such as Me, Et, Pr, i-Pr, n-Bu, i-Bu, t-Bu, pentyl and hexyl) or at least one R$^{36}$ group comprises a cycloalkyl group (such as a 3, 4, 5, 6 or 7 membered carbocyclic ring), which alkyl group cycloalkyl group or may be saturated or unsaturated, or at least one R$^{36}$ group is a halogen (preferably —F).

In some further typical embodiments, the invention therefore provides a tryptophan-2,3-dioxygenase (TDO) and/or indoleamine-2,3-dioxygenase (IDO) inhibitor compound for use in medicine, which compound comprises the following formula:

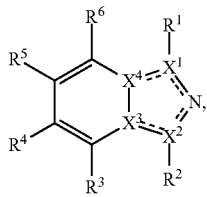

wherein $X^1$, and $X^2$ may be the same or different and each is independently selected from C, and N; $X^3$ and $X^4$ are each independently selected from C and N, wherein one of $X^3$ and $X^4$ is C and one of $X^3$ and $X^4$ is N; each bond represented by a dotted line may be present or absent, provided that one of $X^3$ and $X^4$ has a double bond and the N between $X^1$ and $X^2$ has a double bond and the valencies of $X^1$, $X^2$, $X^3$, $X^4$ and N are maintained; $R^1$ and $R^2$ may be present or absent and may be the same or different and each is independently selected from H and a substituted or unsubstituted organic group, provided that the number of $R^1$ and $R^2$ groups present is such that the respective valencies of $X^1$ and $X^2$ are maintained; $R^3$, $R^4$, $R^5$ and $R^6$ may be the same or different and each is independently selected from H and a substituted or unsubstituted organic group; and wherein at least one of $R^5$ and $R^6$ comprises a group Y, wherein Y is a group having a formula selected from the following:

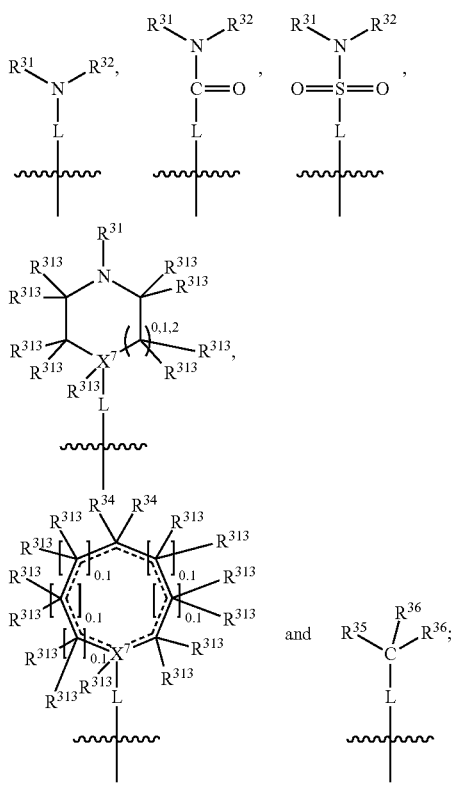

wherein L may be present or absent, and is a substituted or unsubstituted organic linking group selected from a substituted or unsubstituted $C_1$-$C_7$ alkylene group (such as —$CH_2$—, —$CH_2CH_2$—, —$CH_2CH_2CH_2$—, —$CH(CH_3)CH_2$—, —$C(CH_3)_2$—, —$CH_2CH_2CH_2CH_2$—, —$CH(CH_3)CH_2CH_2$—, —$CH(CH_3)CH(CH_3)$—, —$CH(CH_2CH_3)CH_2$—, —$C(CH_3)_2CH_2$—, —$CH_2CH_2CH_2CH_2CH_2$—, and —$CH_2CH_2CH_2CH_2CH_2CH_2$—), a $C_1$-$C_7$ divalent alkoxy group (such as —$OCH_2$—, —$OCH_2CH_2$—, —$OCH_2CH_2CH_2$—, —O—$CH(CH_3)CH_2$—, —OC$(CH_3)_2$—, —$OCH_2CH_2CH_2CH_2$—, —$OCH(CH_3)CH_2CH_2$—, —$OCH(CH_3)CH(CH_3)$—, —$OCH(CH_2CH_3)CH_2$—, —$OC(CH_3)_2CH_2$—, —$OCH_2CH_2CH_2CH_2CH_2$—, —$OCH_2CH_2CH_2CH_2CH_2CH_2$—, —OCHF—, —$OCF_2$—, —O-phenylene-, —O—$CH_2$-phenylene-, —O—$CH_2$-(2,3 or 4)-F-phenylene-, —O—$CH_2$-(2,3 or 4)-Cl-phenylene-, —$CH_2OCH_2$—, —$CH_2OCH_2CH_2$—, —$CH_2OCH_2CH_2CH_2$—, —$CH_2OCH_2CH_2CH_2$—, —$CH_2CH_2OCH_2$—, —$CH_2CH_2CH_2OCH_2$—, —$CH_2CH_2CH_2CH_2OCH_2$—, —$CH_2CH_2CH_2CH_2CH_2OCH_2$—, —$CH_2CH_2CH_2CH_2CH_2CH_2OCH_2$—, —$CH_2CH_2OCH_2CH_2$—, —$CH_2CH_2OCH_2CH_2CH_2$—, —$CH_2CH_2OCH_2CH_2CH_2$—, —$CH_2CH_2OCH_2CH_2CH_2CH_2$—, —$CH_2CH_2CH_2OCH_2CH_2$—, —$CH_2CH_2CH_2OCH_2CH_2CH_2$—, and —$CH_2CH_2CH_2OCH_2CH_2CH_2CH_2$—, an —O— atom, and a —$N(R^{32})$— group (such as a —NH— group); $R^{31}$ and $R^{32}$ may be the same or different; each $R^{34}$ may be the same or different; $R^{35}$ is selected from a substituted or unsubstituted alcohol group or ether group; each $R^{36}$ may be the same or different; $X^7$ is selected from C and N; each bond represented by a dotted line may be present or absent; and each $R^{313}$ may be the same or different;

and wherein $R^1$, $R^2$, $R^3$ and $R^4$ do not comprise a group having a cyclic group, and if one of $R^5$ and $R^6$ is not Y it also does not comprise a group having a cyclic group;

and wherein $R^1$, $R^2$, $R^3$, $R^4$, $R^5$ and $R^6$ do not form rings with each other;

and wherein, where present, $R^1$ and $R^2$ are each independently selected from H and a group selected from the following groups:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2$Ph, —$CH_2CH_2CH_2CH_2$Ph, and —$CH_2CH_2CH_2CH_2CH_2CH_2$Ph);

a substituted or unsubstituted linear or branched $C_1$-$C_6$ halogenated alkyl group (such as —$CH_2$F, —$CF_3$, and —$CH_2CF_3$);

an —$NH_2$ group, or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph, a substituted or unsubstituted cyclic C$_3$-C$_5$ alkyl group (such as cyclopropyl, cyclobutyl, cyclopentyl, cyclohexyl, cycloheptyl and cyclooctyl);

an —OH, or a substituted or unsubstituted linear or branched C$_1$-C$_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_1$-C$_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched C$_1$-C$_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched C$_1$-C$_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted linear or branched C$_1$-C$_7$ amino carbonyl group (such as —NH—CO-Me, —NH—CO-Et, —NH—CO—Pr, —NH—CO—Bu, —NH—CO-pentyl, —NH—CO-hexyl, —NH—CO-Ph, —NMe-CO-Me, —NMe-CO-Et, —NMe-CO—Pr, —NMe-CO—Bu, —NMe-CO-pentyl, —NMe-CO-hexyl, —NMe-CO-Ph;

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$OMe, —CH$_2$CH$_2$CH$_2$OMe, —CH$_2$CH$_2$CH$_2$OMe, and —CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), SO$_2$NH$_2$, —SO$_2$NHMe, —SO$_2$NMe$_2$, —SO$_2$NHEt, —SO$_2$NEt$_2$, —SO2-pyrolidine-N-yl, —SO$_2$-morpholine-N-yl, —SO$_2$NHCH$_2$OMe, and —SO$_2$NHCH$_2$CH$_2$OMe;

a substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)- Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

and wherein, where present, R$^3$, R$^4$, R$^5$, R$^6$ and R$^{313}$ are each independently selected from H and a group selected from the following groups:

a halogen (such as —F, —Cl, —Br and —I);

a nitrile group;

a substituted or unsubstituted linear or branched C$_1$-C$_6$ alkyl group (such as Me, Et, Pr, i-Pr, n-Bu, i-Bu, t-Bu, pentyl and hexyl);

a substituted or unsubstituted linear or branched C$_1$-C$_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched C$_1$-C$_6$ halogenated alkyl group (such as —CH$_2$F, —CH$_2$Cl, —CF$_3$, —CCl$_3$—CBr$_3$, —CI$_3$, —CH$_2$CF$_3$, —CH$_2$CCl$_3$, —CH$_2$CBr$_3$, and —CH$_2$CI$_3$);

an —NH$_2$ group, or a substituted or unsubstituted linear or branched primary secondary or tertiary C$_1$-C$_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic C$_3$-C$_8$ alkyl group (such as cyclopropyl, cyclobutyl, cyclopentyl, cyclohexyl, cycloheptyl and cyclooctyl);

an —OH, or a substituted or unsubstituted linear or branched C$_1$-C$_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_1$-C$_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched C$_1$-C$_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched C$_1$-C$_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted linear or branched C$_1$-C$_7$ amino carbonyl group (such as —NH—CO-Me, —NH—CO-Et, —NH—CO—Pr, —NH—CO—Bu, —NH—CO-pentyl, —NH—CO-hexyl, —NH—CO-Ph, —NMe-CO-Me, —NMe-CO-Et, —NMe-CO—Pr, —NMe-CO—Bu, —NMe-CO-pentyl, —NMe-CO-hexyl, —NMe-CO-Ph;

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO2-pyrolidine-N-yl, —SO$_2$-morpholine-N-yl, —SO$_2$NHCH$_2$OMe, and —SO$_2$NHCH$_2$CH$_2$OMe;

a substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)- Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);

a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl); and where there are two R$^{313}$ groups attached to the same atom, they may together form a group which is double bonded to that atom, (such as a carbonyl group (═O)

or an alkene group (=C(R')$_2$) wherein each R' group is the same or different and is H or an organic group, preferably H or a straight or branched C$_1$-C$_6$ alkyl group), or the two R$^{313}$ groups on the same atom may form a ring, preferably a substituted or unsubstituted C$_3$-C$_6$ saturated carbocyclic ring together with the atom to which they are attached (such as a substituted or unsubstituted cyclopropyl ring or a substituted or unsubstituted cyclobutyl ring), this being more preferable when the two R$^{313}$ groups are on an atom adjacent to the N—R$^{31}$, (or adjacent to the (C—R$^{34}$) and/or adjacent to the X$^7$;

and wherein where present R$^{31}$ and R$^{32}$ are each independently selected from H and the following groups:

a substituted or unsubstituted linear or branched C$_1$-C$_6$ alkyl group (such as Me, Et, Pr, i-Pr, n-Bu, i-Bu, t-Bu, pentyl and hexyl);

a substituted or unsubstituted linear or branched C$_1$-C$_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched C$_1$-C$_6$ halogenated alkyl group (such as —CH$_2$F, —CF$_3$, and —CH$_2$CF$_3$);

a substituted or unsubstituted monocyclic amine or amido group (such as pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted monocyclic C$_3$-C$_8$ alkyl group (such as cyclopropyl, cyclobutyl, cyclopentyl, cyclohexyl, cycloheptyl and cyclooctyl);

a substituted or unsubstituted linear or branched C$_2$-C$_6$ alcohol group (such as —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_2$-C$_6$ carboxylic acid group (such as —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched C$_1$-C$_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched C$_1$-C$_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe$_2$, —SO$_2$NMe$_2$, —SO$_2$NHEt, —SO$_2$NEt$_2$, —SO$_2$-morpholine-N-yl, —SO$_2$NHCH$_2$OMe, and —SO$_2$NHCH$_2$CH$_2$OMe;

a substituted or unsubstituted monocyclic aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a substituted or unsubstituted saturated or unsaturated monocyclic heterocyclic group such as a monocyclic aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated monocyclic heterocyclic group (such as piperidin-3-yl, piperidin-4-yl, tetrahydrofuran-3-yl, tetrahydropyran-3-yl, tetrahydropyran-4-yl);

and wherein where present each R$^{34}$ is independently selected from H and a group selected from the following groups:

a halogen (such as —F, —Cl, —Br and —I);

a nitrile group;

a substituted or unsubstituted linear or branched C$_1$-C$_6$ alkyl group (such as Me, Et, Pr, i-Pr, n-Bu, i-Bu, t-Bu, pentyl and hexyl);

a substituted or unsubstituted linear or branched C$_1$-C$_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched C$_1$-C$_6$ halogenated alkyl group (such as —CH$_2$F, —CH$_2$Cl, —CF$_3$, —CCl$_3$—CBr$_3$, —CI$_3$, —CH$_2$CF$_3$, —CH$_2$CCl$_3$, —CH$_2$CBr$_3$, and —CH$_2$CI$_3$);

an —NH$_2$ group, or a substituted or unsubstituted linear or branched primary secondary or tertiary C$_1$-C$_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic C$_3$-C$_8$ alkyl group (such as cyclopropyl, cyclobutyl, cyclopentyl, cyclohexyl, cycloheptyl and cyclooctyl);

an —OH or a substituted or unsubstituted linear or branched C$_1$-C$_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_1$-C$_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched C$_1$-C$_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched C$_1$-C$_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted linear or branched C$_1$-C$_7$ amino carbonyl group (such as —NH—CO-Me, —NH—CO-Et, —NH—CO—Pr, —NH—CO—Bu, —NH—CO-pentyl, —NH—CO-hexyl, —NH—CO-Ph, —NMe-CO-Me, —NMe-CO-Et, —NMe-CO—Pr, —NMe-CO—Bu, —NMe-CO-pentyl, —NMe-CO-hexyl, —NMe-CO-Ph;

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO2-pyrolidine-N-yl, —SO$_2$-morpholine-N-yl, —SO$_2$NHCH$_2$OMe, and —SO$_2$NHCH$_2$CH$_2$OMe;

an substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)- Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, tetrahydrofuran-3-yl, tetrahydropyran-2-yl, tetrahydropyran-3-yl, tetrahydropyran-4-yl);

and wherein, where present, R$^{35}$ is selected from alcohol and ether groups of formula —(C$_0$-C$_7$)—O—(C$_0$-C$_7$) where the $C_0$-$C_7$ groups may be linear or branched alkyl groups, or may be phenyl groups, or may be absent ($C_0$);

more preferably wherein $R^{35}$ is selected from a —($C_1$-$C_7$)—OH alcohol group, a —O—($C_1$-$C_7$) ether group, and a —($C_1$-$C_4$)—O—($C_1$-$C_4$) ether group;

or more preferably still $R^{35}$ is selected from:

- an —OH or a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH); or
- a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, —CH$_2$CH$_2$CH$_2$CH$_2$CH$_2$OMe, —CH$_2$CH$_2$CH$_2$CH$_2$CH$_2$CH$_2$OMe, —CH$_2$CH$_2$OEt, —CH$_2$CH$_2$OPr, —CH$_2$CH$_2$OBu, —CH$_2$CH$_2$Opentyl, —CH$_2$CH$_2$CH$_2$OEt, —CH$_2$CH$_2$CH$_2$OPr, and —CH$_2$CH$_2$CH$_2$OBu);

and wherein, where present, each $R^{36}$ is typically each independently selected from H and a group selected from the following groups:

- a halogen (such as —F, —Cl, —Br and —I, preferably —F);
- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
- a substituted or unsubstituted linear or branched $C_1$-$C_6$ halogenated alkyl group (such as —CH$_2$F, —CH$_2$Cl, —CF$_3$, —CCl$_3$, —CBr$_3$, —CI$_3$, —CH$_2$CF$_3$, —CH$_2$CCl$_3$, —CH$_2$CBr$_3$, and —CH$_2$CI$_3$);
- an —NH$_2$ group, or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);
- a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5 or 6)Pr$_2$-Ph, —NH-2,(3,4,5 or 6)Bu$_2$-Ph,
- a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- an —OH or a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);
- a substituted or unsubstituted linear or branched $C_1$-$C_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
- a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
- a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);
- a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);
- a substituted or unsubstituted linear or branched $C_1$-$C_7$ amino carbonyl group (such as —NH—CO-Me, —NH—CO-Et, —NH—CO—Pr, —NH—CO—Bu, —NH—CO-pentyl, —NH—CO-hexyl, —NH—CO-Ph, —NMe-CO-Me, —NMe-CO-Et, —NMe-CO—Pr, —NMe-CO—Bu, —NMe-CO-pentyl, —NMe-CO-hexyl, —NMe-CO-Ph;
- a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);
- a substituted or unsubstituted linear or branched amino-alkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;
- a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO2-pyrrolidine-N-yl, —SO$_2$-morpholine-N-yl, —SO$_2$NHCH$_2$OMe, and —SO$_2$NHCH$_2$CH$_2$OMe;

an substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)- Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

preferably wherein R$^{35}$ is selected from an —OH group and an —OR″ group where R″ is a C$_1$-C$_6$ alkyl group (such as Me, Et, Pr, i-Pr, n-Bu, i-Bu, t-Bu, pentyl and hexyl);

and/or preferably wherein at least one R$^{36}$ group comprises an alkyl group (such as a lower alkyl group or a C$_1$-C$_6$ alkyl group such as Me, Et, Pr, i-Pr, n-Bu, i-Bu, t-Bu, pentyl and hexyl) or at least one R$^{36}$ group comprises a cycloalkyl group (such as a 3, 4, 5, 6 or 7 membered carbocyclic ring), which alkyl group cycloalkyl group or may be saturated or unsaturated, or at least one R$^{36}$ group is a halogen (preferably —F).

In one embodiment, a compound disclosed herein is of formula Ia or Ib, or a pharmaceutically acceptable salt thereof:

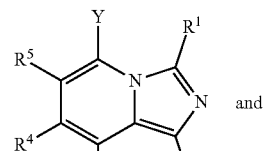
(Ia)

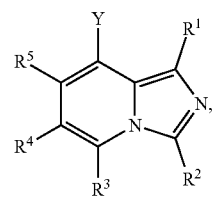
(Ib)

wherein:
each of R$^1$, R$^2$, R$^3$ and R$^5$ is independently selected from the group consisting of (1) H, (2) halogen, and (3) C$_{1-6}$ alkyl;
R$^4$ is selected from the group consisting of (1) H, (2) halogen, (3) C$_1$-C$_6$alkyl, optionally substituted with 1-3 groups independently selected from halogen and —OH, (4) C$_3$-C$_6$ cycloalkyl, optionally substituted with 1-3 groups independently selected from halogen and C$_1$-C$_6$alkyl, and (5) nitrile; and
Y is selected from the group consisting of:

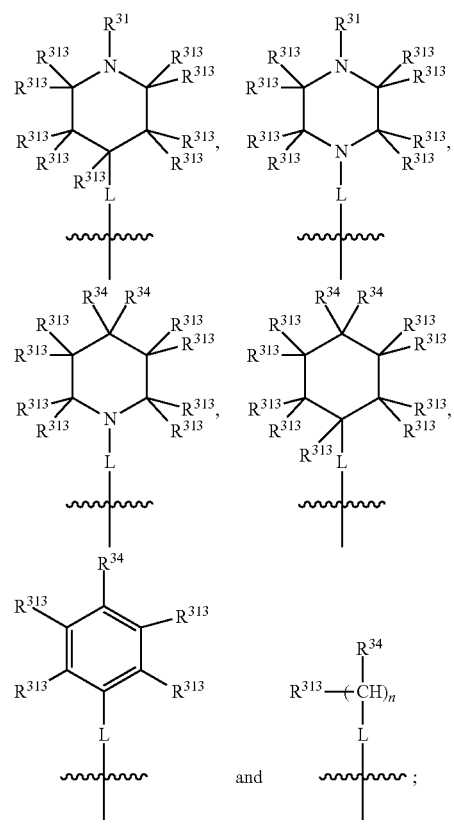

wherein
n is 1, 2, 3 or 4;
L is selected from the group consisting of (1) a bond, (2) C$_{1-6}$alkylene, (3) —NH—, and (4) —NH—C(O)—;

$R^{31}$ is selected from the group consisting of (1) H, (2) —OH, (3) halogen, (4) —C(O)—$C_{1-6}$ alkyl, (5) —S(O)$_2$—$C_{1-6}$alkyl, (6) —NH—C(O)—$C_{1-6}$ alkyl, and (7) 5- or 6-membered heterocyclyl, optionally substituted with 1-5 groups independently selected from $C_{1-6}$alkyl, oxo, —C(O)—H, —C(O)—NH$_2$, C(O)—NH—$C_{1-6}$ alkyl, —NH$_2$, and —NH—$C_{1-6}$alkyl;

$R^{34}$ is selected from the group consisting of (1) H, (2) —OH, (3) halogen, (4) —NH$_2$, (5) —C(O)—$C_{1-6}$alkyl, (6) —S(O)$_2$—$C_{1-6}$alkyl, (7) —NH—C(O)—$C_{1-6}$alkyl, and (8) 5- or 6-membered heterocyclyl, optionally substituted with 1-5 groups independently selected from $C_{1-6}$alkyl, oxo, —C(O)—H, —C(O)—NH$_2$, C(O)—NH—$C_{1-6}$ alkyl, —NH$_2$, and —NH—$C_{1-6}$alkyl;

each occurrence of $R^{313}$ is independently selected from the group consisting of (1) H, (2) —OH, (3) halogen, and (4) $C_{1-6}$ alkyl.

In one embodiment, the compound described above is of formula Ic or Id, or a pharmaceutically acceptable salt thereof:

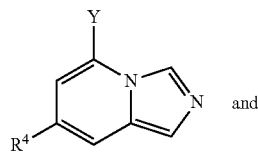
(Ic)

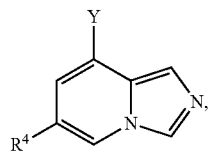
(Id)

wherein:
$R^4$ is selected from the group consisting of (1) H, (2) halogen, (3) $C_1$-$C_4$alkyl, optionally substituted with 1-3 halogens, and (4) $C_3$-$C_6$ cycloalkyl, optionally substituted with 1-3 groups independently selected from halogen and $C_1$-$C_6$alkyl; and Y is selected from the group consisting of:

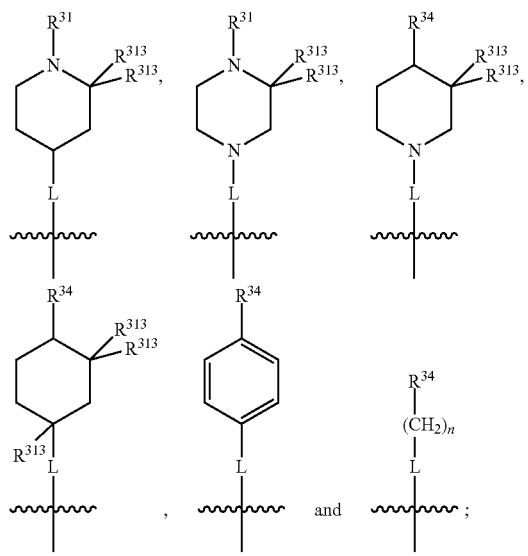

wherein
n is 1, 2 or 3;
L is selected from the group consisting of (1) a bond, (2) —NH—, and (3) —NH—C(O)—;

$R^{31}$ is selected from the group consisting of (1) H, (2) halogen, (3) —C(O)—$C_{1-4}$alkyl, (5) —S(O)$_2$—$C_{1-4}$alkyl, (6) —NH—C(O)—$C_{1-4}$alkyl, and (7) heterocyclyl, optionally substituted with 1-5 groups independently selected from $C_{1-6}$alkyl, oxo, —C(O)—H, —C(O)—NH$_2$, C(O)—NH—$C_{1-6}$ alkyl, —NH$_2$, and —NH—$C_{1-6}$alkyl;

$R^{34}$ is selected from the group consisting of (1) H, (2) halogen, (3) —C(O)—$C_{1-6}$alkyl, (4) —S(O)$_2$—$C_{1-4}$alkyl, (5) —NH—C(O)—$C_{1-4}$alkyl, and (6) heterocyclyl, optionally substituted with 1-5 groups independently selected from $C_{1-6}$alkyl, oxo, —C(O)—H, —C(O)—NH$_2$, C(O)—NH—$C_{1-6}$ alkyl, —NH$_2$, and —NH—$C_{1-6}$alkyl;

each occurrence of $R^{313}$ is independently selected from the group consisting of (1) H and (2) $C_{1-6}$ alkyl.

In one embodiment, each heterocyclyl of $R^{31}$ and $R^{34}$ of the compound disclosed above, or a pharmaceutically acceptable salt thereof, is independently selected from the group consisting of:
2,3-dihydro-1,4-dioxinyl, dihydropyranyl, dihydropyrazinyl, dihydropyridazinyl, dihydropyridinyl, dihydropyrimidinyl, furanyl, imidazolyl, imidazolidinyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl wherein each of the heterocyclyl is optionally substituted with 1-5 groups independently selected from $C_{1-6}$alkyl, oxo, —C(O)—H, —C(O)—NH$_2$, C(O)—NH—$C_{1-6}$ alkyl, —NH$_2$, and —NH—$C_{1-6}$alkyl.

In one embodiment of the compound disclosed above, or a pharmaceutically acceptable salt thereof:
$R^4$ is selected from the group consisting of (1) H, (2) halogen, and (3) CF$_3$; and
Y is selected from the group consisting of:

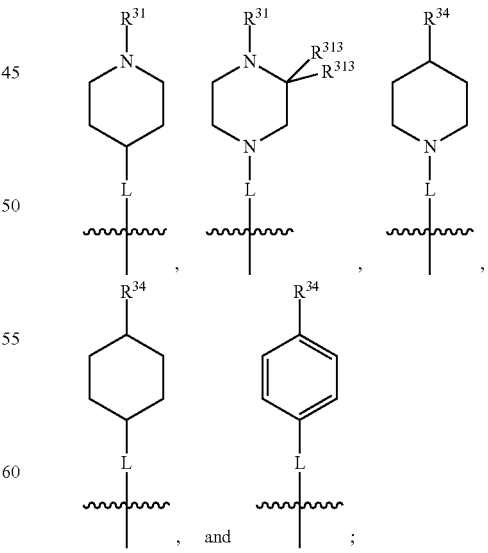

wherein
L is selected from the group consisting of (1) a bond, (2) —NH—, and (3) —NH—C(O)—;

$R^{31}$ is selected from the group consisting of (1) —C(O)—CH$_3$, (2) —S(O)$_2$—CH$_3$, (3) —NH—C(O)—CH$_3$, (4) imidazolidinyl, (5) isoxazolyl, (6) tetrazolyl, and (7) 1,2,3,4-tetrahydropyrimidinyl; wherein each of (4), (5), (6) and (7) is optionally substituted with 1-5 groups independently selected from C$_{1-6}$alkyl, oxo, —C(O)—H, —C(O)—NH$_2$, C(O)—NH—C$_{1-6}$ alkyl, —NH$_2$, and —NH—C$_{1-6}$alkyl;

$R^{34}$ is selected from the group consisting of (1) H, (2) —C(O)—CH$_3$, (3) —S(O)$_2$—CH$_3$, (4) —NH—C(O)—CH$_3$, (5) imidazolidinyl, (6) isoxazolyl, (7) tetrazolyl, and (8) 1,2,3,4-tetrahydropyrimidinyl; wherein each of (5), (6), (7) and (8) is optionally substituted with 1-5 groups independently selected from C$_{1-6}$alkyl, oxo, —C(O)—H, —C(O)—NH$_2$, C(O)—NH—C$_{1-6}$ alkyl, —NH$_2$, and —NH—C$_{1-6}$alkyl;

each occurrence of $R^{313}$ is independently selected from the group consisting of (1) H, (2) methyl, (3) ethyl and (4) propyl. In one embodiment, each $R^{313}$ is independently H or methyl.

Thus, the present invention provides a TDO or IDO inhibitor compound for use in medicine, which compound comprises a formula selected from one of the following:

1001

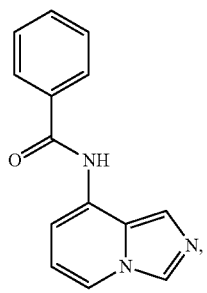

1002

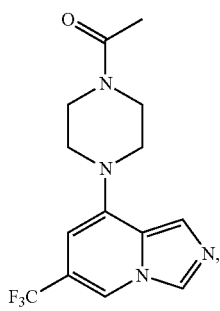

1003

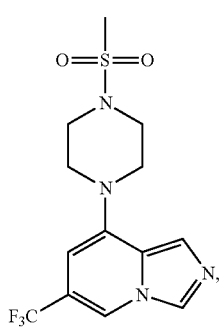

1004

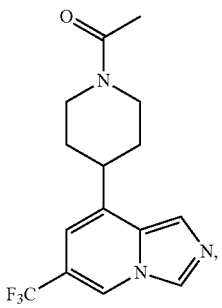

1005

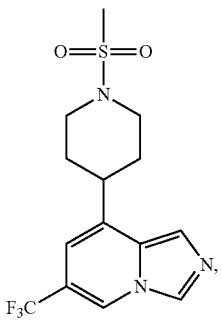

1006

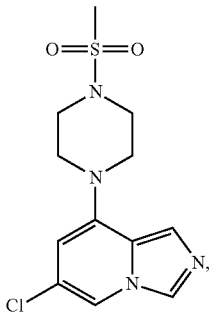

1007

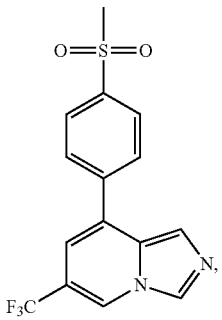

1008

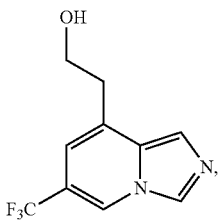

-continued
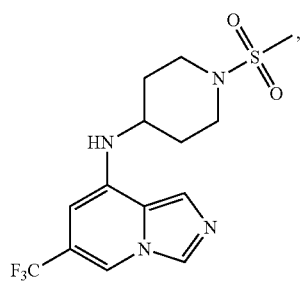
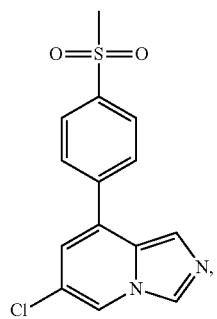
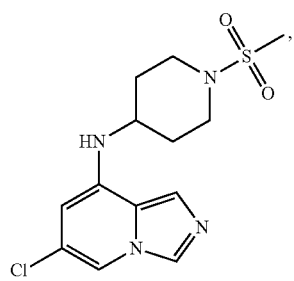
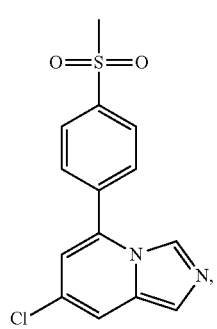
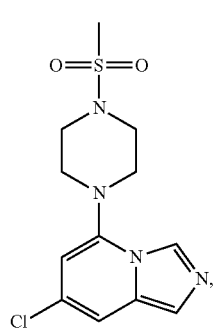
-continued
1009 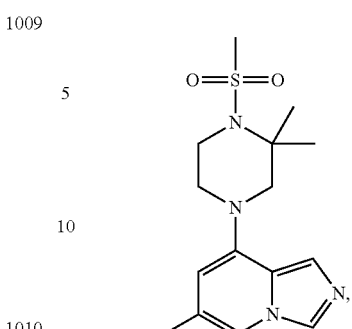
1010
1011 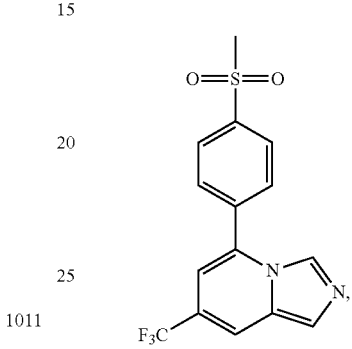
1012 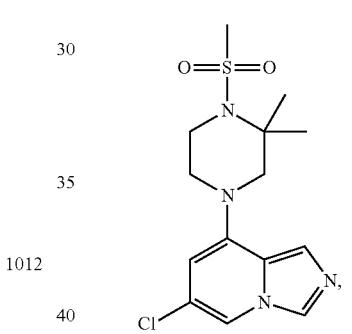
1013 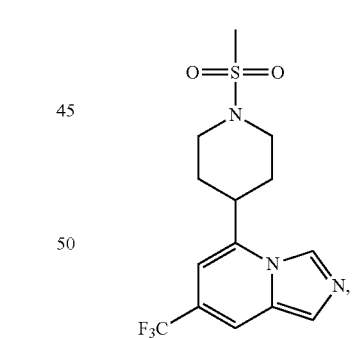
1014
1015
1016
1017
1018 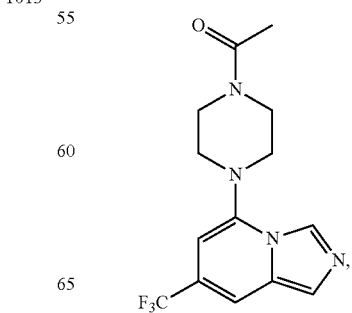

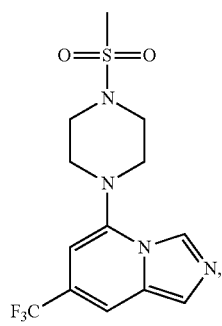
1019
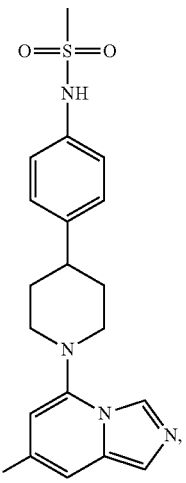
1023
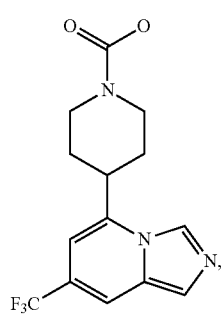
1020
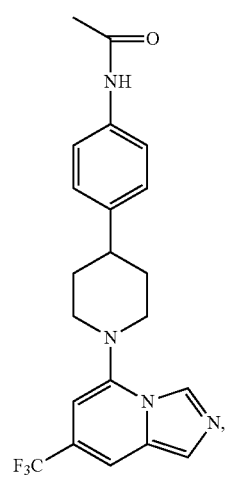
1024
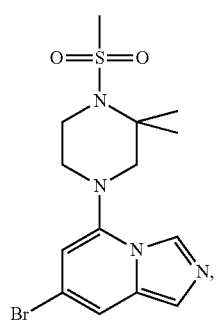
1021
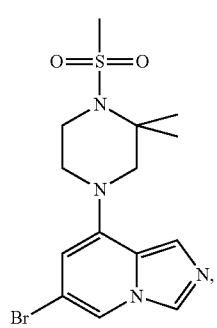
1022
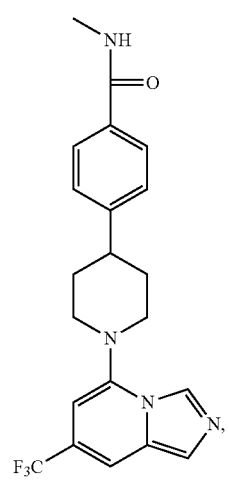
1025

-continued
1026 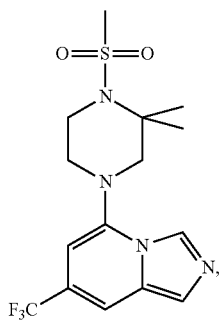
1027 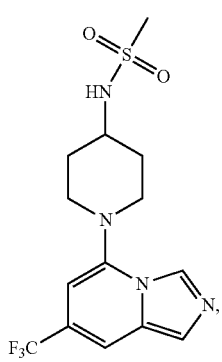
1028 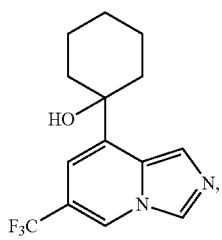
1029 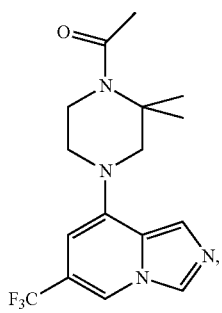
1030 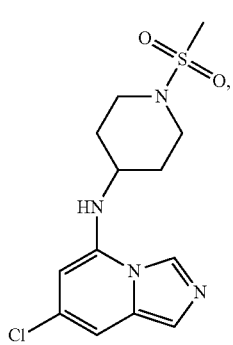
-continued
1031 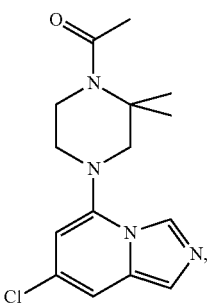
1032 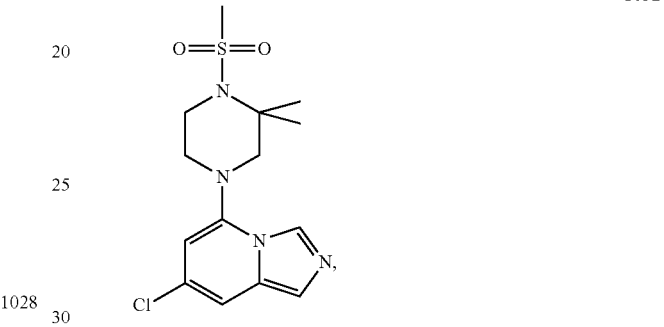
1033 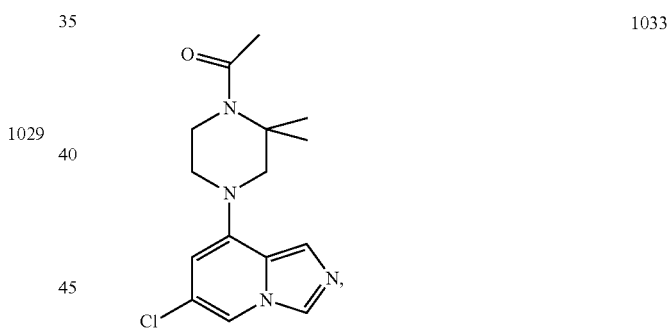
1034 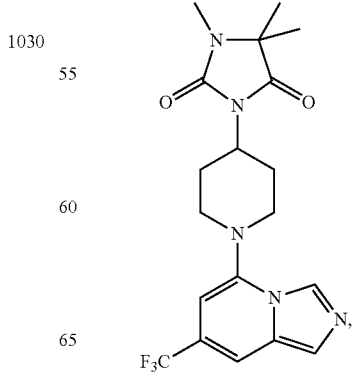

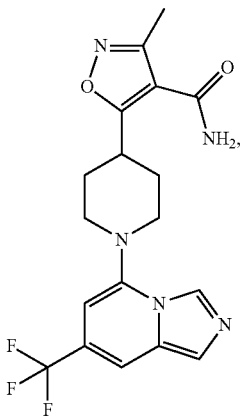
1035

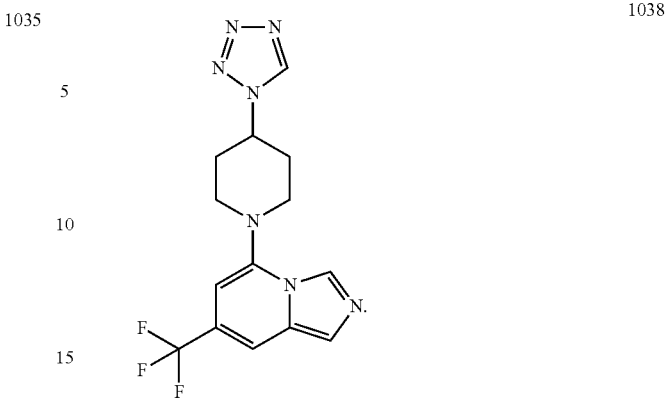
1038

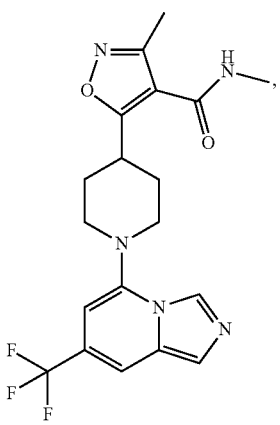
1036

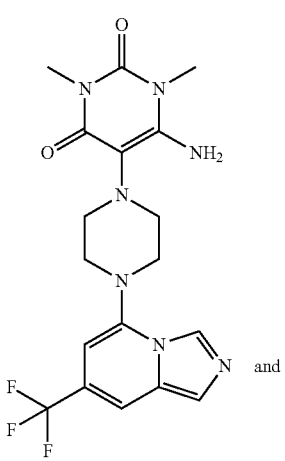 and

1037

Typically, the above formulae (and all formulae herein) are shown in non-stereoisomeric form. For the avoidance of doubt, throughout the present disclosure a single formula is intended to represent all possible stereoisomers of a particular structure, including all possible isolated enantiomers corresponding to the formula, all possible mixtures of enantiomers corresponding to the formula, all possible mixtures of diastereomers corresponding to the formula, all possible mixtures of epimers corresponding to the formula and all possible racemic mixtures corresponding to the formula. In addition to this, the above formulae (and all formulae herein) are intended to represent all tautomeric forms equivalent to the corresponding formula.

Pharmacological inhibitors of TDO and/or IDO have utility in a wide range of indications, including Infectious diseases, cancer, neurological conditions and many other diseases.

Infectious diseases and inflammation—Infection by bacteria, parasites, or viruses induces a strong IFN-γ-dependent inflammatory response. IDO can dampen protective host immunity, thus indirectly leading to increased pathogen burdens. For example, IDO activity attenuates *Toxoplasma gondii* replication in the lung, and the inflammatory damage is significantly decreased by the administration of the IDO inhibitor 1MT after infection (Murakami et al., 2012). Also, in mice infected with murine leukaemia virus (MuLV), IDO was found to be highly expressed, and ablation of IDO enhanced control of viral replication and increased survival (Hoshi et al., 2010). In a model of influenza infection, the immunosuppressive effects of IDO could predispose lungs to secondary bacterial infection (van der Sluijs., et al 2006). In Chagas Disease, which is caused by the *Trypanosoma cruzi* parasite, kynurenine is increased in patients and correlates with disease severity (Maranon et al., 2013). Therefore, IDO inhibitors could be used to improve the outcomes of patients with a wide variety of infectious diseases and inflammatory conditions. Given the role of TDO in controlling systemic Trp levels, TDO inhibitors could also be used to improve the outcomes of patients with a wide variety of infectious diseases and inflammatory conditions.

IDO and immunity to gut bacteria—IDO plays a role in regulating mucosal immunity to the intestinal microbiota. IDO has been shown to regulate commensal induced antibody production in the gut; IDO-deficient mice had elevated baseline levels of immunoglobulin A (IgA) and immunoglobulin G (IgG) in the serum and increased IgA in intestinal secretions. Due to elevated antibody production, IDO deficient mice were more resistant to intestinal colonization by the gram-negative enteric bacterial pathogen *Citrobacter*

*rodentium* than WT mice. IDO-deficient mice also displayed enhanced resistance to the colitis caused by infection with *C. rodentium* (Harrington et al., 2008).

Therefore, pharmacological targeting of IDO activity may represent a new approach to manipulating intestinal immunity and controlling the pathology caused by enteric pathogens including colitis (Harrington et al., 2008).

HIV infection—Patients infected with HIV have chronically reduced levels of plasma tryptophan and increased levels of kynurenine, and increased IDO expression (Fuchs et al., 1990 and Zangerle et al., 2002).

In HIV patients the upregulation of IDO acts to suppress immune responses to HIV antigens contributing to the immune evasion of the virus. HIV triggers high levels of IDO expression when it infects human macrophages in vitro (Grant et al., 2000), and simian immunodeficiency virus (SIV) infection of the brain in vivo induces IDO expression by cells of the macrophage lineage (Burudi et al., 2002).

The pathogenesis of HIV is characterized by CD4+ T cell depletion and chronic T cell activation, leading ultimately to AIDS (Douek et al., 2009). CD4+ T helper (TH) cells provide protective immunity and immune regulation through different immune cell functional subsets, including TH1, TH2, T regulatory (Treg), and TH17 cells. Progressive HIV is associated with the loss of TH17 cells and a reciprocal increase in the fraction of the immunosuppressive Treg cells. The loss of TH17/Treg balance is associated with induction of IDO by myeloid antigen-presenting dendritic cells (Favre et al., 2010). In vitro, the loss of TH17/Treg balance is mediated directly by the proximal tryptophan catabolite from IDO metabolism, 3-hydroxyanthranilic acid. Therefore in progressive HIV, induction of IDO contributes to the inversion of the TH17/Treg balance and maintenance of a chronic inflammatory state (Favre et al., 2010). Therefore, IDO inhibitors could have utility in addressing the TH17/Treg balance in HIV.

Sepsis-induced hypotension—Systemic inflammation such as sepsis is characterized by arterial hypotension and systemic inflammatory response syndrome (Riedemann et al., 2003). The associated increase in circulating pro-inflammatory cytokines, including interferon-γ (IFN-γ), leads to the unchecked production of effector molecules such as reactive oxygen and nitrogen species that themselves can contribute to pathology (Riedemann et al., 2003).

The metabolism of tryptophan to kynurenine by IDO expressed in endothelial cells contributes to arterial vessel relaxation and the control of blood pressure (Wang et al., 2010). Infection of mice with malarial parasites (*Plasmodium berghei*), and experimental induction of endotoxemia, caused endothelial expression of IDO, resulting in decreased plasma tryptophan, increased kynurenine, and hypotension. Pharmacological inhibition of IDO increased blood pressure in systemically inflamed mice, but not in mice deficient for IDO or interferon-γ, which is required for IDO induction. Arterial relaxation by kynurenine was mediated by activation of the adenylate and soluble guanylate cyclase pathways. (Wang et al., 2010). Therefore, inhibitors of IDO (and TDO, given its role in controlling systemic Trp levels) could have utility in treating sepsis-induced hypotension.

Figure 2:
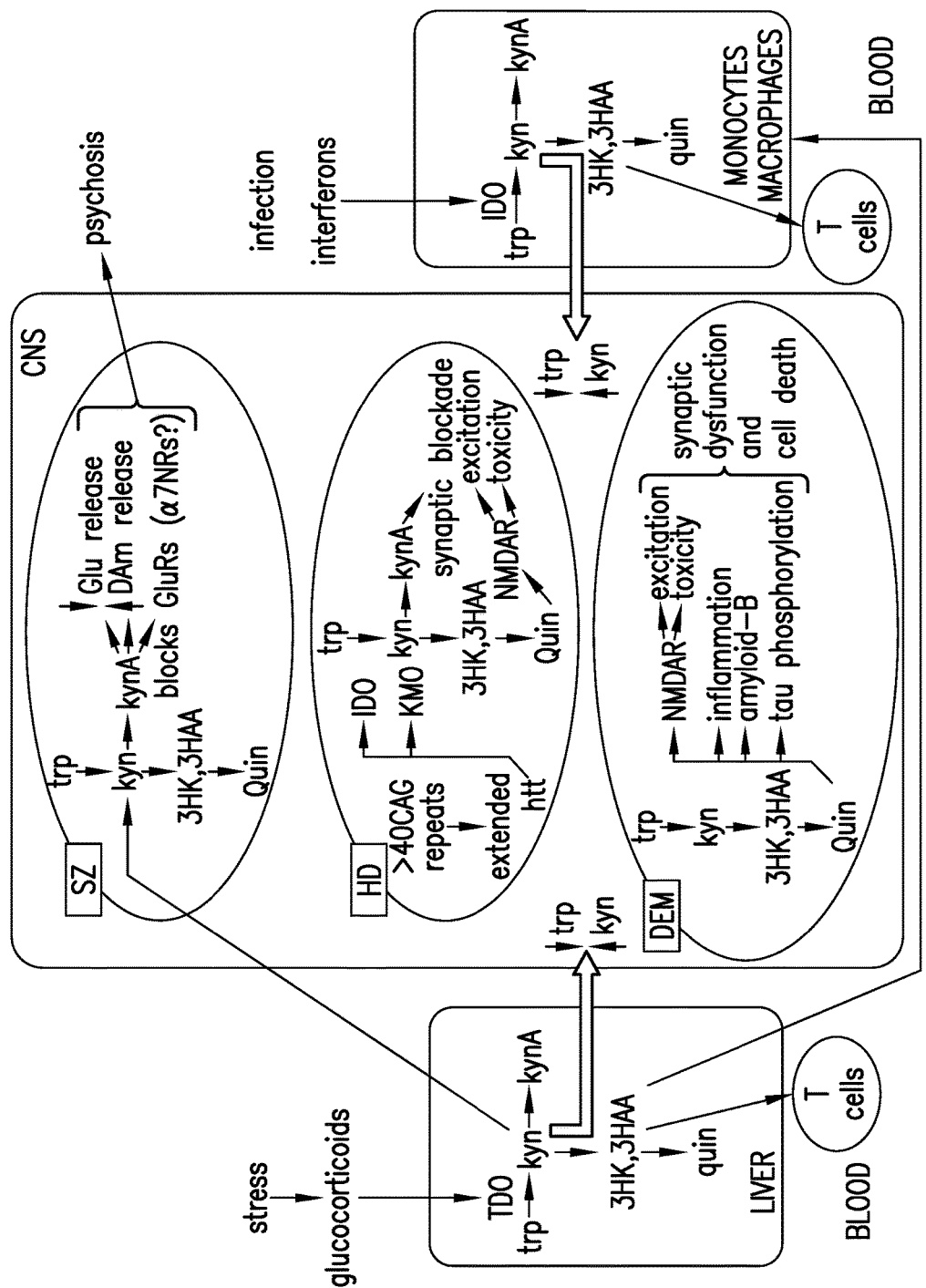
FIG. 2 shows a schematic summary of the involvement of kynurenine in CNS disorder (also see Stone and Darlington. Br. J. Pharmacol. 2013 169(6):1211-27).

CNS disorders—In the central nervous system both fates of TRP which act as a precursor to kynurenine and serotonin are pathways of interest and importance. Metabolites produced by the kynurenine pathway have been implicated to play a role in the pathomechanism of neuroinflammatory and neurodegenerative disorder (summarised in FIG. 2). The first stable intermediate from the kynurenine pathway is KYN. Subsequently, several neuroactive intermediates are generated. They include kynurenic acid (KYNA), 3-hydroxykynurenine (3-HK), and quinolinic acid (QUIN). 3-HK and QUIN are neurotoxic by distinct mechanisms; 3-HK is a potent free-radical generator (Hiraku et al., 1995; Ishii et al., 1992; Thevandavakkam et al., 2010), whereas QUIN is an excitotoxic N-methyl-D-aspartate (NMDA) receptor agonist (Schwarcz et al., 1983; Stone and Perkins, 1981). KYNA, on the other hand, has neuroprotective properties as an antagonist of excitatory amino acid receptors and a free-radical scavenger (Carpenedo et al., 2001; Foster et al., 1984; Goda et al., 1999; Vecsei and Beal, 1990). Changes in the concentration levels of kynurenines can shift the balance to pathological conditions. The ability to influence the metabolism towards the neuroprotective branch of the kynurenine pathway, i.e. towards kynurenic acid (KYNA) synthesis, may be one option in preventing neurodegenerative diseases.

In the CNS, the kynurenine pathway is present to varying extents in most cell types, Infiltrating macrophages, activated microglia and neurons have the complete repertoire of kynurenine pathway enzymes. On the other hand, neuroprotective astrocytes and oligodendrocytes lack the enzyme, kynurenine 3-monooxygenase (KMO) and IDO respectively, and are incapable of synthesizing the excitotoxin, quinolinic acid (QUIN) (Guillemin et al., 2000; Lim et al., 2007). TDO is expressed in low quantities in the brain, and is induced by TRP or corticosteroids (Salter and Pogson 1985; Miller et al., 2004).

Given the role of TDO and IDO in the pathogenesis of several CNS disorders as well as the role of TDO in controlling systemic Trp levels, IDO and/or TDO inhibitors could be used to improve the outcomes of patients with a wide variety of CNS diseases and neurodegeneration.

Amyotrophic lateral sclerosis—Amyotrophic lateral sclerosis (ALS), or Lou Gehrig's disease, is a progressive and fatal neurodegenerative disease targeting the motor system. ALS results in the selective attacking and destruction of motor neurons in the motor cortex, brainstem and spinal cord.

Although multiple mechanisms are likely to contribute to ALS, the kynurenine pathway activated during neuroinflammation is emerging as a contributing factor. Initial inflammation may inflict a nonlethal injury to motor neurons of individuals with a susceptible genetic constitution, in turn triggering a progressive inflammatory process which activates microglia to produce neurotoxic kynurenine metabolites that further destroy motor neurons.

In the brain and spinal cord of ALS patients large numbers of activated microglia, reactive astrocytes, T cells and infiltrating macrophages have been observed (Graves et al., 2004; Henkel et al., 2004). These cells release inflammatory and neurotoxic mediators, among others IFN-γ, the most potent inducer of IDO (McGeer and McGeer 2002). The neuronal and microglial expression of IDO is increased in ALS motor cortex and spinal cord (Chen et al., 2010). It has been proposed that the release of immune activating agents activates the rate-limiting enzyme of the KP, IDO, which generates metabolites such as the neurotoxin QUIN. Therefore, inhibition of IDO would reduce the synthesis of neurotoxic QUIN, which has been clearly implicated in the pathogenesis of ALS.

Huntington's disease—Huntington's disease (HD) is a genetic autosomal dominant neurodegenerative disorder caused by expansion of the CAG repeats in the huntingtin (htt) gene. Patients affected by HD display progressive motor dysfunctions characterized by abnormality of voluntary and involuntary movements (choreoathetosis) and psychiatric and cognitive disturbances. In-life monitoring of metabolites within the KYN pathway provide one of the few biomarkers that correlates with the number of CAG repeats and hence the severity of the disorder (Forrest et al., 2010). Post mortem very high levels of QUIN are found located in areas of neurodegeneration, while striatal glutamatergic neurones, on which QUIN acts as an excitotoxin, are a principal class lost in the disease. Importantly, TDO ablation in a *Drosophila* model of Huntington's disease ameliorated neurodegeneration (Campesan et al., 2011).

Alzheimer's disease—Alzheimer's disease (AD) is an age-related neurodegenerative disorder characterised by neuronal loss and dementia. The histopathology of the disease is manifested by the accumulation of intracellular β1-amyloid (Aβ) and subsequent formation of neuritic plaques as well as the presence of neurofibrillary tangles in specific brain regions associated with learning and memory. The pathological mechanisms underlying this disease are still controversial, however, there is growing evidence implicating KP metabolites in the development and progression of AD.

It has been shown that Aβ (1-42) can activate primary cultured microglia and induce IDO expression (Guillemin et al., 2003; Walker et al., 2006). Furthermore, IDO overexpression and increased production of QUIN have been observed in microglia associated with the amyloid plaques in the brain of AD patients (Guillemin et al., 2005). QUIN has been shown to lead to tau hyperphosphorylation in human cortical neurons (Rahman et al., 2009). Thus, overexpression of IDO and over-activation of the KP in microglia are implicated in the pathogenesis of AD.

There is also evidence for TDO involvement in Alzheimer's disease. TDO is upregulated in the brain of patients and AD mice models. Furthermore, TDO co-localizes with quinolinic acid, neurofibrillary tangles-tau and amyloid deposits in the hippocampus of AD patients (Wu et al., 2013). Therefore, the kynurenine pathway is over-activated in AD by both TDO and IDO and may be involved in neurofibrillary tangle formation and associated with senile plaque formation.

Psychiatric disorders and pain—Most tryptophan is processed through the kynurenine pathway. A small proportion of tryptophan is processed to 5-HT and hence to melatonin, both of which are also substrates for IDO. It has long been known that amongst other effects acute tryptophan depletion can trigger a depressive episode and produces a profound change in mood even in healthy individuals. These observations link well with the clinical benefits of serotonergic drugs both to enhance mood and stimulate neurogenesis.

The co-morbidity of depressive symptoms, implication of the kynurenine pathway in inflammation and an emerging link between TDO and the glucocorticoid mediated stress response also implicate a role in the treatment of chronic pain (Stone and Darlington 2013). Schizophrenic patients exhibit elevated KYN levels both in CSF and brain tissue, particularly the frontal cortex. This has been associated with the "hypofrontality" observed in schizophrenia. Indeed rodents treated with neuroleptics show a marked reduction in frontal KYN levels. These changes have been associated with reduced KMO and 3HAO. Evidence includes an association between a KMO polymorphism, elevated CSF KYN and schizophrenia (Holtze etr al., 2012). Taken together there is potential for manipulations in this pathway to be both pro-cognate and neuroleptic.

Pain and depression are frequently comorbid disorders. It has been shown that IDO plays a key role in this comorbidity. Recent studies have shown that IDO activity is linked to (a) decreased serotonin content and depression (Dantzer et al., 2008; Sullivan et al., 1992) and (b) increased kynurenine content and neuroplastic changes through the effect of its derivatives such as quinolinic acid on glutamate receptors (Heyes et al., 1992).

In rats chronic pain induced depressive behaviour and IDO upregulation in the bilateral hippocampus. Upregulation of IDO resulted in the increased kynurenine/tryptophan ratio and decreased serotonin/tryptophan ratio in the bilateral hippocampus. Furthermore, IDO gene knockout or pharmacological inhibition of hippocampal IDO activity attenuated both nociceptive and depressive behaviour (Kim et al., 2012).

Since proinflammatory cytokines have been implicated in the pathophysiology of both pain and depression, the regulation of brain IDO by proinflammatory cytokines serves as a critical mechanistic link in the comorbid relationship between pain and depression through the regulation of tryptophan metabolism.

Multiple sclerosis—Multiple sclerosis (MS) is an autoimmune disease characterized by inflammatory lesions in the white matter of the nervous system, consisting of a specific immune response to the myelin sheet resulting in inflammation and axonal loss (Trapp et al., 1999; Owens, 2003).

Accumulation of neurotoxic kynurenine metabolites caused by the activation of the immune system is implicated in the pathogenesis of MS. QUIN was found to be selectively elevated in the spinal cords of rats with EAE, an autoimmune animal model of MS (Flanagan et al., 1995). The origin of the increased QUIN in EAE was suggested to be the macrophages. QUIN is an initiator of lipid peroxidation and high local levels of QUIN near myelin may contribute to the demyelination in EAE and possibly MS.

Interferon beta 1b (IFN-β1b) induces KP metabolism in macrophages at concentrations comparable to those found in the sera of IFN-b treated patients, this which may be a limiting factor in its efficacy in the treatment of MS (Guillemin et al., 2001). After IFN-β administration, increased kynurenine levels and kynurenine/tryptophan ratio were found in the plasma of MS patients receiving IFN-b injection compared to healthy subjects indicating an induction of IDO by IFN-β (Amirkhani et al., 2005). IFN-β1b, leads to production of QUIN at concentrations sufficient to disturb the ability of neuronal dendrites to integrate incoming signals and kill oligodendrocytes (Cammer 2001). In IFN-β1b-treated patients concomitant blockade of the KP with an IDO/TDO inhibitor may improve its efficacy of IFN-β1b.

Parkinson's disease—Parkinson's disease (PD) is a common neurodegenerative disorder characterised by loss of dopaminergic neurons and localized neuroinflammation.

Parkinson's disease is associated with chronic activation of microglia (Gao and Hong, 2008). Microglia activation release neurotoxic substances including reactive oxygen species (ROS) and proinflammatory cytokines such as INF-γ (Block et al., 2007), a potent activator of KP via induction of IDO expression. KP in activated microglia leads to upregulation of 3HK and QUIN. 3HK is toxic primarily as a result of conversion to ROS (Okuda et al., 1998). The combined effects of ROS and NMDA receptor-mediated excitotoxicity by QUIN contribute to the dysfunction of neurons and their death (Braidy et al., 2009; Stone and Perkins, 1981). However, picolinic acid (PIC) produced through KP activation in neurons, has the ability to protect neurons against QUIN-induced neurotoxicity, being NMDA agonist (Jhamandas et al., 1990). Microglia can become overactivated, by proinflammatory mediators and stimuli from dying neurons and cause perpetuating cycle of further microglia activation microgliosis. Excessive microgliosis will cause neurotoxicity to neighbouring neurons and resulting in neuronal death, contributing to progression of Parkinson's disease. (Zinger et al 2011): Therefore, PD is associated with an imbalance between the two main branches of the KP within the brain. KYNA synthesis by astrocytes is decreased and concomitantly, QUIN production by microglia is increased.

HIV—HIV patients, particularly those with HIV-linked dementia (Kandanearatchi & Brew 2012), often have significantly elevated KYN levels in CSF. These levels are directly related to the development of neurocognitive decline and often the presence of sever psychotic symptoms (Stone & Darlington 2013).

Cancer—It is clear that tumours can induce tolerance to their own antigens. Tryptophan catabolism in cancer is increasingly being recognized as an important micro-environmental factor that suppresses antitumor immune responses. Depletion of tryptophan and accumulation of immunosuppressive tryptophan catabolites such as kynurenine create an immunosuppressive milieu in tumours and in tumour-draining lymph nodes by inducing T-cell anergy and apoptosis. Such immunosuppression in the tumour microenvironment may help cancers evade the immune response and enhance tumorigenicity (reviewed in Adam et al., 2012).

Recently, both TDO and IDO have been implicated in tumour progression. Individually TDO or IDO have been found to be overexpressed in various cancers, furthermore, several cancers overexpress both TDO and IDO. TDO and IDO mediate immunosuppressive effects through the metabolization of Trp to kynurenine, triggering downstream signalling through GCN2, mTOR and AHR that can affect differentiation and proliferation of T cells. Also, expression of IDO by activated dendritic cells can serve to activate regulatory T cells (Tregs) and inhibit tumor-specific effector CD8+ T cells, thereby constituting a mechanism by which the immune system can restrict excessive lymphocyte reactivity (reviewed in Platten et al., 2012).

IDO—Increased expression of IDO has been shown to be an independent prognostic variable for reduced survival in patients with acute myeloid leukemia (AML), small-cell lung, melanoma, ovarian, colorectal, pancreatic, and endometrial cancers (Okamoto et al., 2005; Ino et al., 2006). Indeed, sera from cancer patients have higher kynurenine/ tryptophan ratios than sera from normal volunteers (Liu et al., 2010; Weinlich et al., 2007; Huang et al., 2002). The level of IDO expression was also shown to correlate with the number of tumour infiltrating lymphocytes in colorectal carcinoma patients (Brandacher et al., 2006).

In preclinical models, transfection of immunogenic tumour cells with recombinant IDO prevented their rejection in mice (Uyttenhove et al., 2003). While, ablation of IDO expression led to a decrease in the incidence and growth of 7,12-dimethylbenz(a)anthraceneinduced premalignant skin papillomas (Muller et al., 2008). Moreover, IDO inhibition slows tumour growth and restores anti-tumour immunity (Koblish et al., 2010) and IDO inhibition synergises with cytotoxic agents, vaccines and cytokines to induce potent anti-tumour activity (Uyttenhove et al., 2003; Muller et al., 2005; Zeng et al., 2009).

TDO—TDO is predominantly expressed in the liver and is believed to regulate systemic Trp concentrations, however, TDO was found to be frequently activated and constitutively expressed in glioma cells. TDO derived KYN was shown to suppress antitumor immune responses and promote tumor-cell survival and motility through the AhR in an autocrine manner (Opitz et al., 2011). It was also shown that TDO is elevated in human hepatocellular carcinomas and detected sporadically in other cancers. In a preclinical model, TDO expression prevented rejection of tumor grafts by preimmunized mice. Systemic administration of the TDO inhibitor, LM10, restored the ability of mice to reject TDO-expressing tumors (Pilotte et al., 2012).

Therefore inhibitors of TDO or IDO could have wide ranging therapeutic efficacy in the treatment of cancer. Also dual inhibitors blocking both TDO and IDO may demonstrate improved clinical efficacy by targeting both of these key Trp-metabolising enzymes and would also treat a wider patient population: in a series of 104 human tumor lines of various histological types, 20 tumors expressed only TDO, 17 expressing only IDO and 16 expressed both. Therefore, targeting both IDO and TDO would allow reaching 51% of tumors instead of 32% with IDO or 35% with TDO alone (Pilotte et al., 2012). Moreover, given the role of TDO in controlling systemic Trp levels, TDO inhibitors could also be used to improve the outcomes of patients with a wide variety of cancers and neoplastic diseases that do not express TDO.

Inhibition of IDO and/or TDO will dramatically lower kynurenine levels, relieving the brake on the immune system allowing it to attack and eliminate tumours. While there is evidence that a TDO/IDO inhibitor would be useful as a stand-alone agent, inhibitors of this type would be particularly effective when used in combination with other cancer immunotherapies. In fact, upregulation of IDO expression has been identified as a mechanism by which tumours gain resistance to the CTLA-4 blocking antibody ipilimumab. Ipilimumab blocks the co-stimulatory molecule CTLA-4, causing tumour-specific T cells to remain in an activated state. IDO knockout mice treated with antiCTLA-4 antibody demonstrate a striking delay in B16 melanoma tumor growth and increased overall survival when compared with wild-type mice. Also, CTLA-4 blockade strongly synergizes with IDO inhibitors to mediate tumour rejection. Similar data was also reported for IDO inhibitors in combination with anti-PD1 and anti-PDL-1 antibodies (Holmgaard et al., 2013).

Agents that will influence an immunosuppressive environment may also be relevant to chimeric antigen receptor T cell therapy (CAR-T) therapies to enhance efficacy and patient responses.

Other Diseases—Although these effects are defensive strategies to cope with infection and inflammation, they may have unintended consequences because kynurenines formed during IDO and TDO-mediated degradation of tryptophan can chemically modify proteins and have been shown to be cytotoxic (Morita et al., 2001; Okuda et al., 1998). In coronary heart disease, inflammation and immune activation are associated with increased blood levels of kynurenine (Wirleitner et al., 2003) possibly via interferon-γ-mediated activation of IDO. In experimental chronic renal failure, activation of IDO leads to increased blood levels of kynurenines (Tankiewicz et al., 2003), and in uremic patients kynurenine-modified proteins are present in urine (Sala et al., 2004). Further, renal IDO expression may be deleterious during inflammation, because it enhances tubular cell injury.

General anaesthesia unfortunately mimics many of these effects inducing stress and inflammatory processes. Post anaesthesia cognitive dysfunction has often been correlated with these sequelae. Recently these deficits have been shown to be correlated with changes in kynurenine pathway markers, but not cytokines, following cardiac surgery and in recovering stroke patients (Stone and Darlington 2013).

Cataracts—A cataract is a clouding of the lens inside the eye that leads to a decrease in vision. Recent studies suggest that kynurenines might chemically alter protein structure in the human lens leading to cataract formation. In the human lens IDO activity is present mainly in the anterior epithelium (Takikawa et al., 1999). Several kynurenines, such as kynurenine (KYN), 3-hydroxykynurenine (3OHKYN), and 3-hydroxykynurenine glucoside (3OHKG) have been detected in the lens; where they were thought to protect the retina by absorbing UV light and therefore are commonly referred to as UV filters. However, several recent studies show that kynurenines are prone to deamination and oxidation to form $\alpha,\beta$-unsaturated ketones that chemically react and modify lens proteins (Taylor et al., 2002). Kynurenine mediated modification could contribute to the lens protein modifications during aging and cataractogenesis. They may also reduce the chaperone function of $\alpha$-crystallin, which is necessary for maintaining lens transparency.

Transgenic mouse lines that overexpress human IDO in the lens developed bilateral cataracts within 3 months of birth. It was demonstrated that IDO-mediated production of kynurenines results in defects in fibre cell differentiation and their apoptosis (Mailankot et al., 2009). Therefore inhibition of IDO may slow the progression of cataract formation.

Female Reproductive Health—Endometriosis

Endometriosis, the presence of endometrium outside the uterine cavity, is a common gynaecological disorder, causing abdominal pain, dyspareunia and infertility. IDO expression was found to be higher in eutopic endometrium from women with endometriosis by microarray analysis (Burney et al., 2007 and Aghajanova et al., 2011). Furthermore, IDO was shown to enhance the survival and invasiveness of endometrial stromal cells (Mei et al., 2013). Therefore, an IDO/TDO inhibitor could be used as a treatment for endometriosis.

Contraception and abortion—The process of implantation of an embryo requires mechanisms that prevent allograft rejection; and tolerance to the fetal allograft represents an important mechanism for maintaining a pregnancy. Cells expressing IDO in the foeto-maternal interface protect the allogeneic foetus from lethal rejection by maternal immune responses. Inhibition of IDO by exposure of pregnant mice to 1-methyl-tryptophan induced a T cell-mediated rejection of allogeneic concepti, whereas syngeneic concepti were not affected; this suggests that IDO expression at the foetal—maternal interface is necessary to prevent rejection of the foetal allograft (Munn et al., 1998). Accumulating evidence indicates that IDO production and normal function at the foetal—maternal interface may play a prominent role in pregnancy tolerance (Durr and Kindler, 2013). Therefore, an IDO/TDO inhibitor could be used as a contraceptive or abortive agent.

On the above basis, the inventors have determined that a strong rationale exists for the therapeutic utility of drugs which block the activity of TDO and or IDO, in treating the above-mentioned diseases, conditions and disorders.

Having regard to the above, it is an aim of the present invention to provide TDO or IDO inhibitors, and in particular TDO and IDO inhibitors for use in medicine. It is a further aim to provide pharmaceutical compositions comprising such inhibitors, and in particular to provide compounds and pharmaceutical compositions for treating a cancer, an inflammatory condition, an infectious disease, a central nervous system disease or disorder and other diseases, conditions and disorders. It is also an aim to provide methods of synthesis of the compounds.

In the context of the present invention, the medicinal use is not especially limited, provided that it is a use which is facilitated by the TDO and/or the IDO inhibitory effect of the compound. Thus, the compounds of the invention may be for use in any disease, condition or disorder that may be prevented, ameliorated or treated using a TDO and/or IDO inhibitor. Typically this comprises a disease condition and/or a disorder selected from: a cancer, an inflammatory condition, an infectious disease, a central nervous system disease or disorder, coronary heart disease, chronic renal failure, post anaesthesia cognitive dysfunction, a disease condition and/or a disorder relating to female reproductive health including contraception or abortion, and cataracts.

When the disease, condition or disorder is an inflammatory disease, condition or disorder, it is not especially limited, provided that the disease, condition or disorder is one which may be treated, prevented or ameliorated by using a TDO and/or IDO inhibitor. However, typically the inflammatory condition is a condition relating to immune B cell T cell, dendritic cell, natural killer cell, macrophage, and/or neutrophil dysregulation.

When the disease, condition or disorder is a cancer, it is not especially limited, provided that the cancer is one which may be treated, prevented or ameliorated by using a TDO and/or IDO inhibitor. Thus the cancer may be a cancer selected from: a solid or liquid tumour including cancer of the eye, brain (such as gliomas, glioblastomas, medullablastomas, craniopharyngioma, ependymoma, and astrocytoma), spinal cord, kidney, mouth, lip, throat, oral cavity, nasal cavity, small intestine, colon, parathyroid gland, gall bladder, head and neck, breast, bone, bile duct, cervix, heart, hypopharyngeal gland, lung, bronchus, liver, skin, ureter, urethra, testicles, vagina, anus, laryngeal gland, ovary, thyroid, oesophagus, nasopharyngeal gland, pituitary gland, salivary gland, prostate, pancreas, adrenal glands; an endometrial cancer, oral cancer, melanoma, neuroblastoma, gastric cancer, an angiomatosis, a hemangioblastoma, a pheochromocytoma, a pancreatic cyst, a renal cell carcinoma, Wilms' tumour, squamous cell carcinoma, sarcoma, osteosarcoma, Kaposi sarcoma, rhabdomyosarcoma, hepatocellular carcinoma, PTEN Hamartoma-Tumor Syndromes (PHTS) (such as Lhermitte-Duclos disease, Cowden syndrome, *Proteus* syndrome, and *Proteus*-like syndrome), leukaemias and lymphomas (such as acute lymphoblastic leukaemia, chronic lymphocytic leukaemia, acute myelogenous leukaemia, chronic myelogenous leukaemia, hairy cell leukaemia, T-cell prolymphocytic leukemia (T-PLL), large granular lymphocytic leukemia, adult T-cell leukemia, juvenile myelomonocytic leukaemia, Hodgkin lymphoma, non-Hodgkin lymphoma, mantle lymphoma, follicular lymphoma, primary effusion lymphoma, AIDS-related lymphoma, Hodgkin lymphoma, diffuse B cell lymphoma, Burkitt lymphoma, and cutaneous T-cell lymphoma). However, when the compound is an IDO inhibitor, typically (but not exclusively) the cancer is a cancer selected from acute myeloid leukemia (AML), a small-cell lung cancer, a melanoma, an ovarian cancer, a colorectal cancer, a pancreatic cancer, an endometrial cancer, and a skin papilloma. When the compound is a TDO inhibitor, typically (but not exclusively) the cancer is a cancer selected from a glioma, and a hepatocellular carcinoma.

When the disease is an infectious disease, it is not especially limited, provided that the disease is one which may be treated, prevented or ameliorated by using a TDO and/or IDO inhibitor. However, typically the infectious disease is selected from a bacterial infection and a viral infection, preferably a gut infection, sepsis, and sepsis induced hypotension.

When the disease, condition or disorder is a central nervous system disease, condition or disorder, it is not especially limited, provided that the disease, condition or disorder is one which may be treated, prevented or ameliorated by using a TDO and/or IDO inhibitor. However, the central nervous system disease, condition or disorder is typically selected from amyotrophic lateral sclerosis (AML), Huntington's disease, Alzheimer's disease, pain, a psychiatric disorder, multiple sclerosis, Parkinson's disease, and HIV related neurocognitive decline.

When the disease, condition or disorder is one relating to female reproductive health, it is not especially limited provided that the disease, condition or disorder is one which may be treated, prevented or ameliorated by using a TDO and/or IDO inhibitor. In typical embodiments the disease, condition or disorder is selected from gynaecological disorders such as endometriosis. Conditions relating to female reproductive health that are included in the invention include contraception and abortion such that the compounds of the invention may be used as a contraceptive and/or abortive agent.

The present invention also provides a pharmaceutical composition comprising a compound as defined above. Whilst the pharmaceutical composition is not especially limited, typically the composition further comprises a pharmaceutically acceptable additive and/or excipient. In the pharmaceutical composition, the compound as defined above may be present in the form described above, but may alternatively be in a form suitable for improving bioavailability, solubility, and/or activity, and/or may be in a form suitable for improving formulation. Thus, the compound may be in the form of a pharmaceutically acceptable salt, hydrate, acid, ester, or other alternative suitable form. Typically, the composition is for treating a disease, condition or disorder as defined above. In some instances, the compound may be present in the composition as a pharmaceutically acceptable salt, or other alternative form of the compound, in order to ameliorate pharmaceutical formulation.

In some embodiments the pharmaceutical composition is a composition for treating a cancer, further comprising a further agent for treating cancer. The further agent for treating cancer is not especially limited, provided that it affords some utility for cancer treatment. However, typically the further agent for treating cancer is selected from anti-microtubule agents, platinum coordination complexes, alkylating agents, antibiotic agents, topoisomerase II inhibitors, antimetabolites, topoisomerase I inhibitors, hormones and hormone analogues, signal transduction pathway inhibitors, non-receptor tyrosine kinase angiogenesis inhibitors, immunotherapeutic agents, proapoptotic agents and cell cycle signalling inhibitors. An immunotherapeutic agent may consist of but is not limited to an anti-tumour vaccine, an oncolytic virus, an immune stimulatory antibody such as anti-CTLA4, anti-PD1, anti-PDL-1, anti-OX40, anti-41BB, anti-CD27, anti-CD40, anti-LAG3, anti-TIM3, and anti-GITR, a novel adjuvant, a peptide, a cytokine, a chimeric antigen receptor T cell therapy (CAR-T), a small molecule immune modulator, tumour microenvironment modulators, and anti-angiogenic agents.

In still further embodiments the invention provides a pharmaceutical kit for treating a cancer, which pharmaceutical kit comprises:

(a) a compound as defined above; and
(b) a further agent for treating cancer; preferably wherein the further agent for treating cancer is selected from anti-microtubule agents, platinum coordination complexes, alkylating agents, antibiotic agents, topoisomerase II inhibitors, antimetabolites, topoisomerase I inhibitors, hormones and hormone analogues, signal transduction pathway inhibitors, non-receptor tyrosine kinase angiogenesis inhibitors, immunotherapeutic agents, proapoptotic agents and cell cycle signalling inhibitors; wherein the compound and the further agent are suitable for administration simultaneously, sequentially or separately.

Further provided by the invention is a method of treating a disease and/or a condition and/or a disorder, which method comprises administering to a patient (or subject) a compound, or a composition, or a kit as defined above. The method is typically a method for treating any disease condition or disorder mentioned herein. In typical embodiments, the method is a method for treating a cancer. Preferably such a method comprises administering to a patient (or subject) a compound or a composition as defined above and a further agent for treating cancer as defined above. The compound or composition and the further agent may administered simultaneously, sequentially or separately, depending upon the agents and patients involved, and the type of cancer indicated.

Typically, in all embodiments of the invention, both above and below, the patient (or subject) is an animal, typically a mammal, and more typically a human.

In addition to compounds for use in medicine, the present invention, and in particular the synthetic method, provides compounds that were not previously known, such compounds comprising a formula selected from compounds 1001 to compound 1038.

Typically, the above formulae (and all formulae herein) are shown in non-stereoisomeric form. For the avoidance of doubt, throughout the present disclosure a single formula is intended to represent all possible stereoisomers of a particular structure, including all possible isolated enantiomers corresponding to the formula, all possible mixtures of enantiomers corresponding to the formula, all possible mixtures of diastereomers corresponding to the formula, all possible mixtures of epimers corresponding to the formula and all possible racemic mixtures corresponding to the formula. In addition to this, the above formulae (and all formulae herein) are intended to represent all tautomeric forms equivalent to the corresponding formula.

Further provided by the invention is a method of synthesis of novel compounds, as defined above, which method comprises a step of reacting a compound having one of the following formulae:

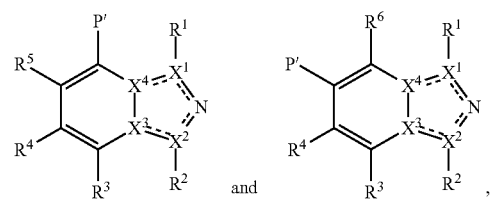

wherein the groups R and X are as in any one of the novel compounds defined herein, and wherein P' is a precursor group to group Y, in order to form the group Y from P' and produce a compound having one of the following formulae:

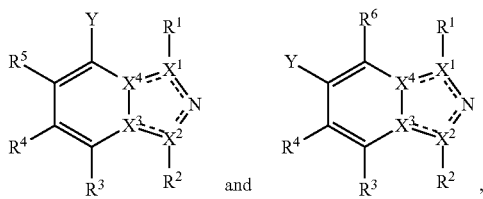

wherein the groups R, Y and X are as in any one of the novel compounds defined herein. The precursor group P' is not especially limited. Typically it is a group which may be displaced from the 6-membered ring in favour of the group Y, or a group which may be converted into a group Y without being displaced from the ring. Typically P' is a halogen, such as —Br or —Cl.

The skilled person may select the type of reagents, and the reaction conditions, with reference to known synthesis techniques. In some embodiments, the method comprises one or more additional substitution steps. Exemplary syntheses are shown in the Examples.

Polymorphism

A compound disclosed herein, for example, that of formula (I), (Ia), (Ib), (Ic) or (Id) including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I), (Ia), (Ib), (Ic) or (Id).

Optical Isomers—Diastereomers—Geometric Isomers—Tautomers

Included herein are various isomers of the compounds disclosed herein, including those of formula (I), (Ia), (Ib), (Ic) or (Id). The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound of formula (I), (Ia), (Ib), (Ic) or (Id) may have one or more asymmetric carbon atom and may occur as a racemic mixture or as individual enantiomers or diastereomers. All such isomeric forms are included herein, including mixtures thereof. If a compound of formula (I), (Ia), (Ib), (Ic) or (Id) contains a double bond, the substituent may be in the E or Z configuration. If a compound of formula (I), (Ia), (Ib), (Ic) or (Id) contains a disubstituted cycloalkyl, the cycloalkyl substituent may have a cis- or trans-configuration.

Any asymmetric atom (e.g., carbon) of a compound of formula (I), (Ia), (Ib), (Ic) or (Id) can be present in racemic mixture or enantiomerically enriched, for example the (R)—, (S)— or (R,S)— configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)— or (S)— configuration. Substituents at atoms with unsaturated double bonds may, if possible, be present in cis-(Z)- or trans-(E)-form.

A compound of formula (I), (Ia), (Ib), (Ic) or (Id) can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds disclosed herein, including those of formula (I), (Ia), (Ib), (Ic) or (Id) include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$, $^{11}C$, $^{13}C$, $^{14}C$, $^{13}N$, $^{15}N$, $^{15}O$, $^{17}O$, $^{18}O$, $^{32}F$, $^{35}S$, $^{18}F$, $^{123}I$, $^{125}I$ and $^{36}Cl$. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}C$, $^{18}F$, $^{15}O$ and $^{13}N$, may be particularly desirable for PET or SPECT studies.

Isotopically-labeled compounds of formula (I), (Ia), (Ib), (Ic) or (Id) can generally be prepared by conventional techniques known to those skilled in the art. Furthermore, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of formula (I), (Ia), (Ib), (Ic) or (Id) is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

Compounds disclosed herein may be useful in the potential treatment or prevention of IDO- and/or TDO-associated diseases. In one embodiment, these compounds may potentially inhibit the activity of the IDO enzyme, TDO enzyme or both IDO and TDO enzymes.

For example, the compounds disclosed herein can potentially be used to inhibit the activity of IDO and/or TDO in cells or in an individual in need of modulation of the enzyme by administering an effective amount of a compound. Further disclosed herein are methods of inhibiting the degradation of tryptophan in a system containing cells expressing IDO and/or TDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO- and/or TDO-mediated immunosuppression in a patient by administering to the patient an effective amount of a compound or composition recited herein. IDO- and/or TDO-mediated immunosuppression has been associated with, for example, cancers, tumor growth, metastasis, viral infection, viral replication, etc.

Also disclosed herein are methods of potential treatment of diseases associated with activity or expression, including abnormal activity and/or overexpression, of IDO and/or TDO in an individual (e.g., patient) by administering to the individual in need of such treatment an effective amount or dose of a compound disclosed herein or a pharmaceutical composition thereof. Exemplary diseases include any disease, disorder or condition that may be directly or indirectly linked to expression or activity of the IDO and/or TDO enzyme, such as over expression or abnormal activity. An IDO- and/or TDO-associated disease can also include any disease, disorder or condition that may be prevented, ameliorated, or cured by modulating enzyme activity. Examples of IDO- and/or TDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO and/or TDO enzyme.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO and/or TDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit IDO and/or TDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with IDO and/or TDO enzyme activity by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound of formula (I), (Ia), (Ib), (Ic) or (Id).

One embodiment of the present invention provides for a method of potentially treating a disease or disorder associated with IDO and/or TDO enzyme activity comprising administration of an effective amount of a compound of formula (I), (Ia), (Ib), (Ic) or (Id) to a subject in need of treatment thereof. In one embodiment, the disease or disorder associated with an IDO and/or TDO enzyme is a cell proliferation disorder.

In one embodiment, disclosed herein is the use of a compound of formula (I), (Ia), (Ib), (Ic) or (Id) in a therapy. The compound may be useful in a method of inhibiting IDO and/or TDO enzyme activity in a subject, such as a mammal in need of such inhibition, comprising administering an effective amount of the compound to the subject.

In one embodiment, disclosed herein is a pharmaceutical composition comprising a compound of formula (I), (Ia), (Ib), (Ic) or (Id), or a pharmaceutically acceptable salt thereof, for use in potential treatment of a disorder or disease related to IDO and/or TDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of formula (I), (Ia), (Ib), (Ic) or (Id), or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound of formula (I), (Ia), (Ib), (Ic) or (Id), or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound of formula (I), (Ia), (Ib), (Ic) or (Id). When prepared in unit dosage form, the composition of the invention typically contains from about 0.1 mg to 2 grams, or more specifically, 0.1 mg to 500 mg, or even more specifically, 0.2 mg to 100 mg, of a compound of formula (I), (Ia), (Ib), (Ic) or (Id), or a pharmaceutically acceptable salt thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound of formula (I), (Ia), (Ib), (Ic) or (Id) and one or more other active agent(s) together in the same pharmaceutical composition, or a compound of formula (I), (Ia), (Ib), (Ic) or (Id) and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound of formula (I), (Ia), (Ib), (Ic) or (Id) and at least one other therapeutic agent as a combined preparation for simultaneous, separate or sequential use in therapy. In one embodiment, the therapy is the treatment of a disease or disorder associated with IDO and/or TDO enzyme activity.

In one embodiment, the invention provides a kit comprising two or more separate pharmaceutical compositions, at least one of which contains a compound of formula (I), (Ia), (Ib), (Ic) or (Id). In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound of formula (I), (Ia), (Ib), (Ic) or (Id) for treating a disease or disorder associated with IDO and/or TDO enzyme activity, wherein the medicament is prepared for administration with another active agent. The invention also provides the use of another active agent for treating a disease or disorder associated with an IDO and/or TDO enzyme, wherein the medicament is administered with a compound of formula (I), (Ia), (Ib), (Ic) or (Id).

The invention also provides the use of a compound of formula (I), (Ia), (Ib), (Ic) or (Id) for treating a disease or disorder associated with IDO and/or TDO enzyme activity, wherein the patient has previously (e.g. within 24 hours) been treated with another active agent. The invention also provides the use of another therapeutic agent for treating a disease or disorder associated with IDO and/or TDO enzyme activity, wherein the patient has previously (e.g. within 24 hours) been treated with a compound of formula (I), (Ia), (Ib), (Ic) or (Id). The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1 H-indol-6-yl)-2-[(4-pyridinyimethyj)amino]-3-pyfidinecarboxamide, and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chloro-deoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE).

The invention will now be described in more detail, by way of example only, with reference to the following specific embodiments.

EXPERIMENTAL

The following examples are intended to be illustrative only and not limiting in any way. Abbreviations used are those conventional in the art or the following.

ACN acetonitrile
° C. degree Celsius
DCM dichloromethane
DIPEA di-isopropylethylamine
DMF N,N-dimethylformamide
DMSO dimethylsulfoxide
EtOAc ethyl acetate
EtOH ethanol
g gram(s)
h hour(s)
HPLC high pressure liquid chromatography
kg kilogram
L liter(s)
LC liquid chromatography
LCMS liquid chromatography and mass spectrometry
MeOH methanol
MS mass spectrometry
MTBE methyl tert-butyl ether
min minute(s)
mL milliliter(s)
m/z mass to charge ratio
nm nanometer
nM nanomolar
N normal
NMP N-methyl-2-pyrrolidone
NMR nuclear magnetic resonance
RT or rt room temperature
sat. saturated
TFA trifluoroacetic acid
TLC thin layer chromatography In order to demonstrate an exemplary method for synthesising the compounds of the present invention the following syntheses were carried out:

Preparation of 8-(1-(methylsulfonyl)piperidin-4-yl)-6-(trifluoromethyl)imidazo[1,5-a]pyridine (Compound 1005)

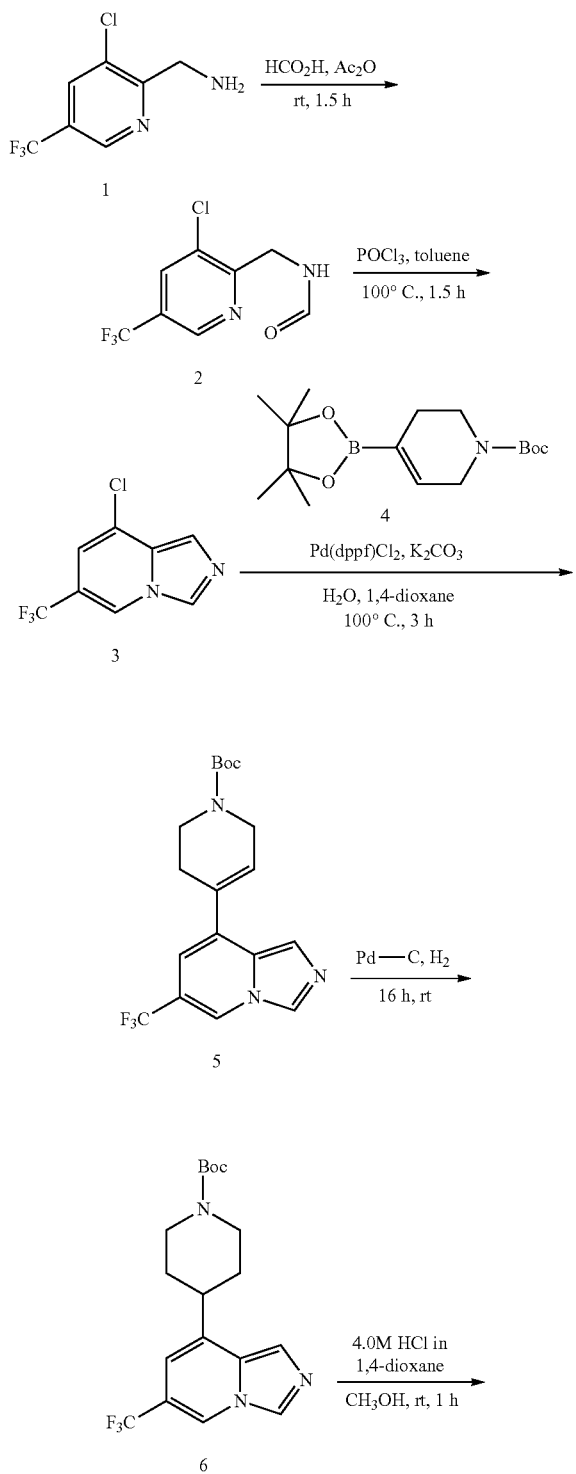

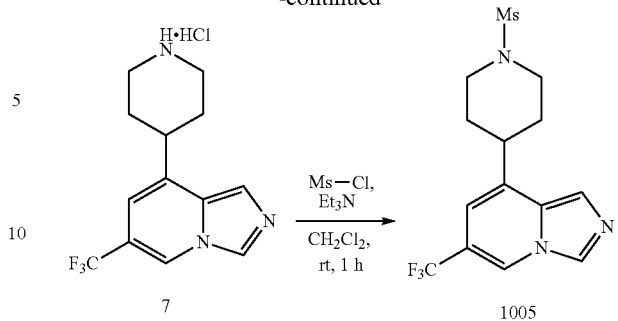

Reagents were purchased from commercial sources and were used as received. ¹H NMR spectra were obtained on a Bruker AVANCE 300 spectrometer at 300 MHz and a Bruker AVANCE 400 spectrometer at 400 MHz with tetramethylsilane used as an internal reference. Thin-layer chromatography (TLC) was performed using Whatman No. 4500-101 (Diamond No. MK6F silica-gel 60 Å) plates. Visualization of TLC plates was performed using UV light (254 nm). The mass spectra were obtained on a Finnigan LCQ-DUO spectrometer using electrospray ionization. HPLC analyses were performed on an Agilent 1100 Series instrument. Impurities are expressed as % AUC by HPLC and are non-validated.

Preparation of 2 —A stirred solution of 1(1.5 g, 7.1 mmol) in HCO$_2$H (37 mL) was treated with Ac$_2$O (7.5 mL) at room temperature. After being stirred at room temperature for 1.5 h, the reaction mixture was concentrated under reduced pressure and then co-evaporated with toluene (2×50 mL) to afford 2 (1.3 g, 76%) as a solid; MS (MM) m/z 239.1 [M+H]⁺.

Preparation of 3—A stirred solution of 2 (1.3 g, 5.4 mmol) in toluene (10 mL) was treated with POCl$_3$ (0.6 mL) mL) at room temperature and then heated to 100° C. for 1.5 h. The reaction mixture was cooled, diluted with EtOAc (50 mL) and poured into aqueous NaOH solution (1 N, 50 mL). The layers were separated and the aqueous layer was extracted with EtOAc (3×50 mL). Combined organic layers were washed with water (100 mL) and brine (100 mL). The organic layer was dried over anhydrous Na$_2$SO$_4$ and concentrated in vacuo to afford 3 (1.1 g, 91%) as a solid; MS (MM) m/z 221.1 [M+H]⁺.

Preparation of 5—To a stirred solution of 3 (400 mg, 1.81 mmol) in a mixture of 1,4dioxane (40 mL) and H$_2$O (40 mL) was charged with 4 (618 mg, 2.0 mmol), powdered K$_2$CO$_3$ (596 mg, 3.6 mmol) and the mixture was purged with argon for 20 min. Pd(dppf)Cl$_2$ (74 mg, 0.09 mmol) was added into this mixture and refluxed for 3 h. The mixture was cooled to room temperature and concentrated to ~30 mL under reduced pressure. The resultant dark brown slurry was diluted with EtOAc (100 mL) and washed with brine (2×75 mL). The organic phase was separated, dried over Na$_2$SO$_4$, filtered and concentrated in vacuo to give a dark brown solid residue. This residue was further purified by Combiflash column chromatography using 12 g Redisep® column (hexanes/EtOAc, 1:1) to afford 5 (360 mg, 54%) as a solid; MS (MM) m/z 368.1 [M+14]⁺.

Preparation of 6—To a stirred solution of 5 (300 mg, 0.8 mmol) in ethanol (10 mL) was charged with Pd—C (30 mg, 10% wt.) under argon atmosphere at room temperature. Hydrogen atmosphere was introduced using a balloon and the reaction mixture was stirred for 16 h. The reaction mixture was filtered through Celite® bed, washed with CH$_3$OH (50 mL) and concentrated under reduced pressure to afford 6 (250 mg, 83%) as a solid; MS (MM) m/z 370.1 [M+H]$^+$.

Preparation of 7—A stirred solution of 6 (250 mg, 0.67 mmol) in CH$_3$OH (10 mL) was treated with 4M HCl in 1,4-dioxan (5 mL) over 10 min at 0° C. The reaction mixture was stirred at room temperature for 3 h and then concentrated under reduced pressure to afford 7 (200 mg, 96%) as HCl salt; MS (MM) m/z 270.1 [M+H]$^+$.

Preparation of Compound 1005—A solution of 7 (200 mg, 0.74 mmol) in CH$_2$Cl$_2$ (5 mL) was treated with Et$_3$N (0.14 mL, 1.1 mmol) followed by MsCl (0.3 mL, 0.7 mmol) over 10 min at 0° C. After being stirred at room temperature for 2 h, the reaction mixture was concentrated under reduced pressure to give a dark brown solid residue. This residue was further purified by Combiflash column chromatography using 12 g Redisep® column (CH$_2$Cl$_2$/CH$_3$OH, 95:5) to afford 1005 (17 mg, 7%) as a solid; MS (MM) m/z 348.1 [M+H]$^+$; HPLC: 94.4%, Eclipse XDB-C-18 column, 270 nm; $^1$HNMR (400 MHz, DMSO-d$_6$): δ 8.92 (s, 1H), 8.53 (s, 1H), 7.65 (s, 1H), 6.79 (s, 1H), 3.71 (d, J=11.6 Hz, 2H), 3.06-3.00 (m, 1H), 2.95-2.89 (m, 2H), 2.92 (s, 3H), 2.00 (d, J=12.8 Hz, 2H), 1.86-1.77 (m, 2H).

Preparation of 8-(3,3-dimethyl-4-(methylsulfonyl) piperazin-1-yl)-6-(trifluoromethyl)imidazo[1,5-a] pyridine (Compound 1014)

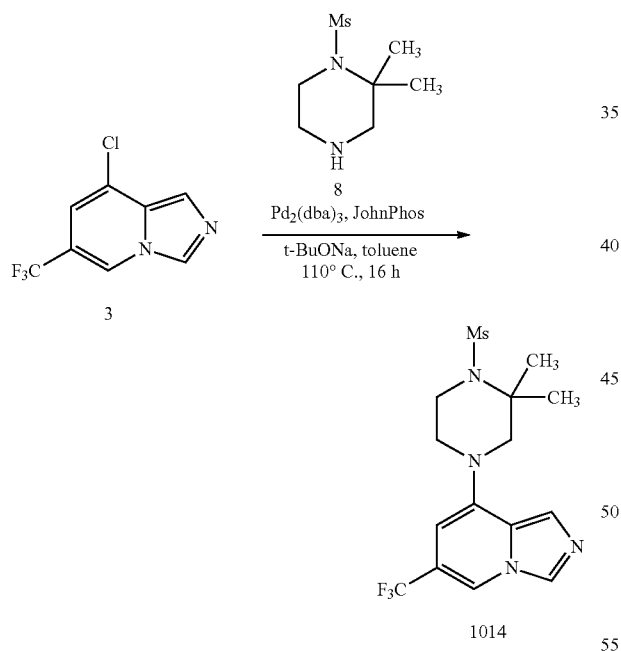

To a stirred solution of 3 (300 mg, 1.36 mmol) in toluene (10 mL) was charged with 8 (261 mg, 1.36 mmol), powdered t-BuONa (260 mg, 2.72 mmol) and the mixture was purged with argon for 20 min. Pd$_2$(dba)$_3$ (248 mg, 0.2 mmol) and JohnPhos (12 mg, 0.04 mmol) were added to the mixture and refluxed at 110° C. for 16 h. The mixture was cooled to room temperature and concentrated under reduced pressure. The resultant dark brown slurry was diluted with ethyl acetate (100 mL) and washed with brine (2×75 mL). The organic phase was separated, dried over Na$_2$SO$_4$, filtered and concentrated in vacuo to give a dark brown residue. This residue was further purified by Combiflash column chromatography using 12 g Redisep® column (hexanes/EtOAc, 1:4) to afford compound 1014 (27 mg, 5%) as a solid; MS (MM) m/z 377.1 [M+H]$^+$ HPLC: 97.7%, Eclipse XDB C-18, 260 nm.

$^1$H NMR (400 MHz, DMSO-d$_6$): δ 8.62 (s, 1H), 8.50 (s, 1H), 7.56 (s, 1H), 6.09 (s, 1H), 3.59 3.56 (m, 2H), 3.38-3.36 (m, 2H), 3.19 (s, 2H), 3.04 (s, 3H), 1.52 (s, 6H).

Synthesis of 5-(4-(methylsulfonyl)phenyl)-7-(trifluoromethyl)imidazo[1,5-a]pyridine (Compound 1015)

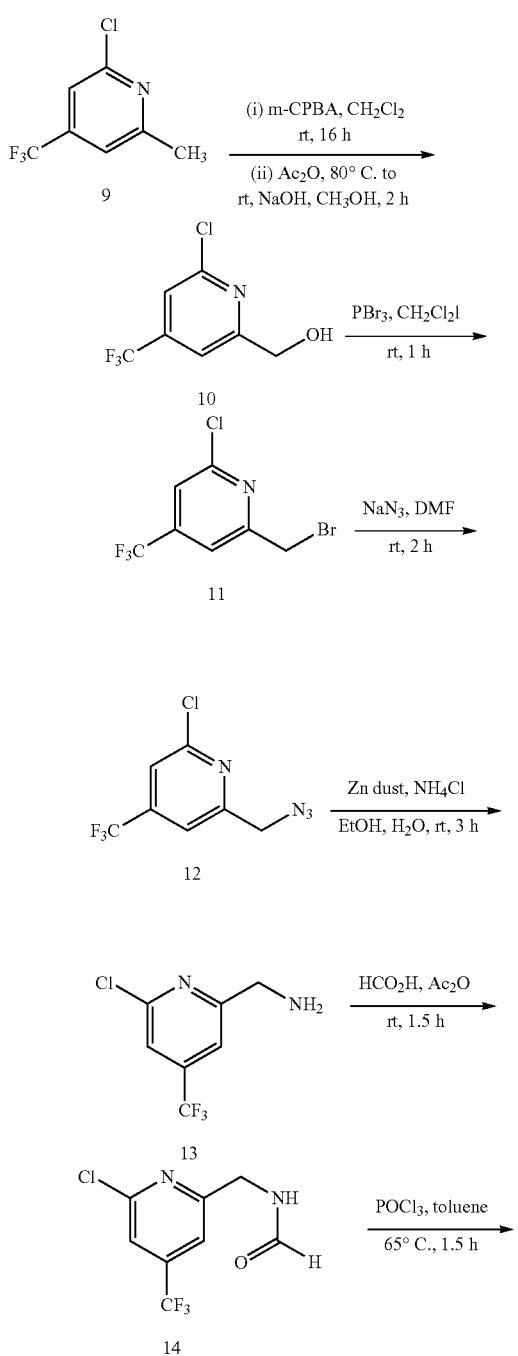

-continued

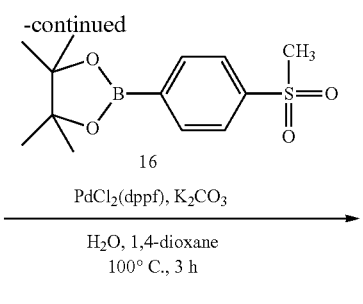

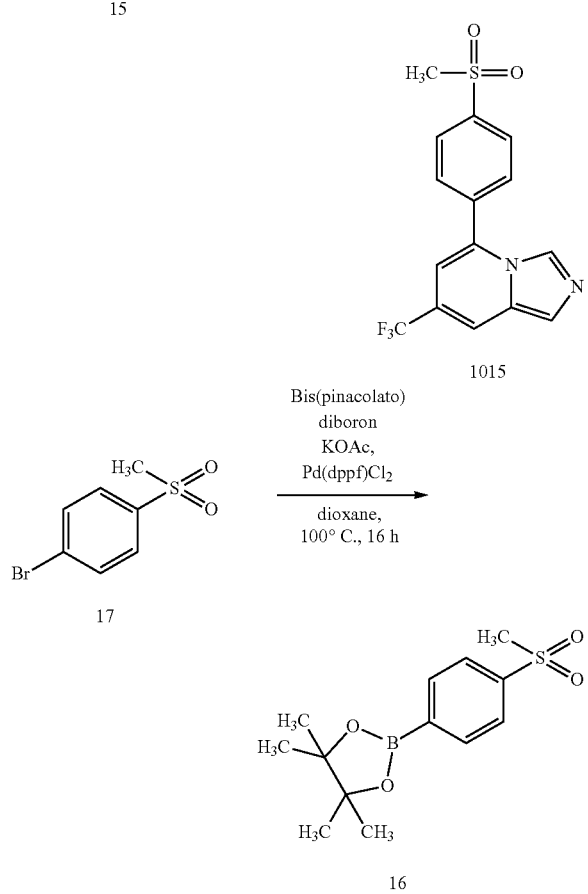

Preparation of 10—To a stirred solution of 9 (5.0 g, 2.5 mmol) in $CH_2Cl_2$ (100 mL) was charged with m-choroperbenzoic acid (25.0 g, 12.5 mmol) at room temperature. After being stirred at room temperature for 16 h, the reaction mixture was diluted with $CH_2Cl_2$ (50 mL) and poured into saturated $NaHCO_3$ solution (250 mL). The layers were separated and the aqueous layer was extracted with $CH_2Cl_2$ (3×150 mL). The combined organic layer was washed with water (100 mL) and brine (100 mL), dried over anhydrous $Na_2SO_4$ and concentrated under the reduced pressure at 25° C. The resultant crude residue was charged with $Ac_2O$ (50 mL) and heated to reflux for 3 h. The reaction mixture was concentrated under reduced pressure. The resultant residue was dissolved in $CH_3OH$ (50 mL), treated with 6N NaOH solution (50 mL) at room temperature and stirred for 1 h. The reaction mixture was diluted with EtOAc (50 mL) and layers were separated. The aqueous layer was extracted with EtOAc (3×150 mL) and the combined organic layers were washed with water (100 mL) and brine (100 mL). The organic layer was dried over anhydrous $Na_2SO_4$ and concentrated under reduced pressure to afford 10 (1.30 g, 24%) as a gum; MS (MM) m/z 212.1[M+H]$^+$.

Preparation of 11—To a solution of 10 (1.3 g, 5.8 mmol) in $CH_2Cl_2$ (25 mL) at 0° C. was charged with $PBr_3$ (1.4 g, 6.5 mmol) over 10 min. After being stirred at room temperature for 2 h, the mixture was diluted with $CH_2Cl_2$ (25 mL) and pH of the solution was adjusted to 8 with saturated $NaHCO_3$ solution (100 mL). The layers were separated and the aqueous layer was extracted with $CH_2Cl_2$ (3×50 mL). The combined organic layers were washed with water (100 mL) and brine (100 mL). The organic layer was dried over anhydrous $Na_2SO_4$ and concentrated under reduced pressure to afford 11 (1.25 g, 74%) as a gum; MS (MM) m/z 275.1[M+H]$^+$.

Preparation of 12—To a solution of 11(1.25 g, 4.5 mmol) in DMF (20 mL) was charged with $NaN_3$ (2.9 g, 4.5 mmol) at room temperature and the mixture was stirred at room temperature for 2 h. The reaction mixture was diluted with EtOAc (25 mL) followed by water (100 mL). Layers were separated and the aqueous layer was extracted with EtOAc (3×50 mL). The combined organic layers were washed with water (100 mL) and brine (100 mL). The organic layer was dried over anhydrous $Na_2SO_4$ and concentrated under reduced pressure to afford 12 (1.05 g, 97%) as a gum; MS (MM) m/z 237.1[M+H]$^+$.

Preparation of 13—To a solution of 12 (1.05 g, 4.6 mmol) in ethanol (20 mL) and $H_2O$ (20 mL) was charged with Zn powder (3.00 g, 4.6 mmol) followed by $NH_4Cl$ (2.47 g, 4.6 mmol) at room temperature. After being stirred at room temperature for 2 h, the reaction mixture was filtered through Celite® bed and washed with $CH_2Cl_2$ (100 mL). The layers were separated and the aqueous layer was extracted with $CH_2Cl_2$ (3×50 mL). The combined organic layers were washed with water (100 mL), brine (100 mL), dried over anhydrous $Na_2SO_4$ and concentrated under reduced pressure to afford 13 (900 mg, 96%) as a solid; MS (MM) m/z 211.1 [M+H]$^+$.

Preparation of 14—A stirred solution of 13 (900 mg, 4.2 mmol) in $HCO_2H$ (25 mL) was treated with $Ac_2O$ (5 mL) at room temperature. After being stirred at room temperature for 1.5 h, reaction mixture was concentrated under reduced pressure and then co-evaporated with toluene (2×50 mL) to afford 14 (1.00 g, 98%) as a solid; MS (MM) m/z 239.1 [M+H]$^+$.

Preparation of 15—A stirred solution of 14 (1.00 g, 4.2 mmol) in toluene (10 mL) was treated with $POCl_3$ (0.5 mL) mL) at room temperature and then heated to 100° C. for 1.5 h. The reaction mixture was cooled, diluted with EtOAc (50 mL) and poured into aqueous NaOH solution (1 N, 50 mL). The layers were separated and the aqueous layer was extracted with EtOAc (3×50 mL). Combined organic layers were washed with water (100 mL) and brine (100 mL). The organic layer was dried over anhydrous $Na_2SO_4$ and concentrated in vacuo to afford 15 (650 mg, 70%) as a solid; MS (MM) m/z 221.1[M+H]$^+$.

Preparation of 16—A solution of 17 (1.00 g, 4.25 mmol), bis-(pinacolato)diboron (3.20 g, 12.8 mmol) in 1,4-dioxane (10 mL) was treated with KOAc (535 mg, 5.46 mmol). The solution was degassed with argon for 10 min. $Pd(dppf)Cl_2$ (171 mg, 0.21 mmol) was added into this mixture and allowed to stir at 100° C. for 4 h. The reaction mixture was cooled, poured into water (70 mL) and extracted with EtOAc (3×150 mL). The combined organic layers were washed with water (200 mL) and brine (100 mL). The organic layer was dried over anhydrous $Na_2SO_4$ and concentrated in vacuo to afford crude product. The crude product was purified by Combiflash chromatography using 12 g Redisep® column (hexanes/EtOAc, 1:1). The fractions were concentrated and dried under reduced pressure to afford 16 (850 mg, 77%) as a solid; MS (MM) m/z 327 [M−H]⁻.

Preparation of Compound 1015—To a stirred solution of 15 (120 mg, 0.54 mmol) in a mixture of 1,4dioxane (10 mL) and water (10 mL) was charged with 16 (163 mg, 0.59 mmol), powdered K$_2$CO$_3$ (150 mg, 1.09 mmol) and the mixture was purged with argon for 20 min. PdCl$_2$(dppf) (22 mg, 0.02 mmol) was added into the mixture and refluxed for 3 h. The mixture was cooled to room temperature and concentrated to 30 mL under reduced pressure. The resultant dark brown slurry was diluted with ethyl acetate (100 mL) and washed with brine (2×75 mL). The organic phase was separated, dried over Na$_2$SO$_4$, filtered and concentrated in reduce pressure to give a dark brown solid residue. This residue was further purified by Combiflash column chromatography using 12 g Redisep® column (hexanes/EtOAc, 1:4) to afford 1015 (56 mg, 31%) as a solid; MS (MM) m/z 341.1[M+H]⁺; HPLC: 98.4%, Eclipse XDB C-18, 230 nm; $^1$H NMR (300 MHz, DMSO-d$_6$): δ 8.47 (s, 1H), 8.26 (s, 1H), 8.15 (d, J=8.7 Hz, 2H), 8.11 (d, J=8.7 Hz, 2H), 7.84 (s, 1H), 6.98 (s, 1H), 3.32 (s, 3H).

Synthesis of 6-chloro-8-(4-(methylsulfonyl)phenyl) imidazo[1,5-a]pyridine (Compound 1010)

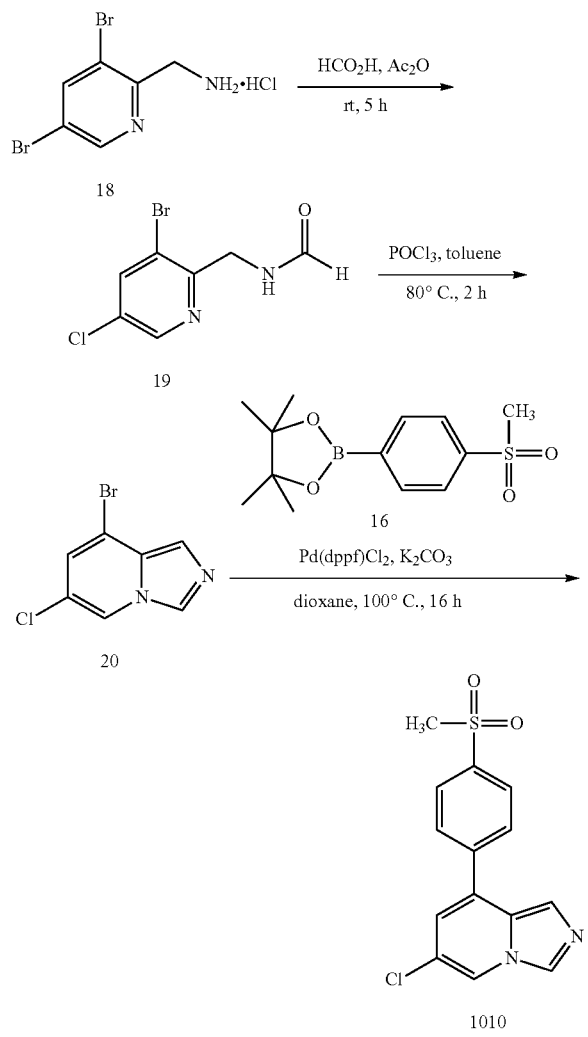

Preparation of 19—A solution of 18 (1.00 g, 3.97 mmol) in HCO$_2$H (25 mL) and Ac$_2$O (5 mL) was stirred at 80° C. for 5 h. The solvent was evaporated in vacuo. Crude compound was co-distilled with toluene (2×50 mL) and dried to afford 19 (1.05 g, crude) as a solid; MS (MM) m/z 248.9 [M+H]⁺.

Preparation of 20—A solution of 19 (1.05 g, 4.21 mmol) in toluene (20 mL) was treated with POCl$_3$ (0.5 mL) and the mixture was stirred at 90° C. for 2 h. Solvent was evaporated in vacuo. The crude compound was basified with aqueous NaOH (2N, 10 mL) solution, and extracted with EtOAc (2×50 mL). The combined organic layers were washed with water (2×50 mL) and brine (50 mL). The organic layer was collected, dried over anhydrous Na$_2$SO$_4$, filtered and evaporated in vacuo to afford 20 (620 mg, crude) as a solid; MS (MM) m/z 230.9 [M+14]⁺.

Preparation of Compound 1010—A solution of 20 (200 mg, 0.864 mmol) and 16 (292 mg, 1.03 mmol) in a mixture of 1,4dioxane (8 mL) and H$_2$O (2 mL) was treated with K$_2$CO$_3$ (238 mg, 1.72 mmol). The solution was degassed with argon for 10 min. Pd(dppf)Cl$_2$ (35 mg, 0.04 mmol) was added into this mixture and stirred at 100° C. for 16 h. The reaction mixture was cooled and concentrated under reduced pressure. The crude product was purified by Combiflash chromatography using 4 g Redisep® column (hexanes/EtOAc, 1:1). The fractions were concentrated and dried under reduced pressure to afford 1010 (15 mg, 6%) as a solid; MS (MM) m/z 307 [M+H]⁺; HPLC: 99.3%, Eclipse XDB C-18, 230 nm; $^1$H NMR (400 MHz, DMSO-d$_6$): δ 8.74 (t, J=1.2 Hz, 1H), 8.49 (s, 1H), 8.16-8.03 (m, 4H), 7.57 (s, 1H), 7.07 (d, J=1.6 Hz, 1H) 3.32 (s, 3H).

Synthesis of Compound 1021

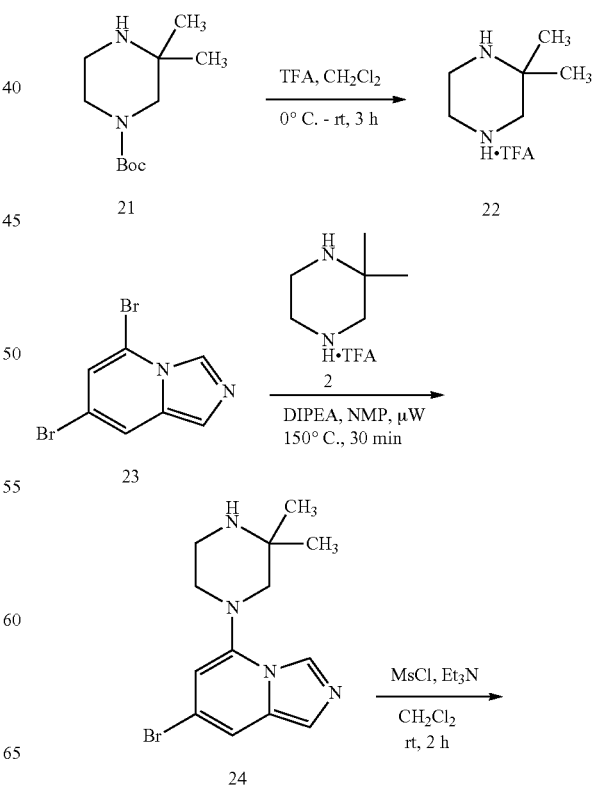

-continued

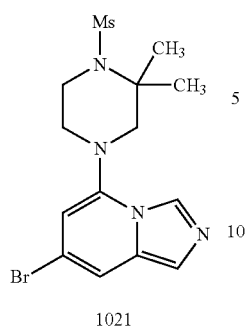

1021

Preparation of 22—A solution of 21 (200 mg, 0.93 mmol) in CH₂Cl₂ (5.0 mL) was charged with TFA (1.0 mL) at 0° C. The reaction mixture was stirred at room temperature for 3 h. The reaction mixture was concentrated in vacuo to afford 22 [100 mg (crude), 94%] as a liquid.

Preparation of 24—A solution 23 (150 mg, 0.54 mmol) in NMP (2.0 mL) was charged with 22 (71.0 mg, 0.65 mmol) and DIPEA (0.13 mg, 1.05 mmol) at room temperature. The reaction mixture was irradiated under microwave for 30 min at 150° C. The reaction mixture was cooled to room temperature, directly loaded into combiflash column chromatography and purified using Redisep® column (12 g, CH₂Cl₂/CH₃OH, 9:1) to afford 24 (50.0 mg, 29%) as a solid.

Preparation of Compound 1021—A solution 24 (70.0 mg, 0.22 mmol) in CH₂Cl₂ (5.0 mL) at 0° C. was charged with Et₃N (60.0 mg, 0.44 mmol) followed by MsCl (20.0 mg, 0.27 mmol). The reaction mixture was stirred at room temperature for 2 h. Water (10 mL) was added to the reaction mixture and extracted with EtOAc (2×20 mL). The organic phase was separated, dried over anhydrous Na₂SO₄, filtered and concentrated to afford a crude product. The crude product was purified by combiflash column chromatography using Redisep® column (4 g, CH₂Cl₂/CH₃OH, 9:1) to afford compound 1021 (23.0 mg, 25%) as a solid. MS (MM) m/z 387.0 [M+H]⁺; HPLC: 92.3%, Eclipse XDB C18, 220 nm. ¹H NMR (300 MHz, DMSO-d₆): δ 8.32 (s, 1H), 7.67 (s, 1H), 7.42 (s, 1H), 6.30 (s, 1H), 3.62 (d, J=4.8 Hz, 2H), 3.15-3.14 (m, 2H), 3.05 (s, 3H), 3.00 (s, 2H), 1.53 (s, 6H).

Synthesis of Compound 1022

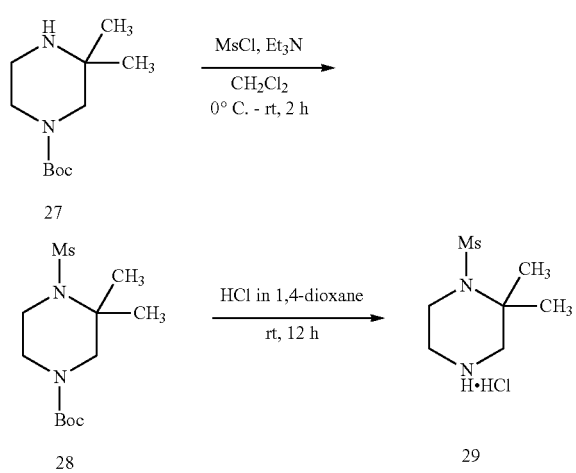

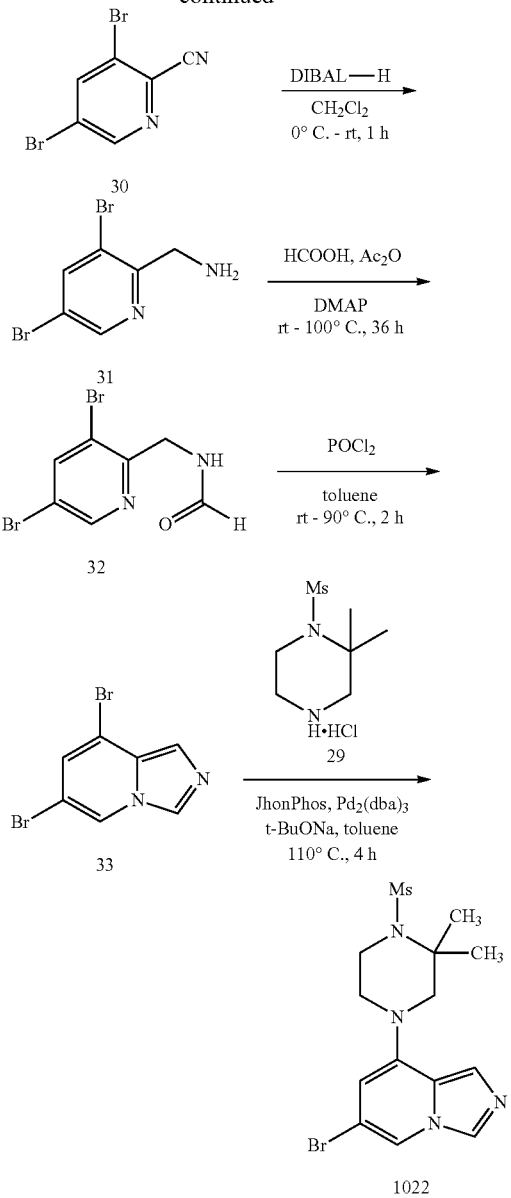

1022

Preparation of 28—To a solution of 27 (1.00 g, 4.6 mmol) in CH₂Cl₂ (10 mL) at 0° C. was charged with Et₃N (2.30 g, 23 mmol) followed by MsCl (0.59 mg, 7.0 mmol). The reaction mixture was stirred at room temperature for 2 h. Water (50 mL) was added to the reaction mixture and extracted with CH₂Cl₂ (2×50 mL). The organic phase was separated, dried over anhydrous Na₂SO₄, filtered and concentrated to afford 28 [1.20 g (crude)] as a solid, which was used for the next step without further purification.

Preparation of 29—A mixture of 28 (1.20 g, 4.6 mmol) and HCl in 1,4-dioxane (4 M, 30 mL) was stirred at room temperature for 12 h. The solvent was evaporated under reduced pressure to afford 29 [950 mg (crude)] as a solid which was used for the next step without further purification.

Preparation of 31—To a solution of 30 (5.00 g, 19.3 mmol) in CH₂Cl₂ (10 mL) at 0° C. was charged with DIBAL-H (1 M solution in CH₂Cl₂, 38.6 mL) dropwise. The reaction mixture was stirred at room temperature for 1 h. The reaction mixture was quenched with saturated NH₄Cl solution (100 mL), basified with aqueous NaOH solution (6 N, 100 mL) and was extracted with EtOAc (2×100 mL). The organic phase was separated, dried over anhydrous $Na_2SO_4$, filtered and concentrated to afford 31 [5.00 g (crude)] as a solid, which was used for the next step without any purification. MS (MM) m/z 267.0 [M+H]$^+$.

Preparation of 32—To a solution of 31 (5.00 g, 18.8 mmol) in $HCO_2H$ (37 mL) was charged with $Ac_2O$ (7.5 mL) at room temperature. The reaction mixture was stirred at 100° C. for 36 h. The reaction mixture was concentrated under reduced pressure and further dried by co-evaporating with toluene (2×50 mL) to afford 32 (4.00 g) as a solid, which was used for the next step without further purification. MS (MM) m/z 294.1 [M+H]$^+$.

Preparation of 33—To a stirred solution of 32 (4.00 g, 5.4 mmol) in toluene (40 mL) was charged with $POCl_3$ (2.0 mL) at room temperature. The reaction mixture was heated at 100° C. for 2 h. The reaction mixture was cooled to room temperature, diluted with EtOAc (50 mL) and poured into aqueous NaOH solution (1 N, 50 mL). The layers were separated and the aqueous layer was extracted with EtOAc (3×50 mL). The combined organic layers were washed with water (100 mL) and brine (100 mL). The organic layer was dried over anhydrous $Na_2SO_4$ and concentrated in vacuo. The resultant residue was purified by combiflash column chromatography using Redisep® column (24 g, hexanes/EtOAc, 1:1) to afford 33 (1.50 g, 40%) as a solid.

Preparation of Compound 1022—To a stirred solution of 33 (200 mg, 1.36 mmol) in toluene (10 mL) was charged with 29 (261 mg, 1.36 mmol), t-BuONa (260 mg, 2.72 mmol) at room temperature. The reaction mixture was purged with argon for 20 min. $Pd_2(dba)_3$ (248 mg, 0.2 mmol) and JohnPhos (12.0 mg, 0.04 mmol) were added to the reaction mixture and refluxed to 110° C. for 4 h. The mixture was cooled to room temperature and concentrated under reduced pressure. The resultant dark brown slurry was diluted with EtOAc (100 mL) and washed with brine (2×75 mL). The organic phase was separated, dried over anhydrous $Na_2SO_4$, filtered and concentrated in vacuo to afford a residue. This residue was further purified by combiflash column chromatography using Redisep® column (4 g, EtOAc) to afford 1022 (5.00 mg, 2%) as a solid. MS (MM) m/z 387.1 [M+H]$^+$ HPLC: 92.1%, Eclipse XDB C18, 220 nm. $^1$H NMR (400 MHz, DMSO-$d_6$): δ 8.31 (s, 2H), 7.47 (s, 1H), 6.10 (s, 1H), 3.57-3.55 (m, 2H), 3.45-3.32 (m, 2H) 3.15 (s, 2H), 3.03 (s, 3H), 1.51 (s, 2H).

Synthesis of Compound 1023

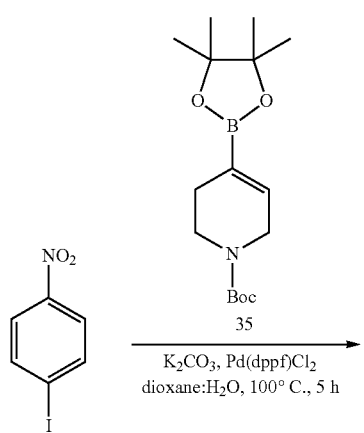

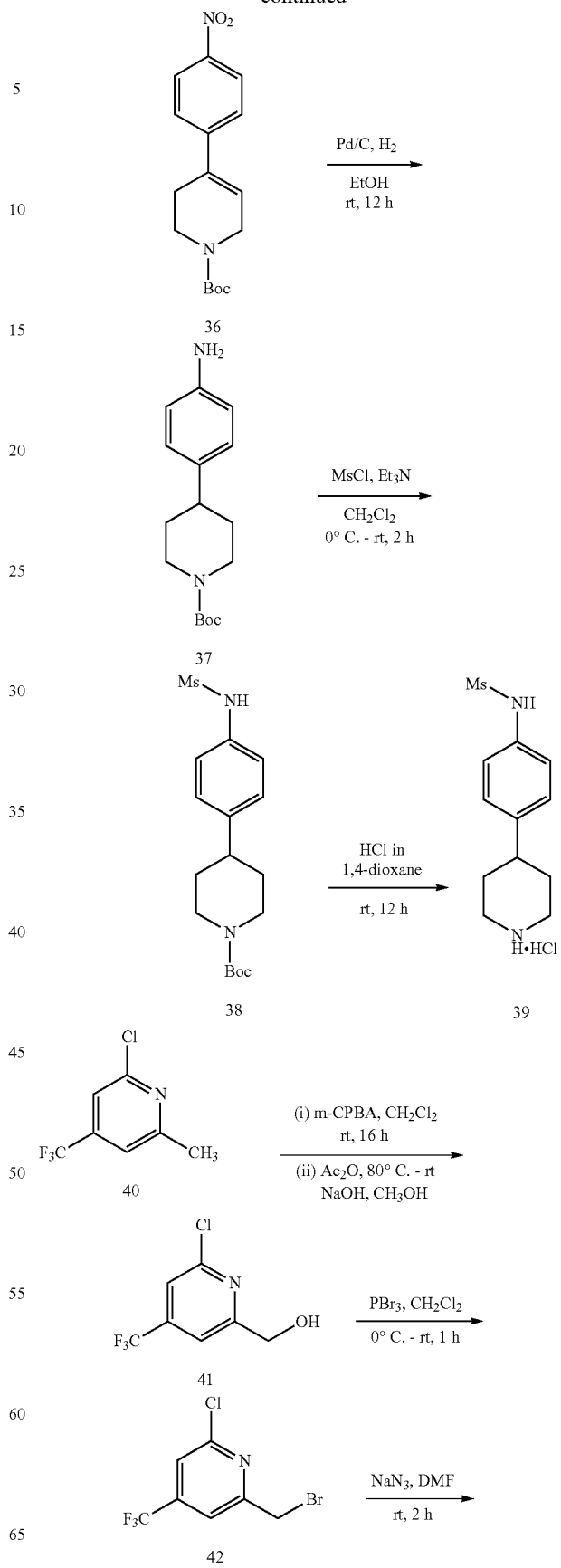

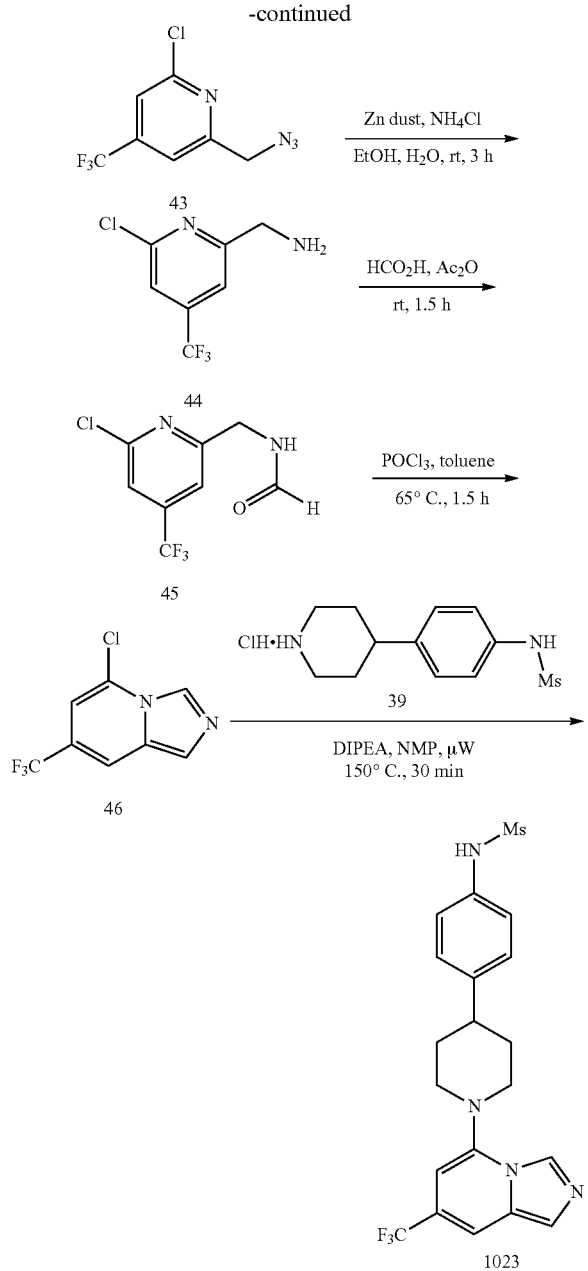

Preparation of 36—To a stirred solution of 34 (10.0 g, 40.1 mmol) in a mixture of 1,4-dioxane (50 mL) and H$_2$O (50 mL) was charged with 35 (13.8 g, 44.17 mmol) and K$_2$CO$_3$ (11.08 g, 80.32 mmol) at room temperature. The reaction mixture was purged with argon for 20 min. Pd(dppf)Cl$_2$ (1.63 g, 2.0 mmol) was added to the reaction mixture and refluxed for 5 h. The reaction mixture was cooled to room temperature and concentrated to 30 mL under reduced pressure. The resultant slurry was diluted with EtOAc (100 mL) and washed with brine (3×100 mL). The organic phase was separated, dried over anhydrous Na$_2$SO$_4$, filtered and was concentrated in vacuo to afford a solid residue. The residue was further purified by combiflash column chromatography using Redisep® column (80 g, hexanes/EtOAc, 1:1) to afford 36 (11.0 g, 91%) as a solid. MS (MM) m/z 305.0 [M+H]$^+$.

Preparation of 37—To a stirred solution of 36 (8.00 g, 26.2 mmol) in EtOH (10 mL) was charged with Pd/C (1.60 g, 10% wt) under argon atmosphere at room temperature. Hydrogen atmosphere was introduced using a balloon and the reaction mixture was stirred for 12 h at the same temperature. The reaction mixture was filtered through Celite® bed, washed with CH$_3$OH (50 mL) and was concentrated under reduced pressure to afford 37 (1.50 g, 20%) as a solid. MS (MM) m/z 277.1 [M+H]$^+$.

Preparation of 38—To a solution of 37 (500 mg, 1.8 mmol) in CH$_2$Cl$_2$ (15 mL) at 0° C. was charged with Et$_3$N (540 mg, 5.4 mmol) followed by MsCl (310 mg, 2.7 mmol). The reaction mixture was stirred at room temperature for 2 h. The reaction mixture was diluted with water (10 mL) and extracted with EtOAc (2×20 mL). The organic phase was separated, dried over anhydrous Na$_2$SO$_4$ and concentrated. The crude product was purified by combiflash column chromatography using Redisep® column (12 g, hexanes/EtOAc, 1:1). The fractions were concentrated and dried under reduced pressure to afford 38 (500 mg, 78%) as a solid. MS (MM) m/z 355.1 [M+H]$^+$.

Preparation of 39—A mixture of 38 (500 mg, 4.6 mmol) and HCl in 1,4-dioxane (4 M, 20 mL) was stirred at room temperature for 12 h. The solvent was evaporated under reduced pressure to afford 39 (500 mg) as a solid which was used for next step without further purification. MS (MM) m/z 255.0 [M+H]$^+$.

Preparation of 41—To a stirred solution of 40 (5.00 g, 2.5 mmol) in CH$_2$Cl$_2$ (100 mL) was charged with m-choroperbenzoic acid (25.0 g, 12.5 mmol) at room temperature. The reaction mixture was stirred at room temperature for 16 h. The reaction mixture was diluted with CH$_2$Cl$_2$ (50 mL) and poured into saturated NaHCO$_3$ solution (250 mL). The layers were separated and the aqueous layer was extracted with CH$_2$Cl$_2$ (3×150 mL). The combined organic layer was washed with water (100 mL) and brine (100 mL). The organic layer was dried over anhydrous Na$_2$SO$_4$ and concentrated under reduced pressure at 25° C. The resultant crude residue was added to Ac$_2$O (50 mL) and heated to reflux for 3 h. The reaction mixture was cooled to room temperature, concentrated to afford a residue. The residue was dissolved in CH$_3$OH (50 mL), treated with aqueous NaOH solution (6 N, 50 mL) and stirred for 1 h at same temperature. The reaction mixture was diluted with EtOAc (50 mL) and layers were separated. The aqueous layer was extracted with EtOAc (3×150 mL). The combined organic layers were washed with water (100 mL) and brine (100 mL). The organic layer was dried over anhydrous Na$_2$SO$_4$ and concentrated under reduced pressure to afford 41 (1.30 g, 24%) as a gum. MS (MM) m/z 212.1 [M+H]$^+$.

Preparation of 42—To a solution of 41 (1.30 g, 5.8 mmol) in CH$_2$Cl$_2$ (25 mL) at 0° C. was charged with PBr$_3$ (1.40 g, 6.5 mmol) over 10 min. The reaction mixture was stirred at room temperature for 1 h. The reaction mixture was diluted with CH$_2$Cl$_2$ (25 mL) and pH of the solution was adjusted to 8 with saturated NaHCO$_3$ solution (100 mL). The layers were separated and the aqueous layer was extracted with CH$_2$Cl$_2$ (3×50 mL). The combined organic layers were washed with water (100 mL) and brine (100 mL). The organic layer was dried over anhydrous Na$_2$SO$_4$ and concentrated under reduced pressure to afford 42 (1.25 g, 74%) as a gum. MS (MM) m/z 275.1 [M+H]$^+$.

Preparation of 43—To a solution of 42 (1.25 g, 4.5 mmol) in DMF (20 mL) was charged with NaN$_3$ (2.90 g, 4.5 mmol) at room temperature. The reaction mixture was stirred at room temperature for 2 h. The reaction mixture was diluted with EtOAc (25 mL) followed by water (100 mL). The layers were separated and the aqueous layer was extracted with EtOAc (3×50 mL). The combined organic layers were washed with water (100 mL) and brine (100 mL). The organic layer was dried over anhydrous Na$_2$SO$_4$ and concentrated under reduced pressure to afford 43 (1.05 g, 97%) as a gum. MS (MM) m/z 237.1 [M+H]$^+$.

Preparation of 44—To a solution of 43 (1.05 g, 4.6 mmol) in EtOH (20 mL) and H$_2$O (20 mL) was charged with Zn powder (3.00 g, 4.6 mmol) followed by NH$_4$Cl (2.47 g, 4.6 mmol) at room temperature. The reaction mixture was stirred at room temperature for 3 h. The reaction mixture was filtered through Celite® bed and washed with CH$_2$Cl$_2$ (100 mL). The layers were separated and the aqueous layer was extracted with CH$_2$Cl$_2$ (3×50 mL). The combined organic layers were washed with water (100 mL) and brine (100 mL). The organic layers were dried over anhydrous Na$_2$SO$_4$ and concentrated under reduced pressure to afford 44 (900 mg, 96%) as a solid. MS (MM) m/z 211.1 [M+H]$^+$.

Preparation of 45—To a stirred solution of 44 (900 mg, 4.2 mmol) in HCO$_2$H (25 mL) was charged with Ac$_2$O (5.0 mL) at room temperature. The reaction mixture was stirred at room temperature for 1.5 h. The reaction mixture was concentrated under reduced pressure and then co-evaporated with toluene (2×50 mL) to afford 45 (1.00 g, 98%) as a solid. MS (MM) m/z 239.1 [M+H]$^+$.

Preparation of 46—To a stirred solution of 45 (1.00 g, 4.2 mmol) in toluene (10 mL) was charged with POCl$_3$ (0.5 mL) at room temperature. The reaction mixture was heated at 65° C. for 1.5 h. The reaction mixture was cooled, diluted with EtOAc (50 mL) and poured into aqueous NaOH solution (1 N, 50 mL). The layers were separated and the aqueous layer was extracted with EtOAc (3×50 mL). The combined organic layers were washed with water (100 mL) and brine (100 mL). The organic layer was dried over anhydrous Na$_2$SO$_4$ and concentrated in vacuo to afford 46 (650 mg, 70%) as a brown solid. MS (MM) m/z 221.1 [M+H]$^+$.

Preparation of Compound 1023—A solution of 46 (100 mg, 0.45 mmol), 39 (126 mg, 0.49 mmol), DIPEA (250 mg, 0.9 mmol) in NMP (1.0 mL) was irradiated under microwave at 150° C. for 30 min. The reaction mixture was cooled to room temperature, diluted with EtOAc (30 mL) and washed with brine (3×50 mL). The organic layer was separated, dried over anhydrous Na$_2$SO$_4$ concentrated and dried under reduced pressure to afford crude compound. The crude compound was stirred with MTBE (20 mL) and filtered to afford compound 1023 (30.0 mg, 15%) as a solid. MS (MM) m/z 439.1 [M+H]$^+$. HPLC: 95.8%, Eclipse XDB C18, 220 nm.

$^1$H NMR (300 MHz, DMSO-d$_6$): δ 9.65 (s, 1H), 8.44 (s, 1H), 7.87 (s, 1H), 7.72 (s, 1H), 7.32 (d, J=8.7 Hz, 2H), 7.18 (d, J=8.4 Hz, 2H), 6.30 (s, 1H), 3.57 (d, J=12.0 Hz, 2H), 2.97 (s, 3H), 2.93-2.90 (m, 2H), 2.78-2.73 (m, 1H), 1.99-1.94 (m, 4H).

Synthesis of Compound 1024

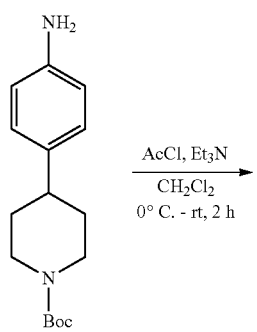

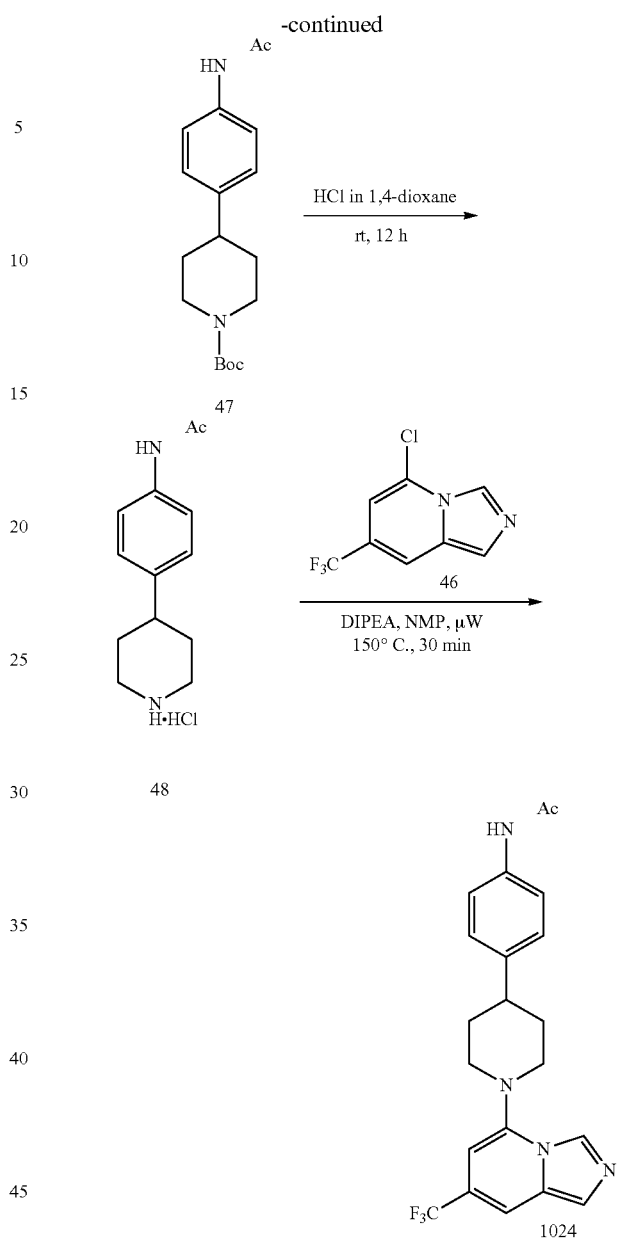

Preparation of 47—To a solution of 37 (2.50 g, 9.0 mmol) in CH$_2$Cl$_2$ (15 mL) at 0° C. was charged with Et$_3$N (540 mg, 5.4 mmol) followed by AcCl (1.00 g, 13.5 mmol). The reaction mixture was stirred at room temperature for 2 h. The reaction mixture was diluted with water (10 mL) and extracted with EtOAc (2×20 mL). The organic phase was separated, dried over anhydrous Na$_2$SO$_4$ and concentrated under reduced pressure to afford crude product. The crude product was purified by combiflash column chromatography using Redisep® column (12 g, hexanes/EtOAc, 1:1) to afford 47 (2.00 g, 71%) as a solid.

Preparation of 48—A mixture of 47 (2.00 g, 6.2 mmol) and HCl in 1,4-dioxane (4 M, 30 mL) was stirred at room temperature for 12 h. The solvent was removed under reduced pressure to afford 48 [1.00 g (crude), 76%] as a solid, which was used for next step without further purification. MS (MM) m/z 219.1 [M+H]$^+$.

Preparation of Compound 1024—A solution of 46 (100 mg, 0.45 mmol), 48 (126 mg, 0.49 mmol) and DIPEA (250 mg, 9 mmol) in NMP (1.0 mL) was irradiated under microwave at 150° C. for 30 min. The reaction mixture was cooled to room temperature, diluted EtOAc (30 mL) and washed with brine (3×50 mL). The organic layer was collected, dried over anhydrous Na$_2$SO$_4$, concentrated and dried under reduced pressure. The resultant crude product was stirred with MTBE (20 mL) and filtered to afford compound 1024 (30.0 mg, 16%) as a solid. MS (MM) m/z 403.1 [M+H]$^+$. HPLC: >99%, Eclipse XDB C18, 220 nm. $^1$H NMR (400 MHz, DMSO-d$_6$): δ 9.89 (s, 1H), 8.44 (s, 1H), 7.86 (s, 1H), 7.72 (s, 1H), 7.53 (d, J=8.4 Hz, 2H), 7.26 (d, J=8.4 Hz, 2H), 6.29 (s, 1H), 3.55 (d, J=11.6 Hz, 2H), 2.92 (t, J=11.6 Hz, 2H), 2.73-2.71 (m, 1H), 2.03 (s, 3H), 1.99-1.92 (m, 4H).

Synthesis of Compound 1025

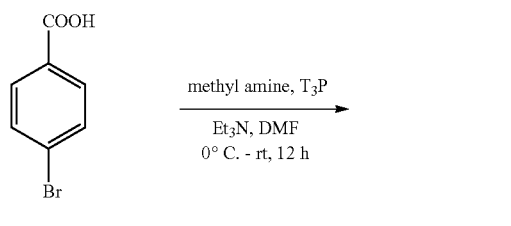

Preparation of 50—To a stirred solution of 49 (5.00 g, 24.8 mmol) in DMF (50 mL) at 0° C. was charged with methyl amine (1.64 g, 49.6 mmol), T$_3$P (15.7 g, 49.9 mmol) and Et$_3$N (7.51 g, 74.4 mmol). The reaction mixture was stirred for 12 h at room temperature. The reaction mixture was treated with water (50 mL) and extracted with EtOAc (3×50 mL). The organic phase was separated, dried over anhydrous Na$_2$SO$_4$ and evaporated to afford 50 [3.50 g (crude), 67%] as a solid, which was used for next step without further purification. MS (MM) m/z 215.1 [M+H]$^+$.

Preparation of 51—To a stirred solution of 50 (2.90 g, 13.6 mmol) in a mixture of 1,4-dioxane (20 mL) and H$_2$O (20 mL) was charged with 35 (13.8 g, 44.17 mmol) and K$_2$CO$_3$ (3.75 g, 27.2 mmol) at room temperature. The reaction mixture was purged with argon for 20 min. Pd(dppf)Cl$_2$ (550 mg, 0.68 mmol) was added to the reaction mixture and refluxed for 5 h. The mixture was cooled to room temperature and concentrated to 30 mL under reduced pressure. The resultant dark brown slurry was diluted with EtOAc (100 mL) and washed with brine (3×100 mL). The organic phase was separated, dried over anhydrous Na$_2$SO$_4$, filtered and concentrated in vacuo to afford a solid residue. The residue was further purified by combiflash column chromatography using Redisep® column (80 g, hexanes/EtOAc, 1:1) to afford 51 (3.70 g, 84%) as a solid. MS (MM) m/z 317.1 [M+H]$^+$.

Preparation of 52—A stirred solution of 51 (3.70 g, 26.2 mmol) in EtOH (10 mL) was charged with Pd/C (600 mg, 10% wt) under argon atmosphere at room temperature. Hydrogen atmosphere was introduced using a balloon and the reaction mixture was stirred for 12 h. Upon completion of starting material, the reaction mixture was filtered through Celite® bed, washed with CH$_3$OH (50 mL) and concentrated under reduced pressure to afford 52 (3.50 g, 94%) as a solid.

Preparation of 53—A mixture of 52 (2.00 g, 6.2 mmol) and HCl in 1,4-dioxane (4 M, 30 mL) was stirred at room temperature for 6 h. The solvent was evaporated under reduced pressure to afford 53 (3.00 g) as a solid. MS (MM) m/z 219.1 [M+H]$^+$.

Preparation of Compound 1025—A solution of 46 (100 mg, 0.45 mmol), 53 (126 mg, 0.49 mmol) and DIPEA (250 mg, 0.9 mmol) in NMP (1.0 mL) was irradiated under microwave at 150° C. for 30 min. The reaction mixture was cooled to room temperature, diluted with EtOAc (30 mL) and washed with brine (3×50 mL). The organic layer was collected, dried over anhydrous Na$_2$SO$_4$ and concentrated under reduced pressure to afford crude product. The crude product was stirred with MTBE (20 mL) and filtered to afford pure 1025 (90.0 mg, 47%) as a solid. MS (MM) m/z 403.1 [M+H]$^+$. HPLC: 98.3%, Eclipse XDB C 18, 220 nm. $^1$H NMR (300 MHz, DMSO-d$_6$): δ 8.46 (s, 1H), 8.40 (d, J=4.5 Hz, 1H), 7.87 (s, 1H), 7.82 (d, J=8.4 Hz, 2H), 7.72 (s, 1H), 7.44 (d, J=8.4 Hz, 2H), 6.32 (s, 1H), 3.57 (d, J=12.0 Hz, 2H), 2.94 (t, J=11.7 Hz, 2H), 2.90-2.89 (m, 1H), 2.78 (d, J=4.5 Hz, 3H), 2.09-1.93 (m, 4H).

Synthesis of Compound 1026

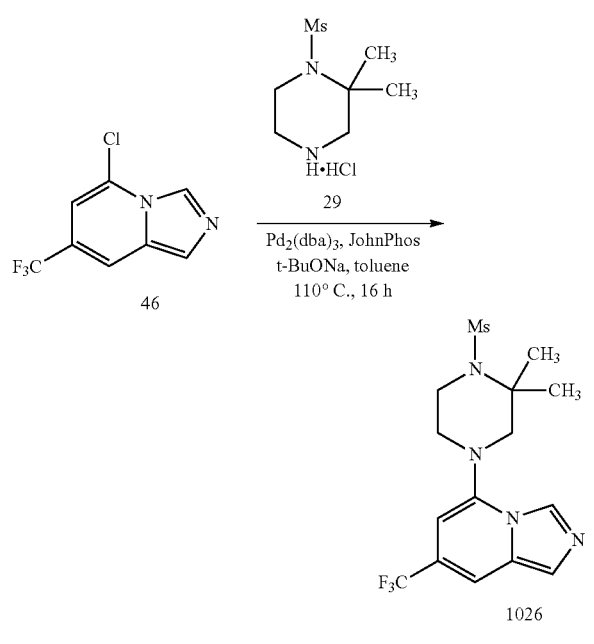

To a stirred solution of 46 (150 mg, 0.65 mmol) in toluene (10 mL) was charged with 29 (131 mg, 0.65 mmol), t-BuONa (130 mg, 1.3 mmol) at room temperature. The reaction mixture was purged with argon for 20 min. Pd$_2$(dba)$_3$ (123 mg, 0.13 mmol) and JohnPhos (6.00 mg, 0.018 mmol) were added to the reaction mixture and refluxed to 110° C. for 16 h. The reaction mixture was cooled to room temperature and concentrated under reduced pressure. The resultant slurry was diluted with EtOAc (100 mL) and washed with brine (2×75 mL). The organic phase was separated, dried over anhydrous Na$_2$SO$_4$, filtered and concentrated in vacuo to afford a residue. The residue was purified by combiflash column chromatography using Redisep® column (12 g, 100% EtOAc) to afford 1026 (6.50 mg, 12%) as a solid. MS (MM) m/z 377.1 [M+H]$^+$ HPLC: 96.5%, Zorbax SB-CN, 240 nm.

$^1$H NMR (300 MHz, DMSO-d$_6$): δ 8.50 (s, 1H), 7.92 (s, 1H), 7.74 (s, 1H), 6.35 (s, 1H), 3.65 (br s, 2H), 3.16 (br s, 2H), 3.06 (s, 3H), 3.06-3.00 (m, 2H), 1.55 (s, 6H).

Synthesis of Compound 1027

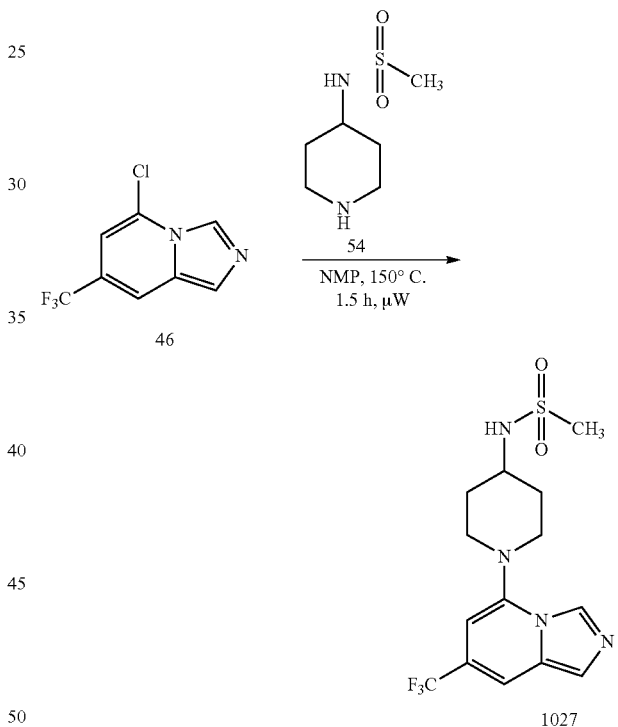

A solution of 46 (70.0 mg, 0.31 mmol) and 54 (169 mg, 0.95 mmol) in NMP (2.0 mL) was irradiated under microwave at 150° C. for 1.5 h. The reaction mixture was cooled to room temperature, diluted with EtOAc (100 mL), washed with water (20 mL) and brine (3×10 mL). The organic layer was collected, dried over anhydrous Na$_2$SO$_4$ and concentrated under reduced pressure. The crude residue was purified by combiflash column chromatography using Redisep® column (12 g, hexanes/EtOAc, 1:1) to afford 1027 (20.0 mg, 19%) as a solid. MS (MM) m/z 363.0 [M+H]$^+$. HPLC: 92.1%, XBridge C18, 220 nm. $^1$H NMR (300 MHz, DMSO-d$_6$): δ 8.36 (s, 1H), 7.86 (s, 1H), 7.71 (s, 1H), 7.27 (d, J=7.2 Hz, 1H), 6.25 (s, 1H), 3.42 (br d, J=12.3 Hz, 1H), 2.98 (s, 3H), 2.90 (t, J=10.5 Hz, 1H), 3.42 (br d, J=10.2 Hz, 1H), 1.81-1.70 (m, 2H).

Synthesis of Compound 1028

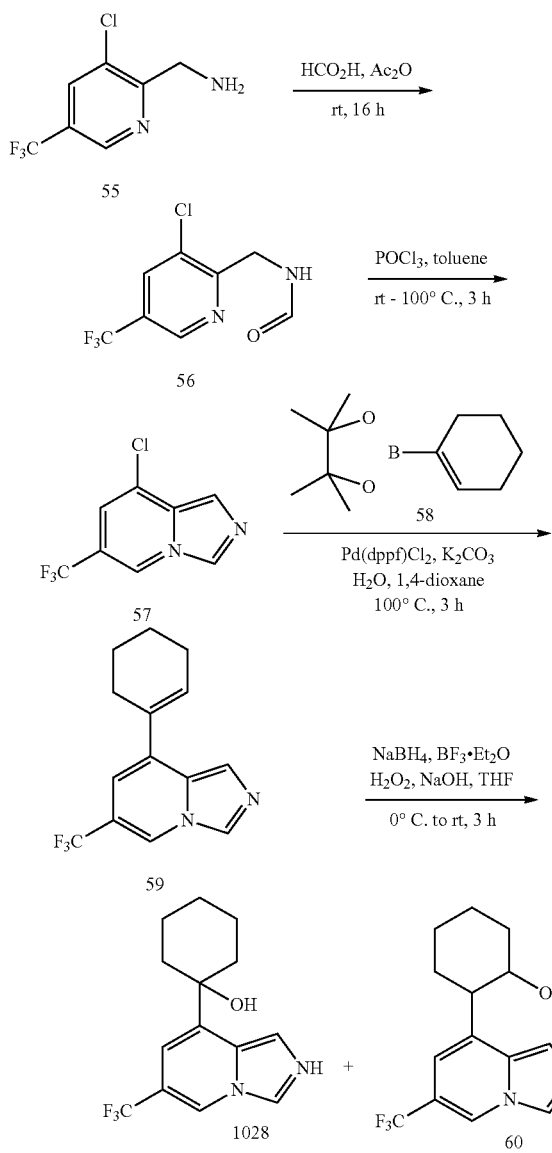

Preparation of 56—To a stirred solution of 55 (5.00 g, 23.91 mmol) in HCO$_2$H (50 mL) was charged with Ac$_2$O (50 mL) at room temperature. The reaction mixture was stirred at room temperature for 16 h. The reaction mixture was concentrated under reduced pressure and co-evaporated with toluene (2×100 mL) to afford 56 (8.10 g, 91%) as a solid. MS (MM) m/z 239.1 [M+H]$^+$.

Preparation of 57—To a stirred solution of 56 (5.00 g, 20.99 mmol) in toluene (25 mL) was charged with POCl$_3$ (2.5 mL) at room temperature. The reaction mixture was heated at 100° C. for 3 h. The reaction mixture was cooled, diluted with EtOAc (500 mL) and poured into aqueous NaOH solution (6 N, 10 mL). The layers were separated and the aqueous layer was extracted with EtOAc (3×50 mL). The combined organic layers were washed with water (200 mL) and brine (200 mL). The organic layer was dried over anhydrous Na$_2$SO$_4$ and concentrated in vacuo to afford 57 (4.00 g, 86%) as a solid. MS (MM) m/z 221.1 [M+H]$^+$.

Preparation of 59—To a stirred solution of 57 (500 mg, 2.27 mmol) in a mixture of 1,4-dioxane (5.0 mL) and H$_2$O (5.0 mL) was charged with 58 (314 mg, 2.49 mmol) and powdered K$_2$CO$_3$ (626 mg, 4.54 mmol) at room temperature. The reaction mixture was purged with argon for 20 min. Pd(dppf)Cl$_2$ (92.0 mg, 0.11 mmol) was added to the reaction mixture and was refluxed for 3 h. The mixture was cooled to room temperature and concentrated under reduced pressure. The resultant dark brown slurry was diluted with EtOAc (200 mL) and washed with brine (2×75 mL). The organic phase was separated, dried over anhydrous Na$_2$SO$_4$, filtered and concentrated in vacuo to afford a dark brown solid residue. The residue was further purified by combiflash column chromatography using Redisep® column (12 g, hexanes/EtOAc, 1:1) to afford 59 (380 mg, 63%) as a solid. MS (MM) m/z 368.1 [M+H]$^+$.

Preparation of Compound 1028—A stirred solution of 59 (1.00 g, 3.7439 mmol) in THF (20 mL) under nitrogen atmosphere was charged with NaBH$_4$ (162 mg, 4.1183 mmol) portionwise at 0° C. The reaction mixture was stirred for 30 min at room temperature. BF$_3$Et$_2$O (780 mg, 5.5 mmol) was added to the reaction mixture and was stirred at room temperature for additional 3 h. The reaction mixture was treated with H$_2$O$_2$ (20 mL), aqueous NaOH solution (6 M, 20 mL) and stirred for 30 min at same temperature. The reaction mixture was extracted with EtOAc (2×200 mL), washed with water (200 mL) and brine (200 mL). The reaction mixture was dried with anhydrous Na$_2$SO$_4$, filtered and concentrated under reduced pressure. The crude material was purified by combiflash column chromatography using Redisep® column (12 g, CH$_2$Cl$_2$/CH$_3$OH mixture as eluent). Isomers were further purified by preparative HPLC to afford 1028 (240 mg, 83%) as a solid. MS (MM) m/z 285.1[M+H]$^+$. HPLC: >99%, Eclipse XDB C18 Column, UV 220 nm Detection. $^1$H NMR (300 MHz, DMSO-d$_6$): δ 8.92 (s, 1H), 8.52 (s, 1H), 7.72 (s, 1H), 6.92 (s, 1H), 5.16 (s, 1H), 1.97-2.51 (m, 2H), 1.66-1.90 (m, 5H), 1.33-1.56 (m, 3H).

Synthesis of Compound 1029

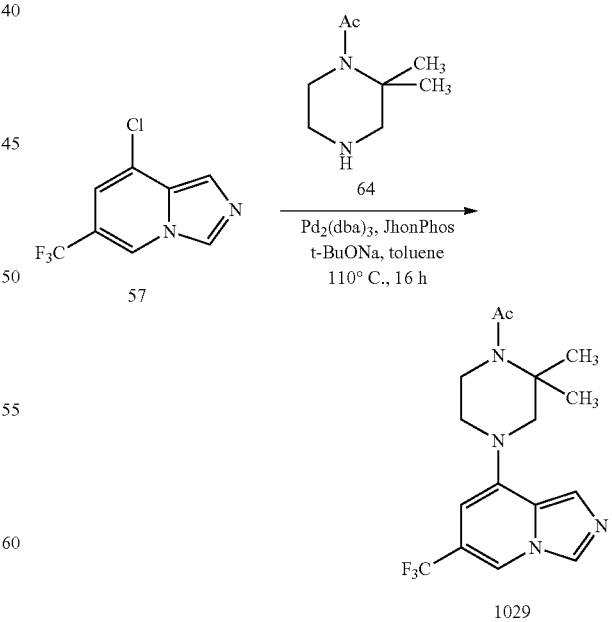

To a stirred solution of 57 (500 mg, 2.26 mmol) in toluene (10 mL) was charged with 64 (424 mg, 2.71 mmol) and powdered t-BuONa (433 mg, 4.52 mmol) at room temperature. The reaction mixture was purged with argon for 20 min. Pd₂(dba)₃ (413 mg, 0.452 mmol) and JhonPhos (67 mg, 0.22 mmol) were added to the reaction mixture and refluxed to 110° C. for 16 h. The reaction mixture was cooled to room temperature and concentrated under reduced pressure. The resultant slurry was diluted with EtOAc (100 mL) and washed with brine (2×75 mL). The organic phase was separated, dried over anhydrous Na₂SO₄, filtered and concentrated in vacuo to afford a residue. The residue was purified by combiflash column chromatography using Redisep® column (12 g, CH₂Cl₂/IPA, 9.3:0.7) to afford compound 1029 (20.0 mg, 2.3%) as a solid. MS (MM) m/z 341.1 [M+H]⁺. HPLC: 98.6%, Eclipse XDB C18, 220 nm.

¹H NMR (400 MHz, DMSO-d₆): δ 8.48 (s, 1H), 8.46 (s, 1H), 7.65 (s, 1H), 5.83 (s, 1H), 3.73 3.67 (m, 2H), 3.68 (d, J=2.4 Hz, 2H), 3.51 (s, 1H), 2.02 (s, 3H), 1.46 (s, 6H).

Synthesis of Compound 1030

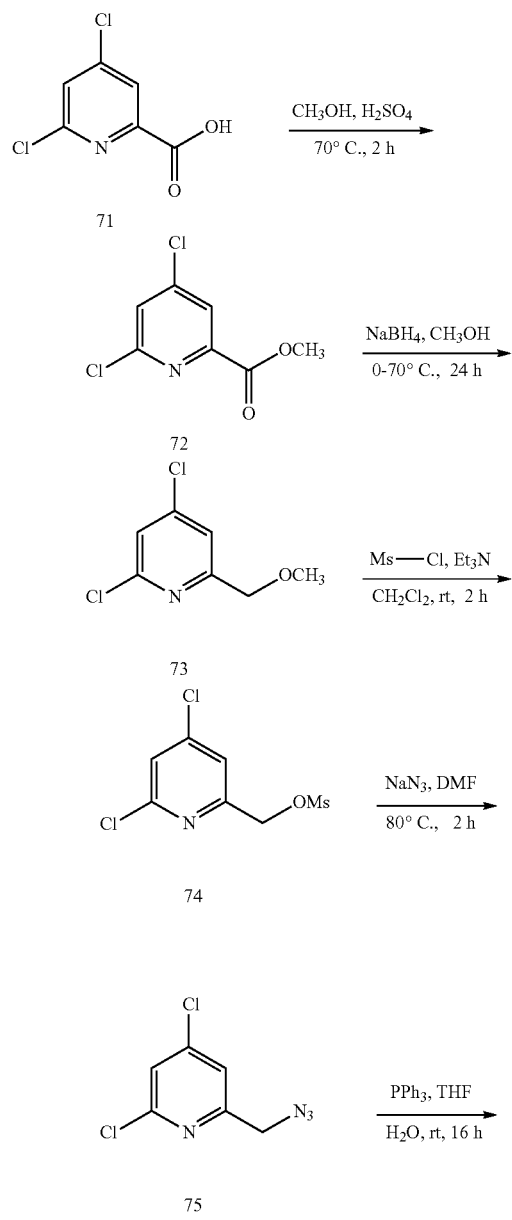

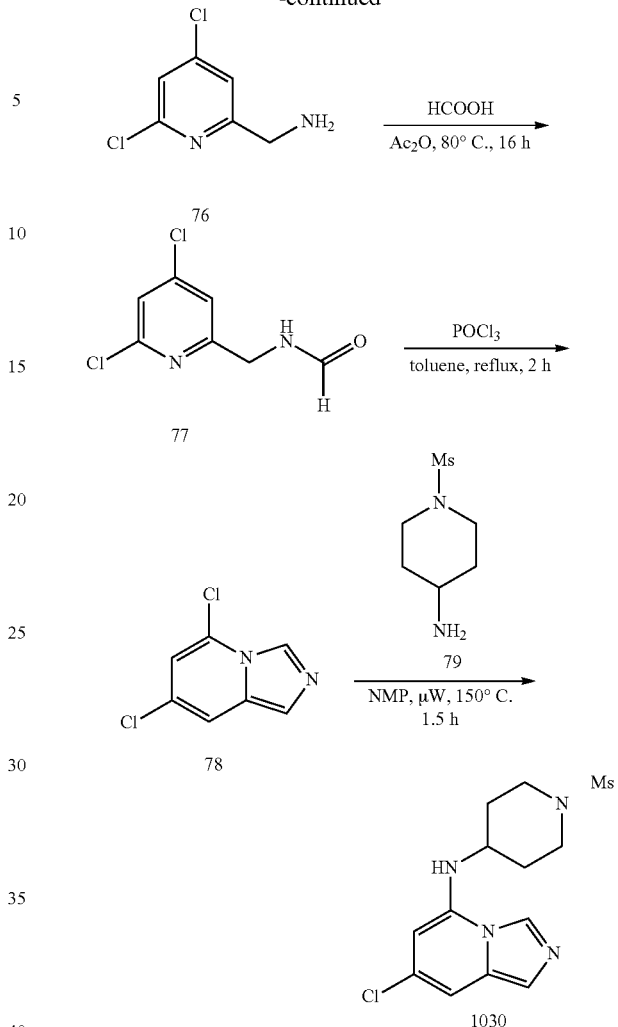

Preparation of 72—To a stirred solution of 71 (20.0 g, 104.1 mmol) in CH₃OH (200 mL) was charged with conc H₂SO₄ (1.0 mL) at room temperature. The reaction mixture was heated at 70° C. for 2 h. The reaction mixture was concentrated under reduced pressure, diluted with EtOAc (100 mL) and poured into saturated NaHCO₃ solution (80 mL). The layers were separated and the aqueous layer was extracted with EtOAc (2×150 mL). The combined organic layer was washed with water (100 mL) and brine (100 mL). The organic layer was dried over anhydrous Na₂SO₄ and concentrated under reduced pressure to afford 72 [20.0 g (crude)] as a liquid. MS (MM) m/z 207.1 [M+H]⁺.

Preparation of 73—To a stirred solution of 72 (20.0 g, 97 mmol) in CH₃OH (80 mL) was charged with NaBH₄ (14.35 g, 388 mmol) portionwise for 15 min at 0° C. The reaction mixture was stirred at 70° C. for 24 h. The reaction mixture was cooled to room temperature, concentrated under reduced pressure and portioned between water (200 mL) and EtOAc (3×300 mL). The combined organic layer was washed with water (100 mL) and brine (100 mL). The organic layer was dried over anhydrous Na₂SO₄ and concentrated in vacuo to afford 73 [18.5 g (crude)] as a solid. MS (MM) m/z 179.1 [M+H]⁺.

Preparation of 74—To a solution of 73 (18.5 g, 103.9 mmol) in CH₂Cl₂ (80 mL) at 0° C. was charged with Et₃N (28 mL, 207.8 mmol) followed by MsCl (12 mL, 155.8 mmol). The reaction mixture was stirred at room temperature for 2 h. The reaction mixture was diluted with water (100 mL) and extracted with EtOAc (3×200 mL). The organic phase was separated, dried over anhydrous $Na_2SO_4$ and concentrated in vacuo to afford 74 [20.0 g (crude)] as a gummy solid, which was used for next step without further purification. MS (MM) m/z 256.1 $[M+H]^+$.

Preparation of 75—A solution of 74 (20.0 g, 78 mmol) in DMF (80 mL) was charged with $NaN_3$ (15.2 g, 235 mmol) at room temperature. The reaction mixture was heated at 80° C. for 2 h. The reaction mixture was diluted with cold water (100 mL) and extracted with MTBE (3×200 mL). The organic phase was separated, dried over anhydrous $Na_2SO_4$ and concentrated in vacuo to afford 75 [11.0 g (crude)] as a liquid.

Preparation of 76—A stirred solution of 75 (11.0 g, 54.4 mmol) in THF (90 mL) and water (9.0 mL) was charged with $PPh_3$ (17.0 g, 65.3 mmol) at room temperature portionwise for 5 min. The reaction mixture was stirred at room temperature for 16 h. The reaction mixture was concentrated under reduced pressure. The residue was diluted with water (80 mL) and extracted with $CH_2Cl_2$ (2×50 mL). Aqueous layer was separated, acidified with HCl (2 N, 20 mL) and concentrated in vacuo to afford HCl salt of 76 [6.00 g (crude)] as a solid. MS (MM) m/z 177.1 $[M+H]^+$.

Preparation of 77—A stirred solution of 76 (6.00 g, 34 mmol) in $HCO_2H$ (100 mL) was charged with $Ac_2O$ (20 mL) at room temperature. The reaction mixture was stirred at 80° C. for 16 h. The reaction mixture was concentrated under reduced pressure and co-evaporated with toluene (2×30 mL) to afford 77 (5.00 g, 98%) as a gummy solid. MS (MM) m/z 205.1 $[M+H]^+$.

Preparation of 78—A stirred solution of 77 (1.20 g, 5.8 mmol) in toluene (10 mL) was charged with $POCl_3$ (1.2 mL) at 0° C. The reaction mixture was heated at 100° C. for 2 h. The reaction mixture was concentrated under reduced pressure, diluted with water (50 mL), basified with aqueous NaOH solution (6 N, 20 mL) and was extracted with EtOAc (3×100 mL). The organic phase was separated, dried over anhydrous $Na_2SO_4$ and concentrated in vacuo. The residue was purified by combiflash column chromatography using Redisep® column (12 g, hexanes/EtOAc, 8:2) to afford 78 (750 mg, 69%) as a solid.

Preparation of Compound 1030—A solution 78 (100 mg, 0.54 mmol) and 79 (481 mg, 2.7 mmol) in NMP (2.0 mL) was irradiated under microwave at 150° C. for 1.5 h. The reaction mixture was treated with cold water (3.0 mL) and extracted with EtOAc (3×8.0 mL). The organic layer was separated, dried over anhydrous $Na_2SO_4$ and concentrated in vacuo. The residue was purified by combiflash column chromatography using Redisep® column (4 g, EtOAc/hexanes, 9:1) to afford compound 1030 (15.0 mg, 8%) as an off-white solid. MS (MM) m/z 329.1 $[M+H]^+$. HPLC: 97.7%, Eclipse XDB C18, 220 nm. $^1H$ NMR (300 MHz, DMSO-$d_6$): δ 8.52 (s, 1H), 7.25 (s, 1H), 7.01 (s, 1H), 6.77 (d, J=8.1 Hz, 1H), 5.81 (s, 1H), 3.64-3.60 (m, 3H), 2.95-2.91 (m, 5H), 2.13-2.08 (m, 2H), 1.66-1.57 (m, 2H).

Synthesis of Compound 1031

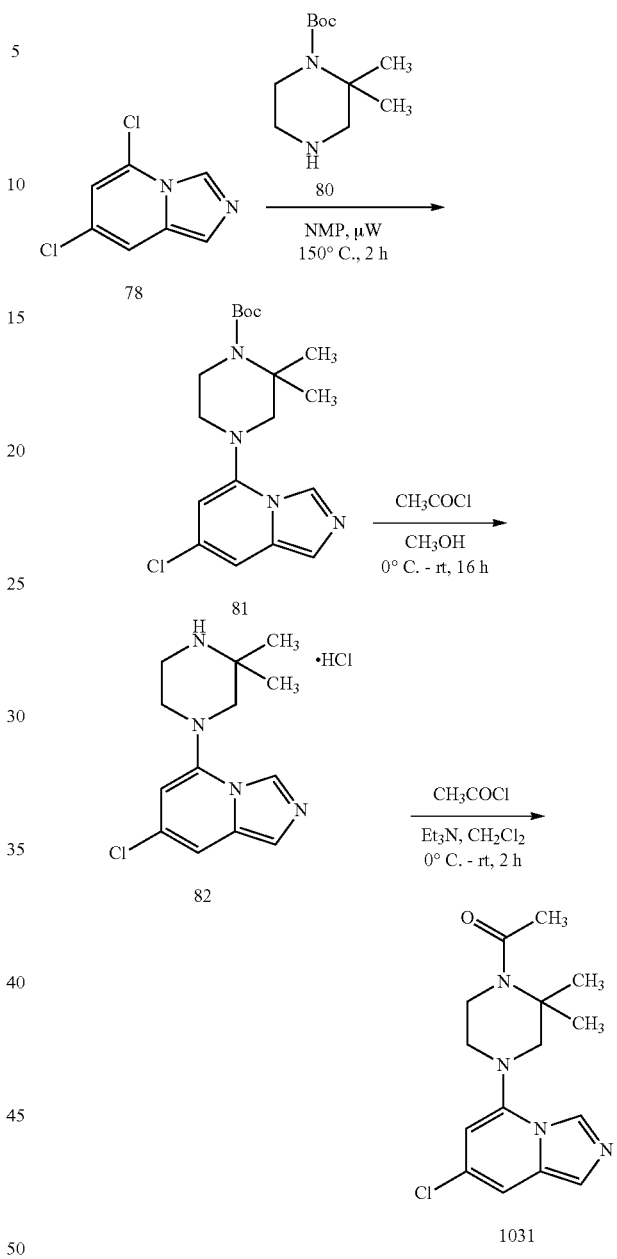

Preparation of 81—A solution of 78 (400 mg, 2.68 mmol), 80 (1.15 g, 13.4 mmol) in NMP (2.0 mL) was irradiated under microwave at 150° C. for 2 h. The reaction mixture was cooled to room temperature, diluted with cold water (10 mL) and extracted with EtOAc (3×30 mL). The organic phase was separated, dried over anhydrous $Na_2SO_4$ and concentrated in vacuo. The residue was further purified by combiflash column chromatography using Redisep® column (4 g, hexanes/EtOAc, 7:3) to afford 81 (200 mg, 35%) as a solid. MS (MM) m/z 265.1 $[M+H]^+$.

Preparation of 82—A stirred solution of 81 (200 mg, 0.75 mmol) in $CH_3OH$ (5.0 mL) was charged with AcCl (295 mg, 3.78 mmol) at 0° C. The reaction mixture was stirred at room temperature for 16 h. The reaction mixture was concentrated under reduced pressure. The residue was washed with MTBE (2×10 mL) and filtered to afford HCl salt of 82 [130 mg (crude HCl salt)] as a solid.

Preparation of Compound 1031—A solution of 82 (130 mg, 0.49 mmol) in $CH_2Cl_2$ (5.0 mL) at 0° C. was charged with $Et_3N$ (0.2 mL, 1.47 mmol) followed by AcCl (58 mg, 0.73 mmol). The reaction mixture was stirred at room temperature for 2 h. The reaction mixture was diluted with water (10 mL) and extracted with $CH_2Cl_2$ (3×10 mL). The organic phase was separated, dried over anhydrous $Na_2SO_4$ and concentrated in vacuo. The residue was further purified by combiflash column chromatography using Redisep® column (4 g, $CH_2Cl_2/CH_3OH$, 97:3) to afford 1031 (20.0 mg, 13%) as a solid. MS (MM) m/z 307.1 $[M+H]^+$. HPLC: 98.9%, Eclipse XDB C18, 220 nm. $^1H$ NMR (300 MHz, DMSO-$d_6$): δ 8.32 (s, 1H), 7.46 (s, 1H), 7.40 (s, 1H), 6.18 (s, 1H), 3.68 (t, J=5.1 Hz, 2H), 3.33-3.29 (m, 2H), 3.09 (s, 2H), 2.03 (s, 3H), 1.51 (s, 6H).

Synthesis of Compound 1032

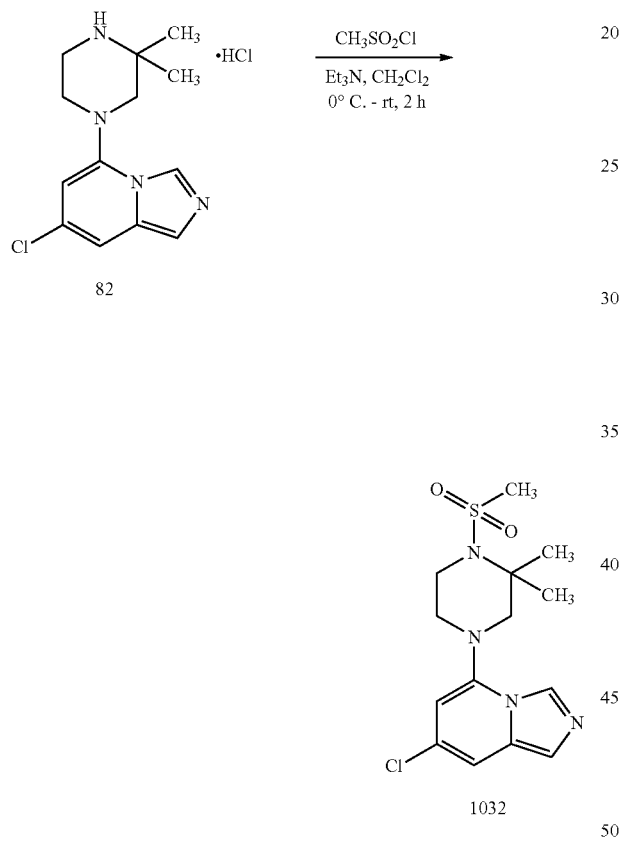

Preparation of 1032—A solution of 82 (100 mg, 0.37 mmol) in $CH_2Cl_2$ (5.0 mL) at 0° C. was charged with $Et_3N$ (0.1 mL, 0.56 mmol) followed by MsCl (65.0 mg, 0.56 mmol). The reaction mixture was stirred at room temperature for 2 h. Upon complete conversion of the starting material, the reaction mixture was diluted with water (5.0 mL) and extracted with $CH_2Cl_2$ (3×10 mL). The organic phase was separated, dried over anhydrous $Na_2SO_4$ and concentrated in vacuo. The residue was further purified by combiflash column chromatography using Redisep® column (4 g, $CH_2Cl_2/CH_3OH$, 97:03) to afford compound 1032 (12.0 mg, 9%) as a solid. MS (MM) m/z 343.1 $[M+H]^+$. HPLC: 96.8%, Eclipse XDB C18, 220 nm. $^1H$ NMR (400 MHz, DMSO-$d_6$): δ 8.32 (s, 1H), 7.51 (s, 1H), 7.42 (s, 1H), 6.23 (s, 1H), 3.62 (d, J=4.4 Hz, 2H), 3.17-3.16 (s, 2H), 3.05 (s, 3H), 3.00 (s, 2H), 1.54 (s, 6H).

Synthesis of Compound 1033

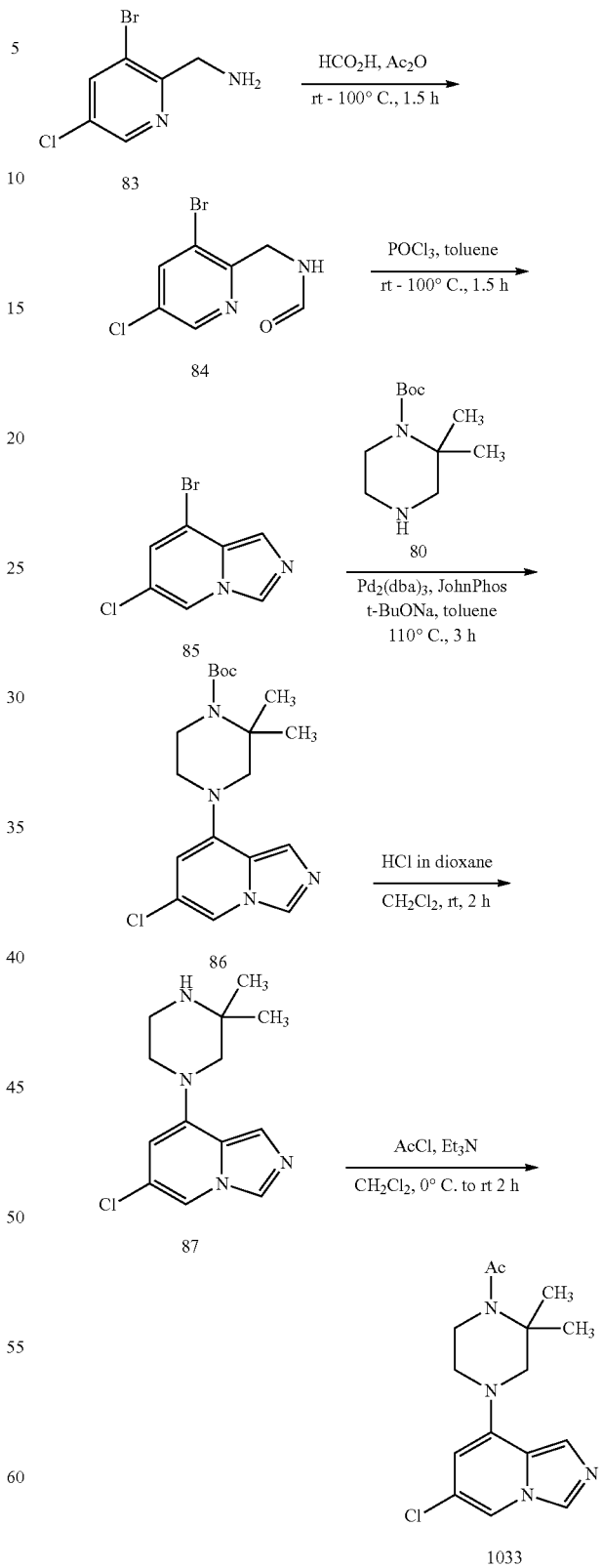

Preparation of 84—To a stirred solution of 83 (15.0 g, 71.0 mmol) in $HCO_2H$ (370 mL) was charged with $Ac_2O$ (750 mL) at room temperature. The reaction mixture was stirred at 100° C. for 1.5 h. The reaction mixture was concentrated under reduced pressure and co-evaporated with toluene (2×100 mL) to afford 84 (13.5 g, 76%) as a solid. MS (MM) m/z 249.1 [M+H]$^+$.

Preparation of 85—To a stirred solution of 84 (13.0 g, 54.0 mmol) in toluene (100 mL) was charged with POCl$_3$ (6.0 mL) at room temperature. The reaction mixture was heated at 100° C. for 1.5 h. The reaction mixture was cooled, diluted with EtOAc (300 mL) and poured into aqueous NaOH solution (1 N, 300 mL). The layers were separated and the aqueous layer was extracted with EtOAc (3×300 mL). The combined organic layers were washed with water (2×200 mL) and brine (200 mL). The organic layer was dried over anhydrous Na$_2$SO$_4$ and concentrated in vacuo to afford 85 (5.50 g, 45%) as a solid. MS (MM) m/z 230.4 [M+H]$^+$.

Preparation of 86—To a stirred solution of 85 (400 mg, 1.78 mmol) in toluene (20 mL) was charged with 80 (575 mg, 2.69 mmol) and powdered t-BuONa (512 mg, 5.34 mmol) at room temperature. The reaction mixture was purged with argon for 20 min. Pd$_2$(dba)$_3$ (146 mg, 0.18 mmol) and Johnphos (54.0 mg, 0.18 mmol) was added to the reaction mixture and refluxed for 3 h. The reaction mixture was cooled to room temperature and concentrated to 20 mL under reduced pressure. The resultant dark brown slurry was diluted with EtOAc (2×50 mL) and washed with brine (2×50 mL). The organic phase was separated, dried over anhydrous Na$_2$SO$_4$, filtered and concentrated in vacuo to afford a dark brown solid residue. The residue was purified by combiflash column chromatography using Redisep® column (12 g, hexanes/EtOAc, 1:1) to afford 86 (150 mg, 54%) as a solid. MS (MM) m/z 365.2 [M+H]$^+$.

Preparation of 87—A stirred solution of 86 (150 mg, 0.67 mmol) in CH$_2$Cl$_2$ (10 mL) was charged with HCl in 1,4-dioxane (4 N, 5.0 mL) over 10 min at 0° C. The reaction mixture was stirred at room temperature for 2 h and concentrated under the reduced pressure to afford 87 (60.0 mg) as an HCl salt. MS (MM) m/z 264.9 [M+H]$^+$.

Preparation of Compound 1033—A solution 87 (60.0 mg, 0.25 mmol) in CH$_2$Cl$_2$ (10 mL) was charged with Et$_3$N (0.12 mL, 0.75 mmol) followed by AcCl (0.1 mL, 0.5 mmol) over 10 min at 0° C. The reaction mixture was stirred at room temperature for 2 h. The reaction mixture was concentrated under reduced pressure to afford a dark brown solid residue. The residue was purified by combiflash column chromatography using Redisep® column (12 g, EtOAc/hexanes, 70:30) to afford compound 1033 (6.00 mg, 8%) as a solid. MS (MM) m/z 307.1 [M+H]$^+$. HPLC: 92.6%, Eclipse XDB-C18 column, 220 nm. $^1$H NMR (400 MHz, DMSO-d$_6$): δ 8.29 (s, 1H), 8.07 (s, 1H), 7.56 (s, 1H), 5.78 (s, 1H), 3.72 (d, J=5.2 Hz, 2H), 3.64 (d, J=5.2 Hz, 2H), 2.95 (s, 2H), 2.02 (s, 3H), 1.45 (s, 6H).

Synthesis of Compound 1034

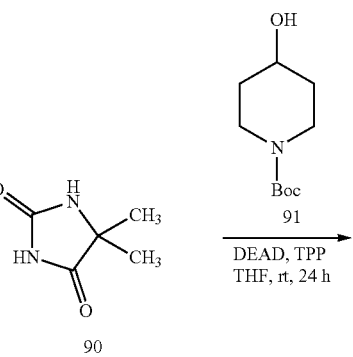

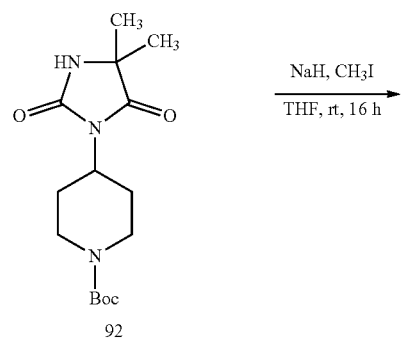

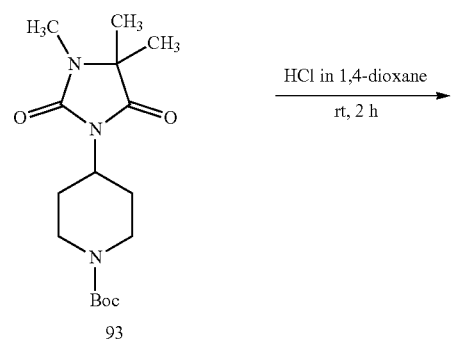

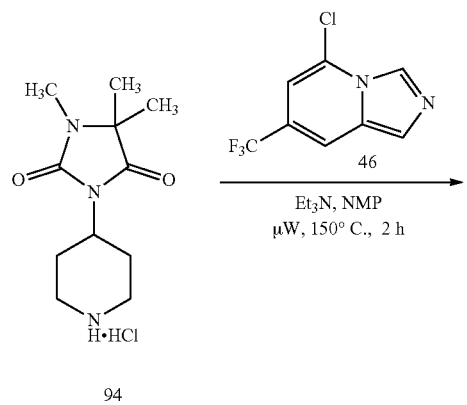

143
-continued

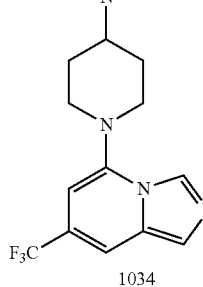

1034

Preparation of 92—To a stirred solution of 90 (1.50 g, 11.7 mmol) in THF (15 mL) was charged with TPP (4.50 g, 17.5 mmol), 91 (3.50 g, 17.5 mmol) at room temperature. The reaction mixture was cooled to 0° C. and diethyl aza dicarboxylate (3.0 mL, 17.5 mmol) was added dropwise to the mixture. The reaction mixture was stirred at room temperature for 24 h. The reaction mixture was quenched with water (25 mL). The layers were separated and the aqueous layer was extracted with EtOAc (2×20 mL). The combined organic layer was dried over anhydrous $Na_2SO_4$ and concentrated in vacuo to afford 92 [2.00 g (crude)] as a liquid. MS (MM) m/z 311.1 $[M+H]^+$.

Preparation of 93—A stirred solution of NaH (330 mg, 14.1 mmol) in THF (10 mL) was charged with 92 (2.00 g 9.44 mmol) in THF (10 mL) at 0° C. The reaction mixture was stirred at room temperature for 1 h. $CH_3I$ (1.2 mL, 18.8 mmol) was added to the reaction mixture and stirred at room temperature for 16 h. The reaction mixture was quenched with ice cold water (25 mL). The layers were separated and the aqueous layer was extracted with EtOAc (2×25 mL). The combined organic layer was dried over anhydrous $Na_2SO_4$ and concentrated in vacuo to afford 93 [1.80 g (crude)] as a liquid. MS (MM) m/z 325.1 $[M+H]^+$.

Preparation of 94—To a stirred solution of 93 (1.80 g, 5.53 mmol) in 1,4-dioxane (18 mL) was charged with HCl in 1,4-dioxane (4 M, 9.0 mL) The reaction mixture was stirred at room temperature for 2 h. The reaction mixture was filtered and the solid was washed with MTBE (10 mL) to afford 94 (720 mg, 66%) as a solid. MS (MM) m/z 226.1 $[M+H]^+$.

Preparation of Compound 1034—To a solution of 94 (368 mg, 1.36 mmol), 46 (100 mg, 0.45 mmol) and $Et_3N$ (0.19 mL, 1.36 mmol) in NMP (1.5 mL) was irradiated under microwave at 150° C. for 2 h. The reaction mixture was cooled to room temperature, treated with ice cold water (20 mL) and filtered. The solid was washed with $CH_2Cl_2$ (2.0 mL) and dried to afford 1034 (80.0 mg, 43%) as a solid. MS (MM) m/z 410.1 $[M+H]^+$. HPLC: 97.7%, Eclipse XDB-C18 column, 220 nm. $^1H$ NMR (400 MHz, DMSO-$d_6$): δ 8.34 (s, 1H), 7.87 (s, 1H), 7.72 (s, 1H), 6.30 (s, 1H), 4.09-4.02 (m, 1H), 3.56 (d, J=12.0 Hz, 1H), 2.91 (d, J=12.0 Hz, 1H), 2.59-2.53 (m, 2H), 1.76 (d, J=10.4 Hz, 1H), 1.41 (s, 6H).

144
Synthesis of Compound 1035

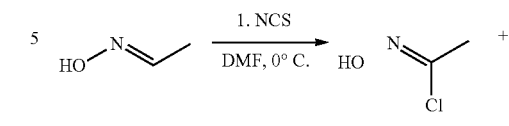

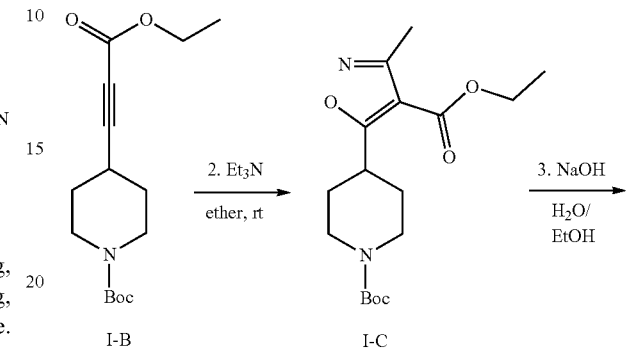

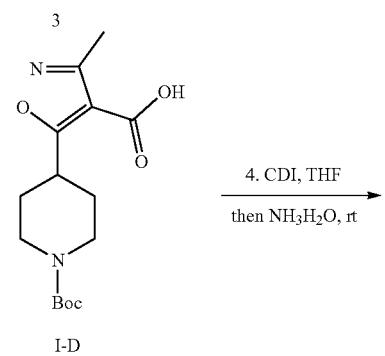

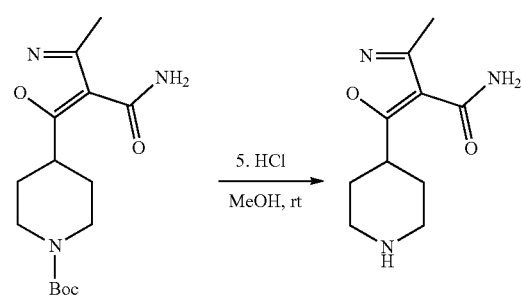

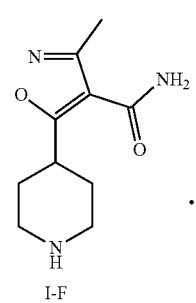

I-F

-continued

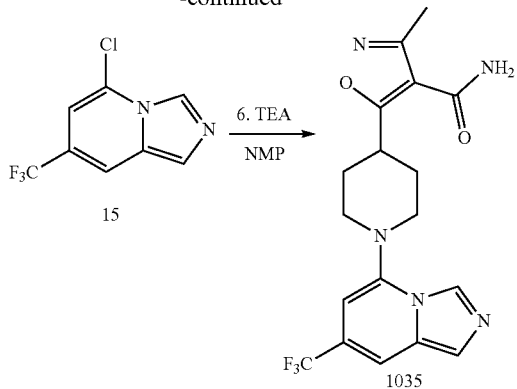

Step 1: Preparation of N-hydroxyacetimidoyl chloride (I-A)

To a stirred solution of acetaldehyde oxime (43.6 g, 0.74 mol) in DMF (200 mL) was added NCS (114.4 g, 0.87 mol) at 0° C. in three portions. Then the mixture was stirred at 25° C. for about 2 h until the acetaldehyde oxime was completely consumed. The resulting mixture was poured into water (600 mL) and extracted with diethyl ether (200 ml×4). The combined organic layers were dried over anhydrous $Na_2SO_4$ and concentrated in vacuum to give I-A, which was directly used into next step reaction without further purification.

Step 2: Preparation of ethyl 5-(1-(tert-butoxycarbonyl)piperidin-4-yl)-3-methylisoxazole-4-carboxylate (I-C)

To a stirred solution of tert-butyl 4-(3-ethoxy-3-oxoprop-1-yn-1-yl)piperidine-1-carboxylate (I-B) (52.0 g, 0.185 mol, commercially-available from PharmaBlock, Inc.) and I-A (crude from previous step, about 0.74 mol) in diethyl ether (1.0 L) was added drop wise TEA (104.0 mL, 0.74 mol) at 0° C. over 1 h. The resulting mixture was then stirred at RT for 16 h, after which the reaction mixture was washed with water (400 mL×2), and the organic layer was dried over anhydrous $Na_2SO_4$ and concentrated in vacuo. The residue was further purified by silica gel column chromatography (using a gradient of petroleum ether: EtOAc from 10:1 to 5:1) to afford I-C. MS (ESI) m/z: 339.1 (M+H+).

Step 3: Preparation of 5-(1-(tert-butoxycarbonyl)piperidin-4-yl)-3-methylisoxazole-4-carboxylic acid (I-D)

To a stirred solution of I-C (75.0 g, 0.22 mol) in EtOH (500 mL) was slowly added a cooled solution of NaOH (44.0 g, 1.1 mol) in water (500 ml) at 0° C. The mixture was then stirred at 20° C. for 2 h. After removal of EtOH by evaporation in vacuo, the residual aqueous solution was washed with DCM (125 mL×2), after which the pH was adjusted to 6 by the addition of citric acid. The resulting precipitate was filtered, washed with water (100 mL×2), and dried to afford I-D. MS (ESI) m/z: 310.9 (M+H+).

Step 4: Preparation of tert-butyl 4-(4-carbamoyl-3-methylisoxazol-5-yl)piperidine-1-carboxylate (I-E)

To a solution of compound I-D (13.0 g, 41.9 mmol) in THF (200 mL) was added CDI (13.6 g, 83.8 mmol) in several portions at 20° C. The mixture was then stirred at 20° C. for 2 hours. The resulting solution was then added drop wise to a solution of concentrated ammonium hydrate (27% wt, 150 mL) at 0° C. for 15 min. After the addition was completed, the mixture was stirred at 20° C. for 2 h. The solution was then concentrated under reduced pressure to remove most of organic solvent, and the aqueous solution was then diluted with water (100 mL), and the solution was extracted with DCM (200 mL×2). The combined organic layers were then washed with citric acid (100 mL x 2, 10% aqueous solution), followed by NaOH (100 mL x 2, 10% aqueous solution), after which the organic layer was dried over anhydrous $Na_2SO_4$ and concentrated in vacuo to give compound I-E. MS (ESI) m/z: 310.1 (M+H+).

Step 5: Preparation of 3-methyl-5-(piperidin-4-yl)isoxazole-4-carboxamide (I-F)

Compound I-E (12.0 g, 38.8 mmol) was dissolved in HCl in MeOH (4.0 M, 150 mL), and the resulting solution was stirred at room temperature for 1 hour. The solution was then concentrated in vacuo, and the residue was dissolved in water (100 mL). The resulting aqueous solution was then washed with DCM (50 mL×2) and the aqueous layer was then adjusted to pH=8-9 with the addition of $NaCO_3$ solid. Then the aqueous solution was then concentrated in vacuo, and the residue was washed with THF (100 mL×2) and filtered. The filtrate was collected, dried over anhydrous $Na_2SO_4$, and concentrated in vacuum to give compound I-F. MS (ESI) m/z: 210.1 (M+H+).

Step 6: Preparation of Compound 1035

To a vial were added 5-chloro-7-(trifluoromethyl)imidazo[1,5-a]pyridine (15) (100 mg, 0.453 mmol), 3-methyl-5-(piperidin-4-yl)isoxazole-4-carboxamide hydrochloride (HCl salt of I-F) (200 mg, 0.814 mmol), NMP (1500 μl) and $Et_3N$ (500 μl, 3.59 mmol). The mixture was heated at 150° C. for 18 h. The mixture was then filtered purified by mass triggered reversed phase HPLC (eluting with a linear gradient of acetonitrile in water with TFA modifier) to afford 3-methyl-5-(1-(7-(trifluoromethyl)imidazo[1,5-a]pyridin-5-yl)piperidin-4-yl)isoxazole-4-carboxamide, TFA (1035). $^1$H NMR (600 MHz, DMSO-$d_6$) δ 8.86 (s, 1H), 7.95 (s, 1H), 7.92 (s, 1H), 7.55 (s, 1H), 7.48 (s, 1H), 6.47 (s, 1H), 3.60-3.35 (m, 3H), 2.98-2.88 (m, 2H), 2.30 (s, 3H), 2.15-1.92 (m, 4H); MS (EI) Calc'd for $C_{18}H_{19}F_3N_5O_2[M+H]^+$, 394; found 394.

Synthesis of Compound 1036

Compound 1036 was made in an analogous fashion to compound 1035 except that intermediate I-G was used in place of I-E. The preparation of I-G is described below.

Preparation of Tert-butyl 4-(3-methyl-4-(methylcarbamoyl)isoxazol-5-yl)piperidine-1-carboxylate (I-G)

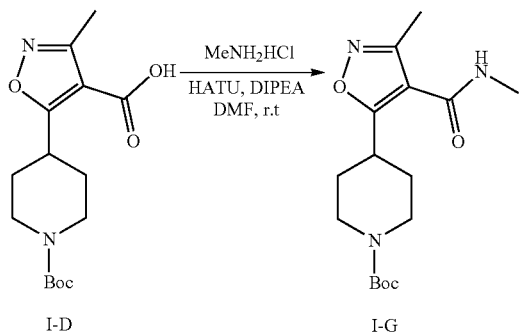

To a mixture of compound I-D (44.0 g, 0.142 mol), HATU (64.7 g, 0.17 mol) and methylamine hydrochloride (29.2 g, 0.426 mol) in DMF (500 mL) was added DIPEA (82.4 g, 0.639 mol) at 0° C. The resulting mixture was stirred at 20° C. for 2 h. DMF was then removed in vacuo, and the residue was partitioned with water (300 mL) and DCM (300 mL). The water layer was extracted with DCM (300 mL×2), and the combined organic layers were dried over anhydrous $Na_2SO$ and concentrated in vacuo. The residue was further purified by silica gel column chromatography (eluting with petroleum ether:EtOAc=1:1) to give compound I-G. MS (ESI) m/z: 324.1 (M+H$^+$).

Synthesis of Compound 1037

Compound 1037 was made in an analogous fashion to step 6 of compound 1035 except that 6-amino-1,3-dimethyl-5-(piperazin-1-yl)-1,2,3,4-tetrahydropyrimidine-2,4-dione (commercially available from Enamine Building Blocks) was used in place of I-F.

Preparation of Compound 1038

Compound 1038 was made in an analogous fashion to step 6 of compound 1035 except that 4-(1H-tetrazol-1-yl)-piperidine (commercially available from Aurora Building Blocks) was used in place of I-F.

| Example | Structure | Chemical Name | Exact Mass [M + H]+ |
|---|---|---|---|
| 1035 | 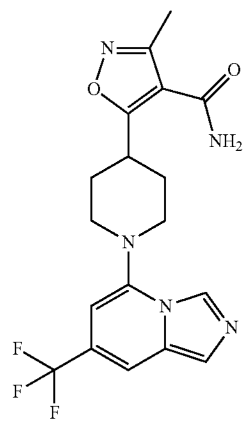 [SMILES: Cc1noc(C2CCN(c3cc(C(F)(F)F)cc4cncn34)CC2)c1C(N)=O] | 3-methyl-5-{1-[7-(trifluoromethyl)imidazo[1,5-a]pyridin-5-yl]piperidin-4-yl}isoxazole-4-carboxamide | Calc'd 394, found 394 |
| 1036 | 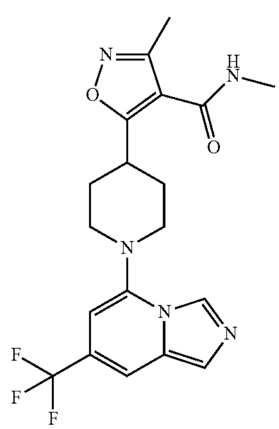 [SMILES: CNC(=O)c1c(C)noc1C1CCN(c2cc(C(F)(F)F)cc3cncn23)CC1] | N,3-dimethyl-5-{1-[7-(trifluoromethyl)imidazo[1,5-a]pyridin-5-yl]piperidin-4-yl}isoxazole-4-carboxamide | Calc'd 408, found 408 |

-continued

| Example | Structure | Chemical Name | Exact Mass [M + H]+ |
|---|---|---|---|
| 1037 | 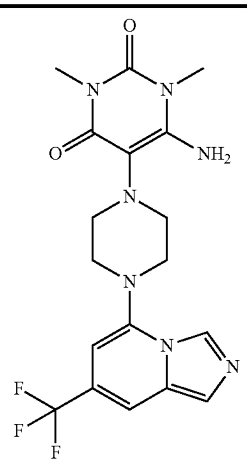 | 6-amino-1,3-dimethyl-5-{4-[7-(trifluoromethyl)imidazo[1,5-a]pyridin-5-yl]piperazin-1-yl}pyrimidine-2,4(1H,3H)-dione | Calc'd 424, found 424 |
| 1038 | 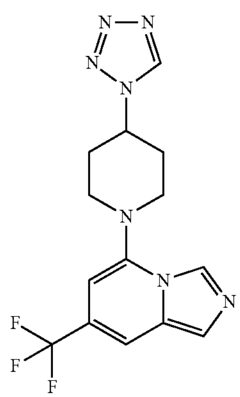 [SMILES: FC(F)(F)c1cc(N2CCC(n3cnnn3)CC2)n2cncc2c1] | 5-[4-(1H-tetrazol-1-yl)piperidin-1-yl]-7-(trifluoromethyl)imidazo[1,5-a]pyridine | Calc'd 338, found 338 |

All syntheses may be performed using reagents and reaction conditions suitable for similar reactions known in the field. All the compounds of the present invention may be produced by employing analogous syntheses.

Assays for Compounds 1001-1034

Exemplary compounds of the invention were prepared, and tested to determine their effect as TDO and/or IDO inhibitors. Two different assays were employed: 1. a cell-based assay for detecting the effect of test compounds on kynurenine production in two different cancer cell types. This assay utilised cancer cells which expressed either TDO or IDO and as such was used as a means of testing compound activity at these two enzymes in a cell-based context. 2. a TDO and IDO biochemical coupled assay which utilised recombinantly produced and purified TDO and IDO enzymes in combination with the enzyme formamidase. This coupled enzyme system allowed conversion of N-formylkynurenine produced by TDO or IDO activity to kynurenine which was then quantified by fluorescence following addition of Erhlich's Reagent The protocols for these are set out below.

Cell Based Assay for Detection of Kynurenine Produced by TDO and/or IDO

A172 (human glioblastoma) and SKOV3 (human ovarian adenocarcinoma) cells were seeded in a 96 well plate at 30,000 or 40,000 cells per well respectively in phenol red-free RPMI supplemented with 10% FCS, 2 mM L-glutamine and 500 µM L-tryptophan. IDO expression was induced in the SKOV3 cells by the addition of 500 ng/ml IFN-γ. Cells were incubated at 37° C. with or without the addition of test compound. After 48 hours, the cells were removed by centrifugation and Erhlich's reagent was added to the supernatant. The Erhlich's reagent was incubated for 5 minutes before the absorbance was read at 490 nM.

TDO and IDO Biochemical Coupled Assay

Recombinant human IDO or TDO was incubated in 50 mM KPO4 (pH 7.0), 0.5 mM EGTA, 0.5 mM EDTA, 0.05% Triton™ X100, 20 mM ascorbate, 10 µM methylene blue, 500 U/ml catalase, 50 µg/ml KynB (kynurenine formamidase). TDO assays were carried out in the presence of 330 µM L-tryptophan, while IDO assays had the addition of 45 µM L-tryptophan. After incubation for 17 minutes at room temperature the reactions were stopped by the addition of Erhlich's reagent and incubated at room temperature for 5 minutes before the fluorescence was read (Ex 475, Em530).

The pIC50 values for exemplary compounds are shown in Table 1 and Table 2.

TABLE 1 pIC50 values for Kynurenine cell-based assays determined for test compounds

| Compound | A172 Kynurenine cell based assay, pIC50 | SKOV3 Kynurenine cell based assay, pIC50 |
|---|---|---|
| 1001 | +/− | + |
| 1002 | ++ | + |
| 1003 | ++ | + |
| 1004 | + | +/− |
| 1005 | ++ | + |
| 1006 | ++ | + |
| 1007 | +++ | + |
| 1008 | +/− | + |
| 1009 | +/− | ++ |
| 1010 | +++ | + |
| 1011 | + | +/− |
| 1012 | ++ | + |
| 1013 | + | + |
| 1014 | +++ | +++ |
| 1015 | ++ | + |
| 1016 | +++ | ++ |
| 1017 | ++ | +/− |
| 1018 | ++ | + |
| 1019 | ++ | + |
| 1020 | + | +/− |
| 1021 | +++ | +++ |
| 1022 | +++ | +++ |
| 1023 | ++ | +++ |
| 1024 | ++ | +++ |
| 1025 | ++ | +++ |
| 1026 | +++ | +++ |
| 1027 | ++ | ++ |
| 1028 | +++ | ++ |
| 1029 | +++ | ++ |
| 1030 | ++ | ++ |
| 1031 | +++ | +++ |
| 1032 | ++ | +++ |
| 1033 | +++ | ++ |
| 1034 | ++ | ++ |

Key:
+++ = pIC$_{50}$ ≥5.50
++ = pIC$_{50}$ 4.50-5.49
+ = pIC$_{50}$ 4.00-4.49
+/− = pIC$_{50}$ <4.00

TABLE 2 pIC50 values for IDO and TDO inhibition determined for test compounds

| Compound | hTDO biochemical assay, pIC50 | hIDO biochemical assay, pIC50 |
|---|---|---|
| 1001 | +/− | +/− |
| 1002 | +++ | +/− |
| 1003 | +++ | +/− |
| 1004 | +++ | + |
| 1005 | +++ | ++ |
| 1006 | +++ | ++ |
| 1007 | +++ | + |
| 1008 | +/− | +/− |
| 1009 | +++ | +/− |
| 1010 | +++ | ++ |
| 1011 |  | + |
| 1012 | +++ | ++ |
| 1013 | ++ | ++ |
| 1014 | +++ | +++ |
| 1015 | + | ++ |
| 1016 | +++ | +++ |
| 1017 | + | + |
| 1018 | ++ | ++ |
| 1019 | ++ | ++ |
| 1020 | ++ | + |
| 1021 | +++ | +++ |
| 1022 | +++ | +++ |
| 1023 | +++ | +++ |
| 1024 | +++ | +++ |
| 1025 | +++ | +++ |
| 1026 | +++ | +++ |
| 1027 | +++ | ++ |
| 1028 | +++ | ++ |
| 1029 | +++ | +++ |
| 1030 | +++ | +++ |
| 1031 | +++ | +++ |
| 1032 | +++ | +++ |
| 1033 | +++ | +++ |
| 1034 | ++ | ++ |

++ = pIC$_{50}$ 4.50-5.49
+ = pIC$_{50}$ 4.00-4.49
+/− = pIC$_{50}$ <4.00

Assays for Compounds 1021 and 1035-1038

IDO1 Enzyme Assay

Compounds to be tested were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 555 acoustic liquid handler (Labcyte).

HIS-tagged IDO1 protein was recombinantly expressed in *Escherichia coli* using ZYP5052 autoinduction media supplemented with 500 µM delta aminolevulinic acid for 48 hours at 16 degrees Celcius. IDO1 protein was purified using $Ni^{2+}$-affinity resin and size exclusion chromatography. Purified protein was then diluted in assay buffer (50 mM Tris pH 7.0, 1% glycerol, 20 uM methylene blue, 0.05% Tween-20, 20 mM sodium ascorbate, 100 units/mL catalase to obtain a final IDOL concentration of 40 nM. IDOL solution (30 uM) or buffer alone (30 uM) were dispensed to wells of the assay plate using a BioRAPTR liquid dispenser (Beckman Coulter). Assay plates containing compound and IDO1 enzyme were incubated at room temperature for 30 minutes. Afterwards, 10 µL of 400 µM tryptophan in assay buffer were added to each well of the assay plate using a BioRAPTR liquid dispenser. Plates were incubated at room temperature for 60 minutes and reactions were quenched by addition of 10 µL of 0.5 M methyl isonipecotate in dimethyl sulfoxide. Plates were sealed and incubated at 37 degrees Celcius for 4 hours or 50 degrees Celcius for 2 hours. The plates are allowed to cool and then centrifuged for 1 minute at 1000×g. The resulting fluoresence was measured in an Envision plate reader (Perkin Elmer) with a 400/25 nm excitation filter and an 510/20 nm emission filter.

The fluoresence intensity of each well was corrected for the background observed in wells that did not receive IDO1 and was expressed as a fraction of the intensity observed in wells that received IDO1 enzyme and DMSO only. Potencies were calculated by linear least squares fit to the four parameter logistic IC50 equation.

IDO1 HEK293 Cellular Assay

Compounds to be tested were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 550 acoustic liquid handler (Labcyte).

HEK293 cell pellets were resuspended to $5\times10^5$ cells/mL in complete HEK293 culture media (89% DMEM, 10% FBS, 1% penicilllin/streptomycin). Suspended cells (2 mL) were dispensed into each well of a 6-well Corning plate (Catalog#3516). Cells were allowed to attach and were incubated for 20 hours at 37 degrees Celcius in a 5% $CO_2$ incubator. Flag-IDO1 vector (Genscript True ORF Gold, 2 ug) in 150 uL of Opti-MEM medium was added to to each well of a Corning 24 well plate (Cat#3527) and incubated for 5 minutes at room temperature. To each well of the 24-well plate was added 150 μL Lipofectamine 2000 (Gibco) and the plate incubated at room temperature for 20-30 minutes. To each well of attached cells in the 6-well plate, 250 μL of the transfection mix from the 24well plate was gently added to each well and IDO1 protein was allowed to express for 24-30 hours at 37 degrees Celcius in a 5% $CO_2$ incubator.

Media was removed from the cells which were then washed with 2 mL Dulbecco's phosphate-buffered saline (DPBS). After removal of DPBS, 0.5 mL of TrypLE (Gibco) was added and incubated at 5 minutes until cells lift from the surface of the wells. Complete HEK293 culture media (4 mL) was added to each well and cells were collected and pooled into a conical tube. Cells were pelleted at 200×g for 5 minutes and resuspended in an equal volume of complete DMEM medium. Cells were diluted to $4\times10^5$ cells per mL in complete HEK293 media. L-Tryptophan was added to added to give a final concentraiton of 200 μM. The diluted transfected cells (50 μL) or nontransfected cells (50 μL) were dispensed into wells of Greiner black 384-well assay plates (catalog #781086) containing previously diluted compounds. The plate is briefly mixed and centrifuged at 200×g for 10 seconds to collect cells at the bottom of the plate. Plates were covered and incubated for 20-24 hours at 37 degrees C. in a 5% $CO_2$ incubator. Afterwards 10 μL of 0.5 M methyl isonipecotate in dimethyl sulfoxide was added to each well, mixed, sealed, and centrifuged at 500 rpm for 10 seconds. Plates were incubated at 37 degrees in a 5% $CO_2$ incubator overnight to develop fluoresence. The plates are allowed to cool and then centrifuged for 1 minute at 1000×g. The resulting fluoresence was measured in an Envision plate reader (Perkin Elmer) with a 400/25 nm excitation filter and an 510/20 nm emission filter.

The fluoresence intensity of each well was corrected for the background observed in wells with untransfected cells and was expressed as a fraction of the intensity observed in wells of IDO1 transfected cells and DMSO only. Potencies were calculated by linear least squares fit to the four parameter logistic $IC_{50}$ equation.

The pIC50 values for compounds 1021 and 1035-1038 are shown in the following Table 3.

TABLE 3

The pIC50 values for compounds 1021 and 1035-1038.

| Ex. No. | IDO1 Enzyme, pIC50 | HEK293 cell, pIC50 |
|---|---|---|
| 1021 | 6.8 | 6.7 |
| 1035 | 6.6 | 6.3 |
| 1036 | 6.4 | 5.6 |
| 1037 | 6.1 | 5.4 |
| 1038 | 6.0 | 6.1 |

Tables 1-3 show that representative compounds show strong TDO and IDO inhibitory function.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

The invention claimed is:

1. A compound selected from one of the following formulae:

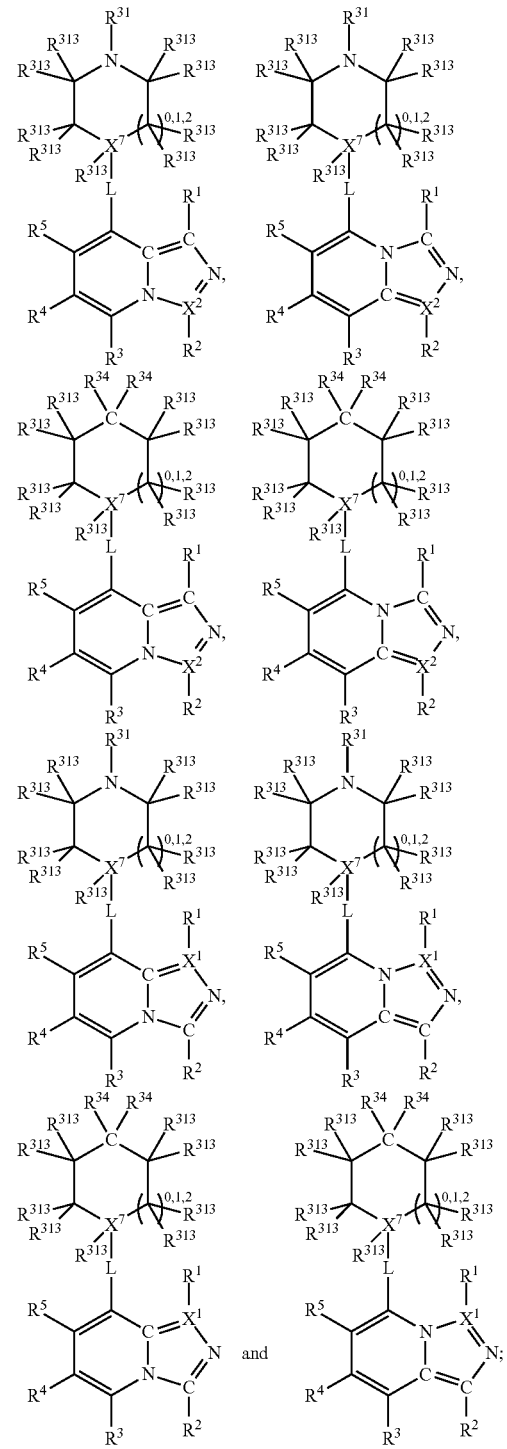

wherein:

each of $X^1$ and $X^2$ is C;

$X^7$ is selected from C and N;

each of $R^1$ and $R^2$ is H;

each of $R^3$ and $R^5$ is H;

$R^4$ is an organic group selected from halogen, an unsubstituted $C_1$-$C_6$ alkyl group, a $C_1$-$C_6$ alkyl group substituted with 1-3 halogens, a $C_3$-$C_6$ cycloalkyl group, a $C_1$-$C_6$ alkoxy group, and a nitrile group;

$R^{31}$ is selected from:
- H;
- a substituted or unsubstituted linear or branched carbonyl group selected from —(CO)Me, —(CO)Et, —(CO)Pr, —(CO)iPr, —(CO)nBu, —(CO)iBu, —(CO)tBu, —(C O)Ph, —(CO)CH$_2$Ph, —(CO)CH$_2$OH, —(CO)CH$_2$OCH$_3$, —(CO)CH$_2$NH$_2$, —(CO)CH$_2$N HMe, —(CO)CH$_2$NMe$_2$, —(CO)-cyclopropyl, —(CO)-1,3-epoxypropan-2-yl, —(CO)N H$_2$, —(CO)NHMe, —(CO)NMe$_2$, —(CO)NHEt, —(CO)NEt$_2$, —(CO)-pyrollidine-N-yl, —( CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
- a substituted or unsubstituted sulphonyl group selected from —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$, —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe;
- —NH—C(O)—C$_{1-4}$alkyl;
- —NH—SO$_2$—C$_{1-4}$alkyl;
- a substituted or unsubstituted phenyl group selected from P-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-PH-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)2-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-;
- an aromatic heterocyclic group selected from pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl; and
- a substituted or unsubstituted saturated heterocyclic group selected from piperidin-3-yl, piperidin-4-yl, tetrahydrofuran-3-yl, tetrahydropyran-3-yl, and tetrahydropyran-4-yl;

each $R^{34}$ is independently selected from:
- H;
- a halogen;
- a nitrile group;
- a substituted or unsubstituted linear or branched $C_1$-$C_6$ alkyl group selected from Me, Et, Pr, i-Pr, n-Bu, i-Bu, t-Bu, pentyl and hexyl;
- a substituted or unsubstituted linear or branched $C_1$-$C_6$ alkyl-aryl group selected from —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph;
- a substituted or unsubstituted linear or branched $C_1$-$C_6$ halogenated alkyl group selected from —CH$_2$F, —CH$_2$Cl, —CF$_3$, —CCl$_3$ —CBr$_3$, —Cl$_3$, —CH$_2$CF$_3$, —CH$_2$CCl$_3$, —CH$_2$CBr$_3$, and —CH$_2$Cl$_3$;
- an —NH$_2$ group,
- a substituted or unsubstituted linear or branched primary, secondary or tertiary $C_1$-$C_6$ amine group selected from —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$-NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt;
- a substituted or unsubstituted amino-aryl group selected from —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, and —NH-2,(3,4,5 or 6)Bu$_2$-Ph,
- a substituted or unsubstituted cyclic amine or amido group selected from pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl;
- a substituted or unsubstituted cyclic $C_3$-$C_8$ alkyl group selected from cyclopropyl, cyclobutyl, cyclopentyl, cyclohexyl, cycloheptyl and cyclooctyl;
- —OH;
- a substituted or unsubstituted linear or branched $C_1$-$C_6$ alcohol group selected from —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH;

a substituted or unsubstituted linear or branched $C_1$-$C_6$ carboxylic acid group selected from —COOH, —$CH_2$COOH, —$CH_2CH_2$COOH, —$CH_2CH_2CH_2$COOH, —$CH_2CH_2CH_2CH_2$COOH, and —$CH_2CH_2CH_2CH_2CH_2$COOH;

a substituted or unsubstituted linear or branched carbonyl group selected from —(CO)Me, —(CO)Et, —(CO)Pr, —(CO)iPr, —(CO)nBu, —(CO)iBu, —(CO)tBu, —(C O)Ph, —(CO)$CH_2$Ph, —(CO)$CH_2$OH, —(CO)$CH_2$O$CH_3$, —(CO)$CH_2NH_2$, —(CO)$CH_2$N HMe, —(CO)$CH_2NMe_2$, —(CO)-cyclopropyl, —(CO)-1,3-epoxypropan-2-yl; —(CO)N HMe, —(CO)$NMe_2$, —(CO)NHEt, —(CO)$NEt_2$, —(CO)-pyrollidine-N-yl, —(CO)-morph oline-N-yl, —(CO)-piperazine-N-yl, —(CO)-N-methyl-piperazine-N-yl, —(CO)NHC$H_2CH_2$OH, —(CO)NHC$H_2CH_2$OMe, —(CO)NHC$H_2CH_2NH_2$, —(CO)NHC$H_2CH_2$NH Me, and —(CO)NHC$H_2CH_2NMe_2$;

a substituted or unsubstituted linear or branched $C_1$-$C_6$ carboxylic acid ester group selected from —COOMe, —COOEt, —COOPr, —COO-i-Pr, —COO-n-Bu, —COO-i-Bu, —COO-t-Bu, —$CH_2$COOMe, —$CH_2CH_2$COOMe, —$CH_2CH_2CH_2$COOMe, and —$CH_2CH_2CH_2CH_2$COOMe;

a substituted or unsubstituted linear or branched $C_1$-$C_6$ amide group selected from —CO—$NH_2$, —CO—NMeH, —CO—$NMe_2$, —CO—NEtH, —CO—NEtMe, —CO—$NEt_2$, —CO—NPrH, —CO—NPrMe, and —CO—NPrEt;

a substituted or unsubstituted linear or branched $C_1$-$C_7$ amino carbonyl group selected from —NH—CO—Me, —NH—CO—Et, —NH—CO—Pr, —NH—CO-Bu, —NH—CO-pentyl, —NH—CO-hexyl, —NH—CO—Ph, —NMe-CO-Me, —NMe-CO-Et, —NMe-CO—Pr, —NMe-CO-Bu, —NMe-CO-pentyl, —NMe-CO-hexyl, and —NMe-CO-Ph;

a substituted or unsubstituted linear or branched $C_1$-$C_7$ alkoxy or aryloxy group selected from —OMe, —OEt, —OPr, —O-i-Pr, —O-n-Bu, —O-i-Bu, —O-t-Bu, —O-pentyl, —O-hexyl, —O$CH_2$F, —OCH$F_2$, —OC$F_3$, —O-Ph, —O—$CH_2$-Ph, —O—$CH_2$-(2,3 or 4)-F-Ph, —O—$CH_2$-(2,3 or 4)-Cl-Ph, —$CH_2$OMe, —$CH_2$OEt, —$CH_2$OPr, —$CH_2$OBu, —$CH_2CH_2$OMe, —$CH_2CH_2CH_2$OMe, —$CH_2CH_2CH_2CH_2$OMe, and —$CH_2CH_2CH_2CH_2CH_2$OMe;

a substituted or unsubstituted linear or branched aminoalkoxy group selected from —O$CH_2CH_2NH_2$, —O$CH_2CH_2$NHMe, —O$CH_2CH_2NMe_2$, —O$CH_2CH_2$NHEt, and —O$CH_2CH_2NEt_2$;

a substituted or unsubstituted sulphonyl group selected from —$SO_2$Me, —$SO_2$Et, —$SO_2$Pr, —$SO_2$iPr, —$SO_2$Ph, —$SO_2$-(2,3 or 4)-F-Ph, —$SO_2$-cyclopropyl, —$SO_2CH_2CH_2OCH_3$, —$SO_2NH_2$, —$SO_2$NHMe, —$SO_2NMe_2$, —$SO_2$NHEt, —$SO_2NEt_2$, —$SO_2$-pyrrolidine-N-yl, —$SO_2$-morpholine-N-yl, —$SO_2$NHC$H_2$OMe, and —$SO_2$NHC$H_2CH_2$OMe;

a substituted or unsubstituted aminosulphonyl group selected from —NH$SO_2$Me, —NH$SO_2$Et, —NH$SO_2$Pr, —NH$SO_2$iPr, —NH$SO_2$Ph, —NH$SO_2$-(2,3 or 4)-F-Ph, —NH$SO_2$-cyclopropyl, and —NH$SO_2CH_2CH_2OCH_3$;

a substituted or unsubstituted aromatic group selected from Ph-, 2-F-Ph-, 3-F-Ph-, 4-F-Ph-, 2-Cl-Ph-, 3-Cl-Ph-, 4Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-$I_2$-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)-$Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-, 4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-; and a substituted or unsubstituted saturated or unsaturated heterocyclic group selected from pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, furan-3-yl, piperidin-2-yl, piperidin-3-yl, piperidin-4-yl, tetrahydrofuran-2-yl, tetrahydrofuran-3-yl, tetrahydropyran-2-yl, tetrahydropyran-3-yl, and tetrahydropyran-4-yl;

each $R^{313}$ is independently selected from absent, H, —OH, halogen, and $C_{1-6}$ alkyl;

and L is absent.

2. The compound of claim 1, wherein $R^{31}$ is selected from:

—C(O)—$C_{1-4}$ alkyl;
—C(O)—NH—$C_{1-2}$ alkyl;
—$SO_2$-$C_{1-4}$alkyl;
—NH—C(O)—$C_{1-4}$ alkyl;
—NH—$SO_2$—$C_{1-4}$ alkyl;
a substituted or unsubstituted phenyl group selected from Ph-, 2-F-Ph-, 3-F-Ph-, 4F-Ph-, 2-Cl-Ph-, 3-Cl-Ph-, 4-Cl-Ph-, 2-Br-Ph-, 3-Br-Ph-, and 4-Br-Ph-;
an aromatic heterocyclic group selected from pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl; and
a substituted or unsubstituted saturated heterocyclic group selected from piperidin-3-yl, piperidin-4-yl, tetrahydrofuran-3-yl, tetrahydropyran-3-yl, and tetrahydropyran-4-yl.

3. The compound of claim 1, wherein each $R^{34}$ is independently selected from H and a group selected from:
a halogen;
a substituted or unsubstituted linear or branched $C_1$-$C_6$ alkyl group selected from Me, Et, Pr, i-Pr, n-Bu, i-Bu, t-Bu, pentyl and hexyl;
a substituted or unsubstituted linear or branched $C_1$-$C_6$ alkyl-aryl group selected from —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph;
a substituted or unsubstituted cyclic amine or amido group selected from pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl;
a substituted or unsubstituted linear or branched carbonyl group selected from —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$N HMe, —(CO)CH$_2$NMe$_2$, —(CO)-cyclopropyl, —(CO)-1,3-epoxypropan-2-yl, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)-N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
a substituted or unsubstituted linear or branched $C_1$-$C_6$ carboxylic acid ester group selected from —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe;
a substituted or unsubstituted linear or branched $C_1$-$C_6$ amide group selected from —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt;
a substituted or unsubstituted linear or branched $C_1$-$C_7$ amino carbonyl group selected from —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, and —NMe-CO-Ph;
a substituted or unsubstituted sulphonyl group selected from —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH2OCH$_3$), —SO$_2$NH$_2$, —SO$_2$NHMe, —SO$_2$NMe$_2$, —SO$_2$NHEt, —SO$_2$NEt$_2$, —SO$_2$-pyrolidine-N-yl, —SO$_2$-morpholine-N-yl, —SO$_2$NHCH$_2$OMe, and —SO$_2$NHCH$_2$CH$_2$OMe;
a substituted or unsubstituted aminosulphonyl group selected from —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$;
a substituted or unsubstituted aromatic group selected from Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph ;
a substituted or unsubstituted saturated or unsaturated heterocyclic group selected from pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl; and
a substituted or unsubstituted saturated heterocyclic group selected from piperidin-2-yl, piperidin-3-yl, piperidin-4-yl, tetrahydrofuran-2-yl, tetrahydrofuran-3-yl, tetrahydropyran-2-yl, tetrahydropyran-3-yl, and tetrahydropyran-4-yl.

4. A compound of the following formula, or a pharmaceutically acceptable salt thereof:

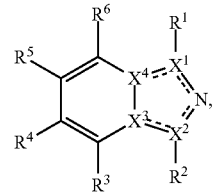

wherein each of $X^1$ and $X^2$ is C;
one of $X^3$ and $X^4$ is C and the other one of $X^3$ and $X^4$ is N;
each bond represented by a dotted line may be present or absent, provided that one of $X^3$ and $X^4$ has a double bond and the N between $X^1$ and $X^2$ has a double bond and the valencies of $X^1$, $X^2$, $X^3$, $X^4$ and N are maintained;
each of $R^1$ and $R^2$ is H;
each of $R^3$ and $R^5$ is H;
$R^4$ is an organic group selected from halogen, an unsubstituted $C_1$-$C_6$ alkyl group, a $C_1$-$C_6$ alkyl group substituted with 1-3 halogens, a $C_3$-$C_6$ cycloalkyl group, a $C_1$-$C_6$ alkoxy group, and a nitrile group; and wherein $R^6$ is selected from one of the following groups:

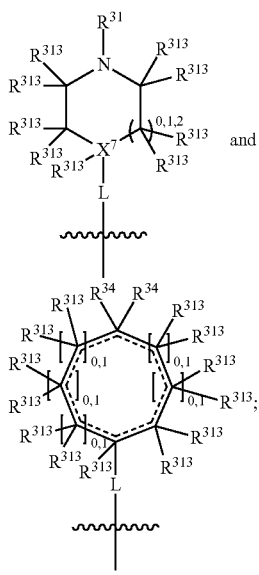

and wherein $X^7$ is C or N, one $R^{34}$ is H, $R^{31}$ and the other $R^{34}$ are selected from a —$COR^{311}$ group or an —$SO_2R^{311}$ group:

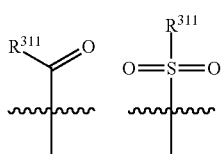

wherein $R^{311}$ is selected from:
- a substituted or unsubstituted linear or branched $C_1$-$C_6$ alkyl group selected from Me, Et, Pr, i-Pr, n-Bu, i-Bu, t-Bu, pentyl and hexyl;
- a substituted or unsubstituted linear or branched $C_1$-$C_6$ alkyl-aryl group selected from —$CH_2Ph$, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2Ph$, —$CH_2CH_2CH_2Ph$, —$CH_2CH_2CH_2CH_2Ph$, —$CH_2CH_2CH_2CH_2CH_2Ph$, and —$CH_2CH_2CH_2CH_2CH_2CH_2Ph$;
- a substituted or unsubstituted linear or branched $C_1$-$C_6$ halogenated alkyl group selected from —$CH_2F$, —$CF_3$, —$CH_2CF_3$;
- an —$NH_2$ group, or a substituted or unsubstituted linear or branched primary, secondary, or tertiary $C_1$-$C_6$ amine group selected from —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt;
- a substituted or unsubstituted amino-aryl group selected from —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)$F_2$-Ph, —NH-2,(3,4,5 or 6)$Cl_2$-Ph, —NH-2,(3,4,5 or 6)$Br_2$-Ph, —NH-2,(3,4,5 or 6)$I_2$-Ph, —NH-2,(3,4,5 or 6)$Me_2$-Ph, —NH-2,(3,4,5 or 6)$Et_2$-Ph, —NH-2,(3,4,5 or 6)$Pr_2$-Ph, and —NH-2,(3,4,5 or 6)$Bu_2$-Ph,
- a substituted or unsubstituted cyclic amine or amido group selected from pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl;
- a substituted or unsubstituted cyclic $C_3$-$C_8$ alkyl group selected from cyclopropyl, cyclobutyl, cyclopentyl, cyclohexyl, cycloheptyl and cyclooctyl;
- a substituted or unsubstituted linear or branched $C_1$-$C_6$ alcohol group selected from —$CH_2OH$, —$CH_2CH_2OH$, —$CH_2CH_2CH_2OH$, —$CH(CH_3)CH_2OH$, —$C(CH_3)_2OH$, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)_2CH_2OH$, —$CH_2CH_2CH_2CH_2CH_2OH$, and —$CH_2CH_2CH_2CH_2CH_2CH_2OH$;
- a substituted or unsubstituted linear or branched $C_1$-$C_7$ amino carbonyl group selected from —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, and —NMe-CO-Ph;
- a substituted or unsubstituted linear or branched $C_1$-$C_7$ alkoxy or aryloxy group selected from —OMe, —OEt, —OPr, —O-i-Pr, —O-n-Bu, —O-i-Bu, —O-t-Bu, —O-pentyl, —O-hexyl, —$OCH_2F$, —$OCHF_2$, —$OCF_3$, —O-Ph, —O—$CH_2$-Ph, —O—$CH_2$-(2,3 or 4)-F-Ph, —O—$CH_2$-(2,3 or 4)-Cl-Ph, —$CH_2OMe$, —$CH_2OEt$, —$CH_2OPr$, —$CH_2OBu$, —$CH_2CH_2OMe$, —$CH_2CH_2CH_2OMe$, —$CH_2CH_2CH_2CH_2OMe$, and —$CH_2CH_2CH_2CH_2CH_2OMe$;
- a substituted or unsubstituted linear or branched aminoalkoxy group selected from —$OCH_2CH_2NH_2$, —$OCH_2CH_2NHMe$, —$OCH_2CH_2NMe_2$, —$OCH_2CH_2NHEt$, and —$OCH_2CH_2NEt_2$;
- a substituted or unsubstituted aminosulphonyl group selected from —$NHSO_2Me$, —$NHSO_2Et$, —$NHSO_2Pr$, —$NHSO_2iPr$, —$NHSO_2Ph$, —$NHSO_2$-(2,3 or 4)-F-Ph, —$NHSO_2$-cyclopropyl, and —$NHSO_2CH_2CH_2OCH_3$;
- a substituted or unsubstituted aromatic group selected from Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-$I_2$-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)-$Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu- Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-;

an aromatic heterocyclic group selected from pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, furan-3-yl, piperidin-2-yl, piperidin-3-yl, piperidin-4-yl, tetrahydrofuran-2-yl, tetrahydrofuran-3-yl, tetrahydropyran-2-yl, tetrahydropyran-3-yl, and tetrahydropyran-4-yl; and each R$^{313}$ is independently selected from absent, H, —OH, halogen, and C$_{1-6}$ alkyl.

5. The compound of claim 1, selected from one of the following:

1002

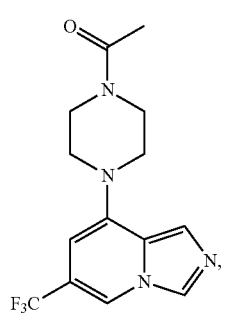

1003

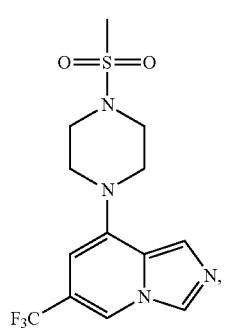

1004

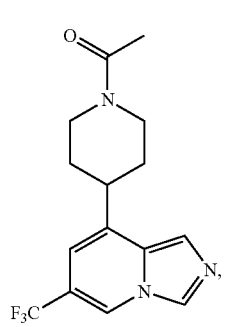

1005

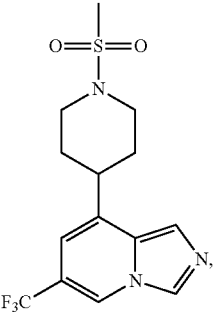

1006

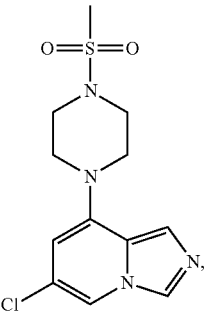

1007

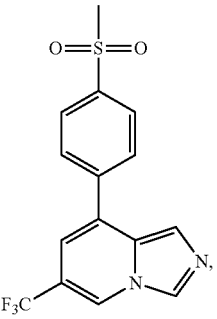

1010

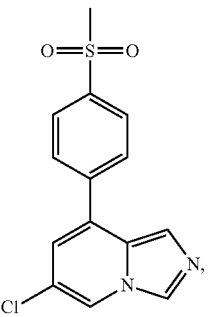

1012

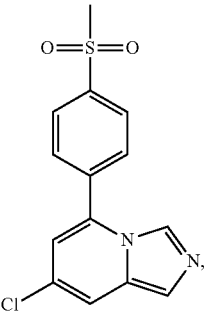

| | |
|---|---|
| 1013 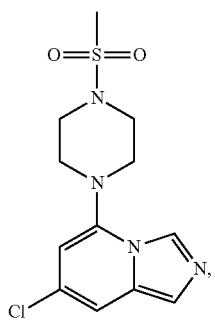 | 1018 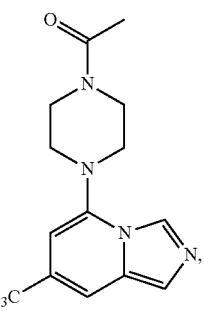 |
| 1014 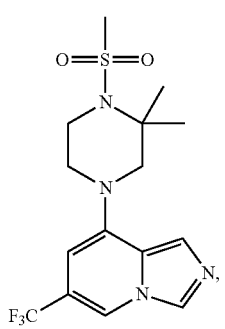 | 1019 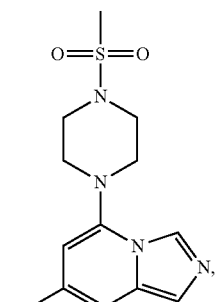 |
| 1015 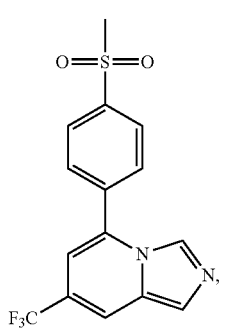 | 1020 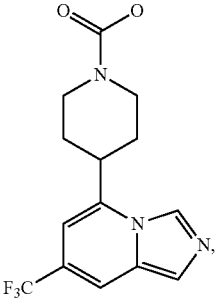 |
| 1016 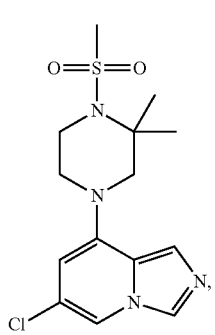 | 1021 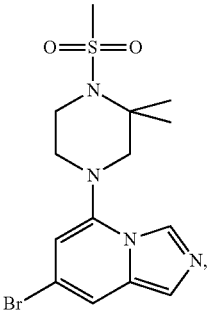 |
| 1017 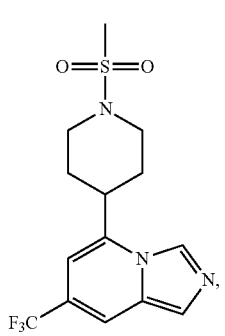 | 1022 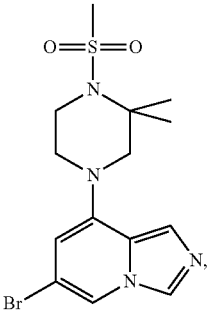 |

167
-continued
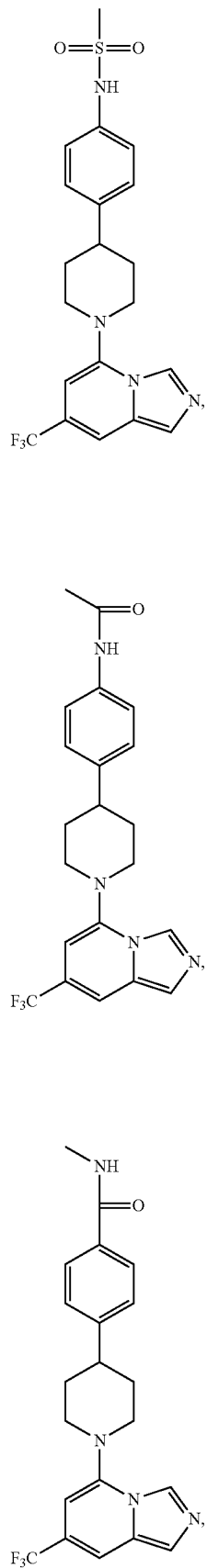
168
-continued
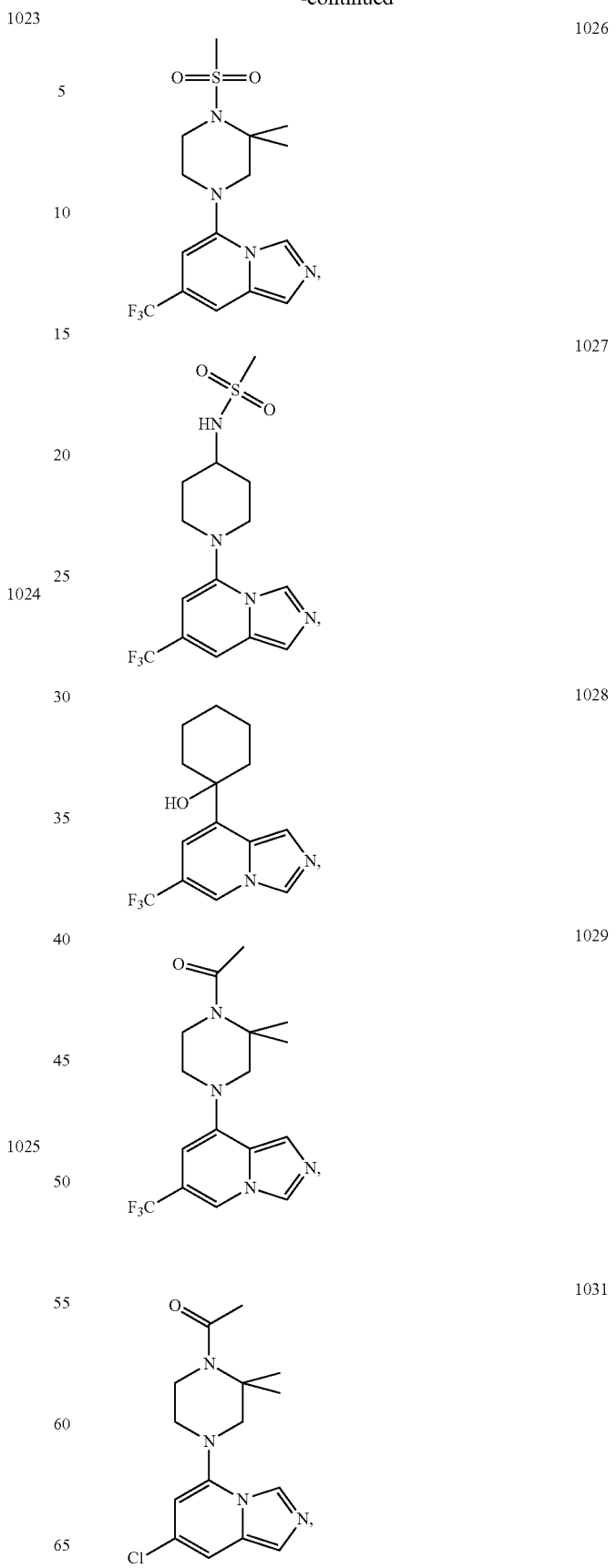

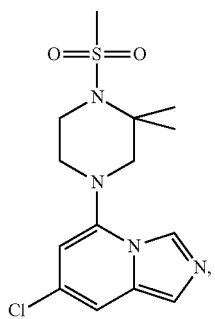
1032
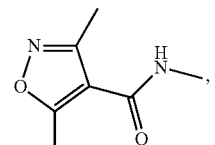
1036
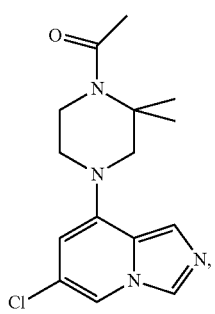
1033
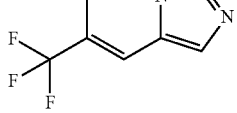
1037
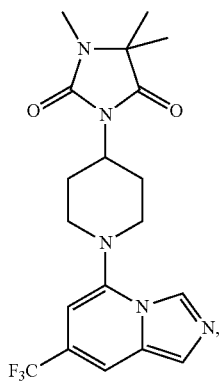
1034
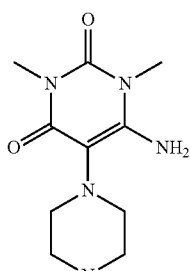
and
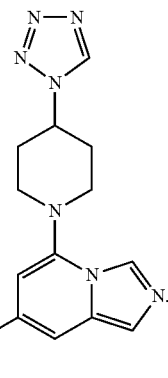
1038
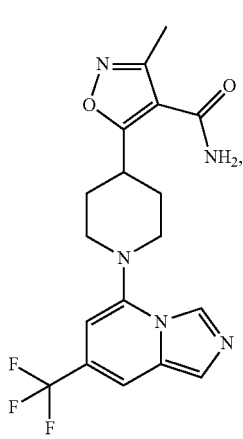
1035
6. A pharmaceutical composition comprising a compound of claim 1, and a pharmaceutically acceptable excipient.
7. A compound selected from formulae Ic and Id, or a pharmaceutically acceptable salt thereof:
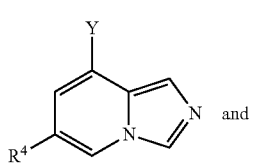
(Ic)
and -continued

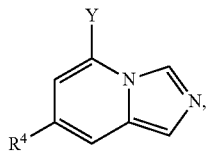
(Id)

wherein:
R⁴ is selected from the group consisting of (1) halogen, (2)C₁-C₄alkyl, optionally substituted with 1-3 halogens, and (3)C₃-C₆ cycloalkyl, optionally substituted with 1-3 groups independently selected from halogen and C₁-C₆alkyl; and
Y is selected from the group consisting of:

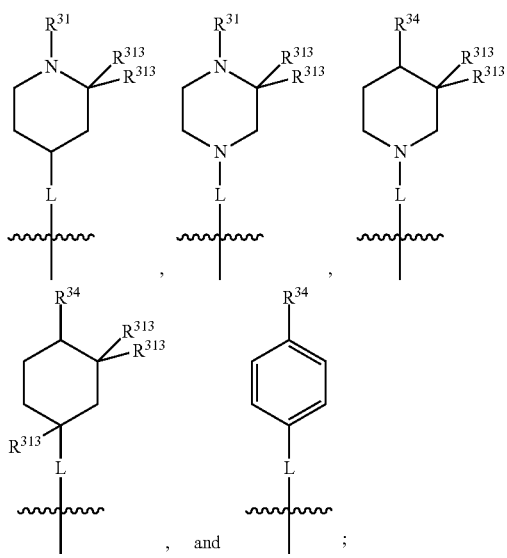

wherein
L is a bond;
R³¹ is selected from the group consisting of (1) H, (2) halogen, (3) —C(O)—C₁₋₄alkyl, (5) —S(O)₂—C₁₋₄alkyl, (6) —NH—C(O)—C₁₋₄alkyl, and (7) heterocyclyl, optionally substituted with 1-5 groups independently selected from C₁₋₆alkyl, oxo, —C(O)—H, —C(O)—NH₂, C(O)—NH—C₁₋₆ alkyl, —NH₂, and —NH—C₁₋₆alkyl;
R³⁴ is selected from the group consisting of (1) H, (2) halogen, (3) —C(O)—C₁₋₄alkyl, (4) —S(O)₂—C₁₋₄alkyl, (5) —NH—C(O)—C₁₋₄alkyl, and (6) heterocyclyl, optionally substituted with 1-5 groups independently selected from C₁₋₆alkyl, oxo, —C(O)—H, —C(O)—NH₂, C(O)—NH—C₁₋₆ alkyl, —NH₂, and —NH—C₁₋₆alkyl; and
each occurrence of R³¹³ is independently selected from the group consisting of (1) H and (2)C₁₋₄ alkyl.

8. The compound of claim 7, or a pharmaceutically acceptable salt thereof, wherein each heterocyclyl of R³¹ and R³⁴ is independently selected from the group consisting of:

2,3-dihydro-1,4-dioxinyl, dihydropyranyl, dihydropyrazinyl, dihydropyridazinyl, dihydropyridinyl, dihydropyrimidinyl, furanyl, imidazolyl, imidazolidinyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl wherein each of the heterocyclyl is optionally substituted with 1-5 groups independently selected from C₁₋₆alkyl, oxo, —C(O)—H, —C(O)—NH₂, C(O)—NH—C₁₋₆ alkyl, —NH₂, and —NH—C₁₋₆alkyl.

9. The compound of claim 7, or a pharmaceutically acceptable salt thereof, wherein:
R⁴ is selected from the group consisting of (1) halogen and (2)CF₃; and
Y is selected from the group consisting of:

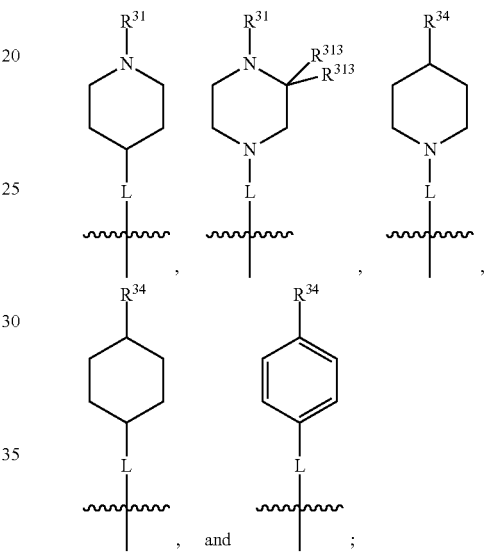

wherein
L is a bond;
R³¹ is selected from the group consisting of (1) —C(O)—CH₃, (2) —S(O)₂—CH₃, (3) —NH—C(O)—CH₃, (4) imidazolidinyl, (5) isoxazolyl, (6) tetrazolyl, and (7) 1,2,3,4-tetrahydropyrimidinyl; wherein each of (4), (5), (6) and (7) is optionally substituted with 1-5 groups independently selected from C₁₋₆alkyl, oxo, —C(O)—H, —C(O)—NH₂, C(O)—NH—C₁₋₆ alkyl, —NH₂, and —NH—C₁₋₆alkyl;
R³⁴ is selected from the group consisting of (1) H, (2) —C(O)—CH₃, (3) —S(O)₂—CH₃, (4) —NH—C(O)—CH₃, (5) imidazolidinyl, (6) isoxazolyl, (7) tetrazolyl, and (8) 1,2,3,4-tetrahydropyrimidinyl; wherein each of (5), (6), (7) and (8) is optionally substituted with 1-5 groups independently selected from C₁₋₆alkyl, oxo, —C(O)—H, —C(O)—NH₂, C(O)—NH—C₁₋₆ alkyl, —NH₂, and —NH—C₁₋₆alkyl; and
each occurrence of R³¹³ is independently selected from the group consisting of (1) H and (2) —CH₃.

* * * * *